US006495681B1

(12) United States Patent
Axt et al.

(10) Patent No.: US 6,495,681 B1
(45) Date of Patent: Dec. 17, 2002

(54) LOCAL ANESTHETIC COMPOUNDS AND USES

(75) Inventors: Sabine M. Axt, Sunnyvale, CA (US); Timothy J. Church, San Mateo, CA (US); Witold Hruzewicz, Berkeley, CA (US); John R. Jacobsen, San Francisco, CA (US); Thomas E. Jenkins, La Honda, CA (US); Yu-Hua Ji, San Mateo, CA (US); J. Kevin Judice, Montara, CA (US)

(73) Assignee: Theravance Inc., South San Francisco, CA (US)

( * ) Notice: Subject to any disclaimer, the term of this patent is extended or adjusted under 35 U.S.C. 154(b) by 0 days.

(21) Appl. No.: 09/690,019

(22) Filed: Oct. 17, 2000

Related U.S. Application Data

(62) Division of application No. 09/285,054, filed on Apr. 2, 1999, now Pat. No. 6,337,423.
(60) Provisional application No. 60/080,531, filed on Apr. 3, 1998, and provisional application No. 60/122,075, filed on Mar. 1, 1999.

(51) Int. Cl.$^7$ .................... C07D 273/08; A61K 31/33
(52) U.S. Cl. .................. 540/467; 544/400; 514/252.12; 514/183
(58) Field of Search .............. 540/467; 544/400; 514/252.12, 183

(56) References Cited

U.S. PATENT DOCUMENTS

| | | | |
|---|---|---|---|
| 3,267,104 A | | 8/1966 | Hermans et al. |
| 3,542,850 A | | 11/1970 | Hollowood et al. |
| 3,845,770 A | | 11/1974 | Theeuwes et al. |
| 3,898,070 A | | 8/1975 | Dazzi |
| 4,169,106 A | | 9/1979 | Diamond et al. |
| 4,252,804 A | * | 2/1981 | Joullie et al. |
| 4,326,525 A | | 4/1982 | Swanson et al. |
| 4,597,903 A | | 7/1986 | Gokel et al. |
| 4,948,769 A | | 8/1990 | Chapple |
| 4,948,906 A | | 8/1990 | Beard |
| 4,992,445 A | | 2/1991 | Lawter et al. |
| 5,023,252 A | | 6/1991 | Hseih |
| 5,134,232 A | | 7/1992 | Tsien et al. |
| 5,382,584 A | | 1/1995 | Balasubramanian |
| 5,389,630 A | | 2/1995 | Sato et al. |
| 5,405,975 A | | 4/1995 | Kuhn et al. |
| 5,453,264 A | | 9/1995 | Mori et al. |
| 5,516,864 A | * | 5/1996 | Kuhn et al. .................. 526/263 |
| 5,686,495 A | | 11/1997 | Goldin et al. |
| 5,719,197 A | | 2/1998 | Kanios et al. |
| 5,998,419 A | * | 12/1999 | Cook et al. |

FOREIGN PATENT DOCUMENTS

| | | |
|---|---|---|
| DE | 1204226 | 11/1965 |
| EP | 0 443 862 | 8/1991 |
| EP | 0541798 A1 | 3/1993 |
| GB | 692332 | 6/1953 |
| JP | 52-139060 * | 11/1977 |
| WO | 94/00419 | 1/1994 |
| WO | 97/30019 | 8/1997 |

OTHER PUBLICATIONS

Supuran, et al. Chemical Abstracts, vol. 116: 235532 (1992).
Arlander, et al. "Ropivacaine gel in active distal uncerative colitis and proctitis —a pharmacokinetic and exploratory clinical study," *Aliment Pharmacol. Ther.* 10:73–81 (1996).
Blight, et al. "Cutaneus Trunci Muscle Reflex of the Guinea Pig." *The Jrnl. of Comparative Neurology.* 296:614–633 (1990).
Bulbring, et al. "Biological Comparison of Local Anaesthetics." *J. Pharmacol. Exp. Therap.* 85:78–84 (1945).
Bundgaard, et al. "Esters of N,N–Disubstituted 2–Hydroxyacetamides as a Novel Highly Biolabile Prodrug Type for Carboxylic Acid Agents." *J. Med. Chem.* 30(3): 451–454 (1987).
Catterall, et al. "Structure and Function of Voltage–Gated Ion Channels," *Annu. Rev. Biochem.* 64:493–531 (1995).
Choi, et al. "Pharmacokinetic Nature of Tachyphylaxis to Lidocaine: Peripheral Nerve Blocks and Inflitration Anesthesia in Rats." *Life Sciences.* 61(12):177–184 (1997).
Dahlbom, R., et al. "Quaternary derivatives of aminocyclanilines." *Acta Pharm. Suecica.* 2:219–226 (1965).
Dahlbom, R. et al. "Quaternary derivatives of aminocyclanilines." *Acta Pharm. Suecica.* 2:227–230 (1965).
Dahlbom, R., et al. "III Bis(quaternary ammonium)salts." *Chem. Abs.* 63(12): 16235 (1965).
Danko, et al. "Block of sodium channels by internal mono and divalent guanidinium analogues." *Biophysical Journal.* 49:509–519 (1986).
Gorgels, et al. "Comparison of Procainamide and Lidocaine in Terminating Sustained Monomorphic Ventricular Tachycardia." *Am. J. Cardiol.* 78:43 (1996).
Grant, et al. "A Rat Sciatic Nerve Model for Independent Assessment of Sensory and Motor Block Induced by Local Anesthetics." *Anest. Analg.* 75:889–894 (1992).
Hamill, et al. "Improved Patch–Clamp Techniques for High- Resolution Current Recording from Cells and Cell–Free Membrane Patches." *Pflügers Arch.* 391:85–100 (1981).
Hille, et al. "An Improved Vaseline Gap Voltage Clamp for Skeletal Muscle Fibers." *J. Gen. Physiol.* 67: 265–293 (1976).

(List continued on next page.)

*Primary Examiner*—Shailendra Kumar
(74) *Attorney, Agent, or Firm*—David E. Boone; Jeffrey A. Hagenah

(57) ABSTRACT

Novel compounds, pharmaceutical compositions and methods are disclosed for producing local anesthesia of long-duration. The compounds of this invention are multibinding compounds that comprise from 2 to 10 ligands covalently attached to a linker or linkers, each ligand being capable of binding to a ligand binding site in a voltage-gated $Na^+$ channel to modulate the biological processes/functions thereof.

14 Claims, 14 Drawing Sheets

OTHER PUBLICATIONS

Hollowood, et al. "Local Anesthetics with Enhanced Affinity for Proteins." *J. of Med. Chem., US, American Chem. Soc.* 10(5): 863–867 (1967).

Hunt, et al. "Effect of Nebulized Lidocaine on Severe Glucocorticoid–Dependent Asthma," *Mayo Clin. Proc.* 71:361 (1996).

Khromov–Borisov, et al. "Bis(quarternary ammonium compounds) of some derivatives of 1,6–hexamethylenebis(aminoacetic acid)." *Chem. Abs.* 59(2): 1626 (1963).

Kizuka, H., et al. "Beta–andrenoceptor antagonist activity of bivalent ligands. 1. Diamide analogues of practolol." *J. Med. Chem.* 30(4): 722–726 (1987).

Kudryashova, I., et al. "Bis9dialkylaminoacetryl) derivatives of benzidine and 4,4'–diaminodiphenylethan series." *Chem. Abs.* 55(1): 449 (1961).

Kuzma, et al. "Progress in the Development of Ultra–Long-Acting Local Anesthetics." *Regional Anesthesia.* 22(6):543–554 (1997).

Lantos, et al. "Effects of Lidocaine on Cerebral Lipid Peroxidation and Neutophil Activation Following Complete Compression Ischemia." *Arch. Int. Pharmacodyn.* 331:179–188 (1996).

McNeal, et al. "[$^3$H]Batrachotoxinin A 20α–Benzoate Binding to Voltage–Sensitive Sodium Channels: A Rapdi and Quantitative Assay for Local Anesthetic Activity in a Variety of Drugs." *J. Med. Chem.* 28:381–388 (1985).

Motovilov, P.E., et al. "Comparative properties of xylocaine type anesthetics." *Chem. Abs.* 52(22): 20673 (1958).

Nielsen, et al. "Prodrugs as delivery systems. 68. Chemical and plasma–catalyzed hydrolysis of various esters of benzoic acid: a refrence system for designing prodrug esters of carboxylic acid agents." *Int. J. of Pharmaceutics.* 39:75–85 (1987).

Nielsen, et al. "Glycolamide Esters as Biolabile Prodrugs of Carboxylic Acid Agents: Synthesis, Stability, Bioconversion, and Physicochemical Properties." *J. Pharmaceutical Sciences.* 77(4):285–298 (1988).

Rosen, et al. "Electrophysiology and pharmacology of cardiac arrhythmias. V. Cardiac antiarrhythmic effects of lidocaine." *Am. Heart Journal.* 89(4): 526–536 (1975).

Starmer, C.F. "Theoretical characterization of ion channel blockade." *Biophysical Journal.* 52:405–412 (1987).

Strichartz, et al. "Neural Blockade in Clinical Anesthesia and Management of Pain." Chapter 2, $3^{rd}$ EditionMJ Cousins and PO Bridenburgh, Eds., Lippencott–Raven Publishers, Philadelphia (1998).

Svetkin, et al. "Kinetics of the alkylation of diamines by 2–haloacetamides and synthesis of high–molecular–weight compounds based on them." *Chemical Abstracts* 98(11): 484 (1983). (abstract only).

Thalhammer, et al. "Neurological Evaluation of the Rat during Sciatic Nerve Block with Lidocaine." *Anesthesiology.* 82(4): 1013–1025 (1995).

Vogtle, F., et al. "Kronenether mit haptophoren bzw. pharmakophoren Gruppen." *Chem. Ber.* 11: 1434–1439 (1978).

Wyeth, et al. "Effects of Lidocaine on Atrial Peptide Concentrations in Plasma and Urine." *Life Sciences.* 60(7): 473–477 (1997).

Yamashita, T., et al. "Synthesis of Crown Ether Dyes." *Bull. Chem. Soc. Jpn.* 53: 1550–1554 (1980).

V. J. Gatto et al., "Synthesis and Binding Properties of Bibracchial Lariat Ethers (BIBLEs): Survey of Synthetic Methods and Cation Selectivities", *J. Org. Chem.*, 1986, 51, 5373–5384.

* cited by examiner (From Aidley and Stanfield, Ion Channels (Cambridge University Press, 1996)

BENZOCAINE

BUPIVACAINE

ETIDOCAINE

MEPIVACAINE

LIDOCAINE

PRAMOXINE

PRILOCAINE

ROPIVACAINE

PROPARACAINE

TETRACAINE

◯ = ligand
n+m+core<100 atoms

Scheme H

Scheme I-1

Scheme I-2

Scheme J

Scheme K

Scheme M

Scheme N

Scheme O

Scheme P

Scheme Q

Scheme R

*Scheme S*

*Scheme T*

LOCAL ANESTHETIC COMPOUNDS AND USES

CROSS REFERENCE TO RELATED APPLICATIONS

This application is a divisional Ser. No. 09/285,054, filed Apr. 2, 1999, now U.S. Pat. No. 6,337,423, which claims the benefit of U.S. Provisional Serial No. 60/080,531, filed Apr. 3, 1998, and No. 60/122,075, filed Mar. 1, 1999, both of which are incorporated by reference in their entirety.

FIELD OF THE INVENTION

This invention relates to novel multibinding local anesthetic compounds that bind to voltage-gated $Na^+$ ion channels and thereby modulate their activity. The compounds of this invention comprise at least two ligands covalently connected by a linker or linkers, wherein at least one of the ligands in its monovalent (i.e. unlinked) state binds to and is capable of modulating the activity of a voltage-gated $Na^+$ ion channel. The ligands are linked together such that the multibinding compounds thus formed demonstrate a biologic and/or therapeutic effect on processes mediated by voltage-gated $Na^+$ ion channels that is greater than that of the same number of unlinked ligands made available for binding to the channels. In one preferred embodiment, the compounds of the present invention are capable of producing local anesthesia of longer duration than are the corresponding unlinked monovalent ligands. The invention also relates to methods of using such compounds and to methods of preparing them.

These multibinding local anesthetic compounds are particularly useful in treating conditions and diseases that require pain control. Accordingly, this invention also relates to pharmaceutical compositions comprising a pharmaceutically acceptable excipient and an effective amount of a compound of this invention.

BACKGROUND

State of the Art

Action potentials are generated in nerve and muscle cells by ion currents that pass selectively across plasma membranes through transmembrane ion channels. Local anesthetics exert their effects by specifically binding to $Na^+$ channels, thereby inhibiting $Na^+$ currents and causing the blockade of $Na^+$ channel-dependent impulse conduction. The necessary practical advantage of local anesthetics is that their action is reversible at clinically relevant concentrations and their use is followed by complete recovery of nerve and muscle function with no evidence of damage to nerve fibers or cells.

Ion channels are formed by the association of integral membrane proteins into a structure having a central hydrophilic pore. The structure of the voltage-gated sodium ion channel has been extensively studied (reviewed by W A Catterall, *Annu. Rev. Biochem.* 64: 493–531 (1995)). The channel consists of a complex of one α- and 2β-subunits. FIG. 1A illustrates the general features of the channel. The α-subunit is the pore-forming subunit, contains a voltage sensor and contains specific binding sites for local anesthetic drugs. This subunit consists of a polypeptide chain with four homologous domains (I–IV), each domain comprising 6 membrane-spanning protein helices (S1–S6). This subunit is flanked at the outer surface of the membrane by two β-subunits, which are heavily glycosylated and which interact with the lipid bilayer in which the channel is embedded. The $β_2$ chain is topologically similar to the $β_1$ chain, but is not shown in the figure.

Ion channels are characterized by their gating and selectivity properties. Selectivity refers to the rate at which different ion species pass through an open channel under standard conditions. The $Na^+$ channel pore is selectively permeable to $Na^+$, which passes through the channel at rates that are diffusion-limited, and which equilibrates according to the electrochemical gradient across the membrane. Gating is the process that regulates the opening and closing of an ion channel. The voltage-gated $Na^+$ channel opens and closes in response to changes in membrane potential. When the membrane is depolarized (i.e., the membrane potential becomes less negative ), the "resting" channel transitions through closed intermediate states to become an "open" $Na^+$-conducting channel. With time, the channel closes and becomes "inactivated" (i.e., refractory to reopening ). The channel recovers its ability to respond to a depolarizing stimulus by returning to the "resting state" after an interval of time.

There is considerable evidence that the channel itself is a specific receptor for local anesthetics. As mentioned above, the $Na^+$ channel contains specific binding sites for local anesthetic drugs, which exhibit stereoselectivity. FIG. 1B shows a highly schematic representation of the $Na^+$ channel illustrating differences in the binding sites for different classes of $Na^+$ channel modulators and blocking agents, as is currently understood.

The binding sites for neurotoxins, such as saxatoxin and tetrodotoxin (TTX), and scorpion and anemone toxins (ScTx) are thought to be located at the outer mouth of the channel pore. This region includes binding sites for cations, e.g. ammonium ions, as well.

Other, more lipid soluble toxins, such as batrachotoxin (BTX), veratridine, and aconitine, bind within the channel and act to spontaneously open the channel and/or prevent it from closing normally. Current understanding of neuronal sodium channels indicates that binding sites for "classical" local anesthetics (LA), such as lidocaine, as well as lipophilic quaternary ammonium ion channel blockers, may lie within the internal region of the channel, as shown. This binding site is understood to be allosterically linked to the BTX binding site. Lipophilic binding domains are found at the innermost region of the channel.

It has been suggested that tertiary amine drugs may have two binding sites on the channel, a first site located near the pore that preferentially binds charged species and a second site that binds neutral species. The binding of an anesthetic molecule to the first site would block ion permeation through the pore, while the binding to the second site would act to prevent conformational changes that are required for channel opening (G R Strichartz, Chapter 2, In: *Neural Blockade in Clinical Anesthesia and Management of Pain*, Third Edition, (M J Cousins and P O Bridenbaugh, Eds.), Lippincott-Raven Publishers, Philadelphia(1998)).

The inhibitory effect of certain local anesthetics is enhanced by membrane depolarization. This effect is attributed to a higher affinity of these local anesthetics for inactivated channels than for resting channels. Repetitive depolarizations potentiate anesthetic activity by "use-dependent" (phasic) block such that an increasing number of channels become stabilized in the non-conducting state.

The duration of action of a local anesthetic is proportional to the time during which it is present at effective concentrations in contact with the nerve, or, more precisely, the ion channel(s). The effect of most currently used local anesthetics tends to be short-lived as a result of dissociation from and diffusion away from the intended site of action; therefore, repeated doses must be administered for a prolonged effect.

Undesired side effects of local anesthetics are largely a function of systemic concentrations of the drug resulting from such diffusion. These effects include paralysis of cardiac and smooth muscle systems, or undesired stimulation of the CNS. Because of these serious side effects, the quantity of drug administered must be carefully controlled.

Consequently, local anesthetic compounds having properties that allow effective concentrations to be maintained at the intended local site of action would be useful for prolonging the duration of action, thereby enhancing the clinical utility of local anesthetics in pain management and mitigating untoward toxic effects resulting from systemic concentration of the drug.

SUMMARY OF THE INVENTION

This invention provides novel multibinding compounds that are useful as inhibitors of voltage-gated $Na^+$ channels and are effective as local anesthetics. Accordingly, one aspect of this invention is directed to multibinding compounds of Formula I:

$$(L)_p(X)_q \qquad \qquad I$$

and pharmaceutically acceptable salts thereof;
wherein:
  each L is a ligand that may be the same or different at each occurrence;
  each X is a linker that may be the same or different at each occurrence;
  p is an integer of from 2 to 10; and
  q is an integer of from 1 to 20;
  wherein each of said ligands comprises a ligand domain capable of binding to a voltage-gated $Na^+$ channel of a cell.

Preferably q<p.

Preferably, each of said ligands is capable of inhibiting the generation and conduction of action potentials by said cell. More preferably, each of said ligands independently comprises a group of Formula (A):

$$Ar-W- \qquad \qquad (A)$$

wherein:
  Ar represents an aryl, heterocyclyl or heteroaryl group; and W is selected from a covalent bond, $—[CR^1R^2]_r—$, $—[CR^1R^2]_rC(O)—$, $—C(O)O[CR^1R^2]_r—$, $—OC(O)[CR^1R^2]_r—$, $—O—[CR^1R^2]_rC(O)—$, $—C(O)—NH—[CR^1R^2]_r—$, and $—NH—C(O)[CR^1R^2]_r$, where r is an integer of 0 to 10, and $R^1$ and $R^2$ are independently H, alkyl, substituted alkyl or a group $—NR^aR^b$, where $R^a$ and $R^b$ are both alkyl.

Preferably each divalent linker X is independently selected from a structure of:

(a) Formula II:

$$—N(R^3)—Z—N(R^4)— \qquad \qquad (II)$$

wherein:
  Z is alkylene, substituted alkylene, (alkylene O)$_w$-alkylene where w is an integer of 1 to 10, or alkenylene; and
  $R^3$ and $R^4$ are independently hydrogen, alkyl, substituted alkyl, aralkyl, a ligand, an X-ligand group, or $R^3$ and $R^4$ may independently form together with Z and the nitrogen atoms to which they are bound an N-containing heterocyclic ring optionally containing an additional 1 to 4 heteroatoms selected from O, S, $SO_2$, SO, and NR", where R" is a ligand, hydrogen, alkyl or substituted alkyl;

(b) Formula III:

$$—Y^a—Z'—Y^b— \qquad \qquad (III)$$

wherein:
  Z' is a heterocycle, aryl, heteroaryl, a crown compound having at least two unsubstituted ring nitrogens or a group —NR—, where R is alkyl;
  $Y^a$ and $Y^b$ are independently a covalent bond, alkylene, substituted alkylene, (alkylene-O)$_w$-alkylene where w is an integer of 1 to 10, or $—C(O)—(CH_2)_n—NR—$, where R is hydrogen or alkyl and n is an integer of 1 to 10;

(c) Formula IV:

$$—N^+(R^{3'})(R^7)—Z''—N^+(R^{4'})(R^8)— \qquad \qquad (IV)$$

wherein:
  Z" is alkylene or substituted alkylene; and
  $R^{3'}$, $R^{4'}$, $R^7$ and $R^8$ are independently alkyl, substituted alkyl, aralkyl, or a ligand, and optionally one of $R^7$ and $R^8$ is not present; and (d) Formula V:

$$—X'—Z'''—(Y'—Z''')_v—X'— \qquad \qquad (V)$$

wherein:
  v is an integer of 0 to 20;
  X' at each separate occurrence is independently alkylene, substituted alkylene, alkenylene, substituted alkenylene, alkynylene, substituted alkynylene, $—O—$, $—S—$, $—S(O)—$, $—S(O)_2—$, $—NR—$, $—N^+R R'—$, $—C(O)—$, $—C(O)O—$, $—C(O)NR—$, $—NRC(O)—$, $—C(S)—$, $—C(S)O—$, $—C(S)NR—$ or a covalent bond, where R and R' at each separate occurrence are independently as defined below for R' and R";
  Z''' is at each separate occurrence independently selected from alkylene, substituted alkylene, (alkylene-O)$_w$-alkylene where w is an integer of 1 to 10, alkylalkoxy, cycloalkylene, substituted cycloalkylene, alkenylene, substituted alkenylene, alkynylene, substituted alkynylene, cycloalkenylene, substituted cycloalkenylene, arylene, substituted arylene, heteroarylene, substituted heteroarylene, heterocyclene, substituted heterocyclene, crown compounds, or a covalent bond;
  Y' at each separate occurrence is independently selected from $—O—$, NR', S, $—C(O)—(CH_2)_n—NR'—$, $—NR'—(CH_2)_n C(O)—$, $—NR'—C(O)—NR'—$, $—O—C(O)—O—$, $—NR'—C(=NR')—$, $—C(=NR')—NR'—$, $—NR'C(O)—O—$, $—N=C(X')—NR'—$, $—P(O)_2(OR')—O—$, $—S(O)_n—CR'R''—$, $—S(O)_n—NR'—$, S—S— and a covalent bond; where n is 0, 1, or 2; and
  R, R' and R" at each separate occurrence are selected from hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

It is understood, of course, that trivalent linkers will have an additional linking point such as shown in FIG. 4.

Preferably, this invention is directed to multibinding compounds of Formula I, wherein p is an integer of from 2 to 4, and q is less than p. Most preferred are multibinding compounds having a structure selected from:

(a) Formula Ia

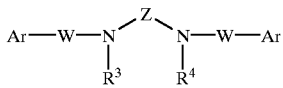
(Ia)

where Ar and W have the definitions provided above for formula A, and $R^3$, $R^4$ and Z have the meanings given in Formula II above;

(b) Formula Ib

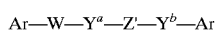
(Ib)

where Ar and W have the definitions provided above for formula A, and $Y^a$, $Y^b$ and Z' have the meanings given in Formula III above; and (c) Formula Ic

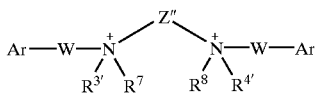
(Ic)

where Ar and W have the definitions provided above for formula A, and $R^{3'}$, $R^{4'}$, $R^7$, $R^8$ and Z" have the meanings given in Formula IV above.

In presently preferred embodiments, each ligand group Ar—W— is independently selected from:
2,6-dimethylphenyl-NH—C(O)—$CH_2$—;
2,6-dimethylphenyl-NH—C(O)—CH(($CH_2)_2CH_3$)—;
2,6-dimethylphenyl-NH—C(O)—;
(S)-2,6-dimethylphenyl-NH—C(O)—CH($CH_2CH_3$)—;
(R)-2,6-dimethylphenyl-NH—C(O)—CH($CH_2CH_3$)—;
o-tolyl-NH—C(O)—CH($CH_2CH_3$)—;
o-tolyl-NH—C(O)—CH($CH_3$)—;
o-tolyl-NH—C(O)—$CH_2$—;
4-[—C(O)—O—$(CH_2)_2$—N($CH_2CH_3)_2$]-phenyl-;
4-[—C(O)—NH—$(CH_2)_2$—N($CH_2CH_3)_2$]-phenyl-;
4-[—C(O)—NH($CH_3$)]-phenyl-;
4-[—C(O)—O—$(CH_2)_2$—N($CH_3)_2$]-phenyl-;
4-[—C(O)—O—$CH_2CH_3$]-2,6-dimethylphenyl-NH—C(O)—$CH_2$—;
4-[—C(O)—O—$CH_3$]-2,6-dimethylphenyl-NH—C(O)—CH($CH_2CH_3$)—;
4-[—C(O)—O—$CH_3$]-2-methylphenyl-NH—C(O)—CH($CH_2CH_3$)—;
4-[C(O)—O—$CH_3$]-2,6-dimethylphenyl-NH—C(O)—CH($CH_2CH_3$)—;
4-aminophenyl-C(O)—;
4-butylaminophenyl-C(O)—;
2,6-dimethylphenyl-O—C(O)—$CH_2$—;
phenyl-$(CH_2)_3$—;
phenyl-C(O)—$(CH_2)_2$—;
4-[—NH—C(O)—$CH_2$—N($CH_2CH_3)_2$]-3,5-dimethylphenyl-O—$CH_2$—C(O)—;
4-aminophenyl-C(O)—O—$(CH_2)_2$—;
4-methoxyphenyl-NH—C(O)—$CH_2$—;
2-methylphenyl-NH—C(O)—$CH_2$—;
phenyl-NH—C(O)—$CH_2$—;
4-chlorophenyl-NH—C(O)—$CH_2$—;
2-methyl-4-methoxyphenyl-NH—C(O)—$CH_2$—;
2-methyl-4-chlorophenyl-NH—C(O)—$CH_2$—;
2-methylphenyl-NH—C(O)—CH($CH_3$)—;
2-methylphenyl-NH—C(O)—CH($CH_2CH_3$)—;
phenyl-$(CH_2)_2$—C(O)—;
4-nitrophenyl-C(O)—O—$(CH_2)_2$—;
2-chloro-4-nitrophenyl-C(O)—O—$(CH_2)_2$—;
(S)-2,6-dimethylphenyl-NH—C(O)—CH(N($CH_3)_2$)—;
(R)-2,6-dimethylphenyl-NH—C(O)—CH(N($CH_3)_2$)—;
(S)-2,6-dimethylphenyl-NH—C(O)—CH(N($CH_2CH_3)_2$)—;
(R)-2,6-dimethylphenyl-NH—C(O)—CH(N($CH_2CH_3)_2$)—;
4-{O-[($CH_2)_n$—C(O)—O$]_m$R}-2,6-dimethylphenyl-NH—C(O)—CHR'—, where n is an integer equal to 1 to 6, m is 0 or 1, R is $C_1$–$C_6$ alkyl, and R' is H or alkyl;
2-ethyl-6-methylphenyl-NH—C(O)—CH($CH_2CH_3$)—;
2,4,6-trimethylphenyl-CH($CH_2CH_3$)—C(O)—NH—; and
2-ethyl-6-methylphenyl-NH—C(O)—$CH_2$—.

Preferred multibinding compounds of this invention include by way of example compounds listed in Table 2 (Preferred Embodiments).

Another aspect of the invention is directed to a pharmaceutical composition comprising a pharmaceutically acceptable excipient and a therapeutically effective amount of one or more multibinding compounds represented by Formula I, $$(L)_p(X)_q \qquad I$$

and pharmaceutically acceptable salts thereof;
wherein:
each L is a ligand that may be the same or different at each occurrence;
each X is a linker that may be the same or different at each occurrence;
p is an integer of from 2 to 10; and
q is an integer of from 1 to 20;
wherein each of said ligands comprises a ligand domain capable of binding to a voltage-gated $Na^+$ channel of a cell in a mammal, thereby inhibiting the generation and conduction of action potentials by said cell and modulating the diseases and conditions resulting therefrom.

Such compositions are particularly useful for producing local anesthesia in a mammal whereby the multibinding compounds act upon voltage-gated $Na^+$ channels of a nerve and thereby interrupt nerve conduction.

Preferably, the pharmaceutical compositions of this invention comprise one or more multibinding compounds of Formula I, wherein p is an integer of from 2 to 4, and q is less than p. Most preferably, such compositions comprise bivalent multibinding compounds of Formulas Ia, Ib and Ic.

In one of its methods aspects, this invention is directed to a method of preparing a multibinding compound represented by formula I:

$$(L)_p(X)_q \qquad I$$

wherein
each L is a ligand that may be the same or different at each occurrence;
X is a linker that may be the same or different at each occurrence;

p is an integer of from 2 to 10; and q is an integer of from 1 to 20;

wherein each of said ligands comprises a ligand domain capable of binding to a voltage-gated $Na^+$ channel of a cell, said method comprising:

(a) providing at least p equivalents of a ligand L or precursors thereof and at least q equivalents of linker or linkers X; and (b) covalently attaching said ligands to said linkers to produce a multibinding compound; or (b') covalently attaching said ligand precursors to said linkers and completing the synthesis of said ligands thereupon, thereby to produce a multibinding compound. Preferably, p is an integer of from 2 to 4, and q is less than p. Most preferably, p is equal to 2.

Another aspect of the invention is directed to a method for producing local anesthesia in a mammal, which method comprises administering to a mammal in need of such treatment a therapeutically effective amount of a pharmaceutical composition comprising a pharmaceutically acceptable excipient and one or more multibinding compounds represented by formula I,

$(L)_p(X)_q$        (I)

and pharmaceutically acceptable salts thereof, wherein each L is a ligand that may be the same or different at each occurrence;

X is a linker that may be the same or different at each occurrence;

p is an integer of from 2 to 10; and q is an integer of from 1 to 20;

wherein each of said ligands comprises a ligand domain capable of binding to a voltage-gated $Na^+$ channel of a cell mediating the conduction of nerve impulses in a mammal, thereby blocking the conduction of said impulses and producing local anesthesia.

A preferred embodiment is the use of pharmaceutical compositions comprising bivalent compounds of Formulas Ia, Ib and Ic and their pharmaceutically acceptable salts to produce local anesthesia of long duration (i.e., from about 6 hours to about 36 hours). In particularly preferred embodiments, these compositions have greatly attenuated or negligible systemic toxicity relative to conventional monovalent (i.e., unlinked) anesthetics.

A. phenyldiacetylene core structure

Figure 1A:
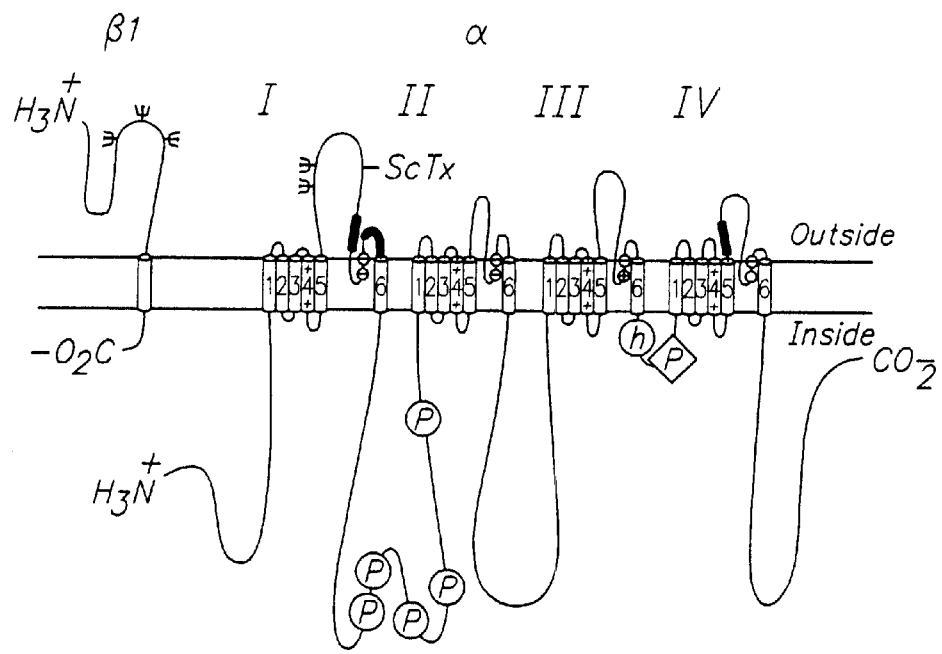
FIG. 1A depicts a highly schematic illustration of the transmembrane topology of the voltage-gated $Na^+$ channel ($\beta_2$ subunit not shown). Tetrodotoxin binding residues are indicated by small circles between transmembrane segments 5 and 6; scorpion α-toxin binding sites are indicated by the black rectangles on the lines connecting transmembrane segments 5 and 6 (domains I and IV) and by ScTx.
Figure 1B:
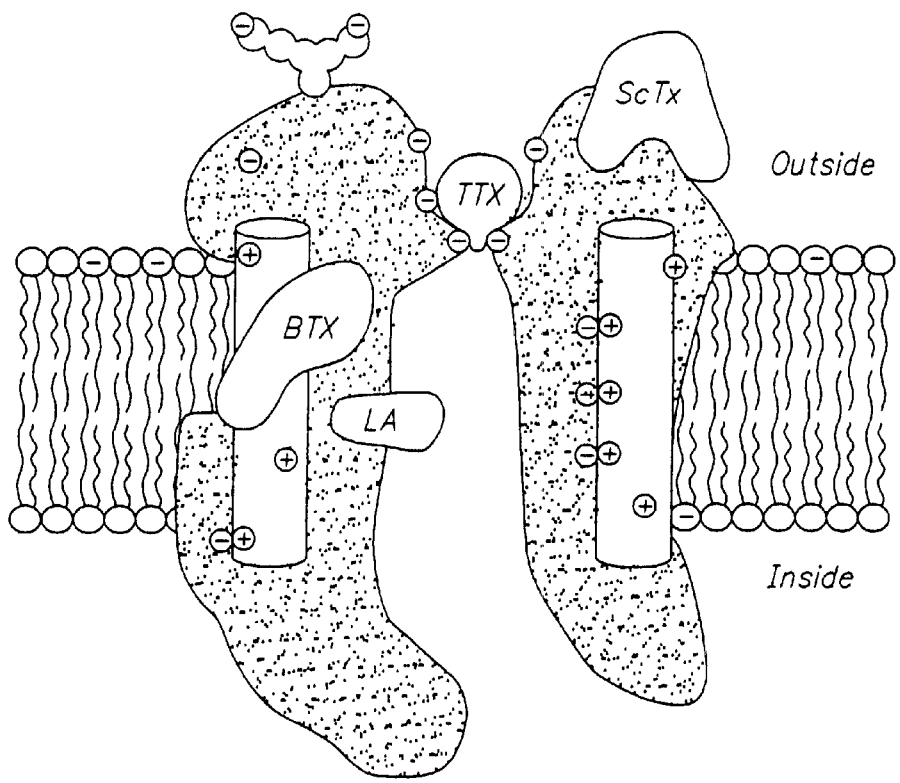
FIG. 1B depicts a diagrammatic representation of the $Na^+$ channel illustrating generally the binding sites for neurotoxins and local anesthetics.

B. cyclohexane dicarboxylic acid core structure.

FIGS. 6–14 depict Reaction Schemes A–T, which illustrate reactions for preparing the multibinding compounds of this invention.

DETAILED DESCRIPTION OF THE INVENTION

Biological systems, in general, are controlled by molecular interactions between bioactive ligands and their receptors, in which the receptor "recognizes" a molecule or a portion thereof (i.e., a ligand domain) to produce a biological effect. The voltage-gated $Na^+$ channels can be considered to be pharmacological receptors: they possess specific binding sites for ligands having antagonist activities; the binding of ligands to such sites modulates $Na^+$ flux through the channel; and the channel properties are regulatable. Accordingly, diseases or conditions that involve, or are mediated by, $Na^+$ channels can be treated with pharmacologically active ligands that interact with such channels to initiate, modulate or abrogate transport activity.

The interaction of a $Na^+$ channel and a $Na^+$ channel-binding ligand may be described in terms of "affinity" and "specificity". The "affinity" and "specificity" of any given ligand-$Na^+$ channel interaction is dependent upon the complementarity of molecular binding surfaces and the energetic consequences of complexation (i.e., the net difference in free energy $\Delta G$ between bound and free states). Affinity may be quantified by the equilibrium constant of complex formation, the ratio of on/off rate constants, and/or by the free energy of complex formation. Specificity relates to the difference in binding affinity of a ligand for different receptors.

The net free energy of interaction of a ligand with a $Na^+$ channel is the difference between energetic gains (enthalpy gained through molecular complementarity and entropy gained through the hydrophobic effect) and energetic costs (enthalpy lost through decreased solvation and entropy lost through reduced translational, rotational and conformational degrees of freedom).

The compounds of this invention preferably comprise 2 to 10 $Na^+$ channel-binding ligands covalently linked together and capable of acting as multibinding agents. Without wishing to be bound by theory, the surprising activity of these compounds is believed to arise at least in part from their ability to bind in a multivalent manner with the $Na^+$ channel, which gives rise to a more favorable net free energy of binding. Multivalent binding interactions are characterized by the concurrent interaction of at least two ligands of a multibinding compound with multiple ligand binding sites on a receptor or receptors. Multivalent interactions differ from collections of individual monovalent interactions by being capable of providing enhanced biologic and/or therapeutic effect. Multivalent binding can amplify binding affinities and differences in binding affinities, resulting in enhanced binding specificity as well as affinity.

Definitions

As used herein:

The term "alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated.

The term "substituted alkyl" refers to an alkyl group as defined above having from 1 to 5 substituents selected from the group consisting of alkoxy, substituted alkoxy, cycloalkyl, substituted cycloalkyl, cycloalkenyl, substituted cycloalkenyl, acyl, acylarnino, acyloxy, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkylene" refers to a diradical of a branched or unbranched saturated hydrocarbon chain, preferably having from 1 to 40 carbon atoms, more preferably 1 to 10 carbon atoms, even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "substituted alkylene" refers to:

(1) an alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocylooxy, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group;

(2) an alkylene group as defined above that is interrupted by 1–20 atoms independently chosen from oxygen, sulfur and NR$^a$—, where R$^a$ is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; and (3) an alkylene group as defined above that has both from 1 to 5 substituents as defined above and is also interrupted by 1 to 20 atoms as defined above. Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "alkaryl" or "aralkyl" refers to the groups -alkylene-aryl and substituted alkylene-aryl in which alkylene, substituted alkylene and aryl are as defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Examples of such groups are methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

"Alkenyl" refers to a monoradical of a branched or unbranched unsaturated hydrocarbon preferably having from 2 to 40 carbon atoms, more preferably 2 to 10 carbon atoms, even more preferably 2 to 6 carbon atoms, and preferably having 1 to 6 double bonds. This term is further exemplified by such radicals as vinyl, prop-2-enyl, pent-3-enyl, hex-5-enyl, 5-ethyldodec-3,6-dienyl, and the like.

The term "substituted alkenyl" refers to an alkenyl group as defined above having from 1 to 5 substituents selected from the group consisting of alkoxy, substituted alkoxy, acyl, acylamino, acyloxy, aminoacyl, aminoacyloxy, oxyaminoacyl, azido, cyano, halogen, hydroxyl, keto, thioketo, carboxyl, carboxylalkyl, thiol, thioalkoxy, substituted thioalkoxy, aryl, heteroaryl, heterocyclic, aryloxy, thioaryloxy, heteroaryloxy, thioheteroaryloxy, heterocyclooxy, thioheterocylooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkenylene" refers to a diradical of an unsaturated hydrocarbon, preferably having from 2 to 40 carbon atoms, more preferably 2 to 10 carbon atoms, even more preferably 2 to 6 carbon atoms, and preferably having 1 to 6 double bonds. This term is further exemplified by such radicals as 1,2-ethenyl, 1,3-prop-2-enyl, 1,5-pent-3-enyl, 1,4-hex-5-enyl, 5-ethyl-1,12-dodec-3,6-dienyl, and the like.

The term "substituted alkenylene" refers to an alkenylene group as defined above having from 1 to 5 substituents, selected from the group consisting of alkoxy, substituted alkoxy, acyl, acylamino, acyloxy, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and $NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

"Alkynyl" refers to a monoradical of an unsaturated hydrocarbon, preferably having from 2 to 40 carbon atoms, more preferably 2 to 10 carbon atoms, even more preferably 2 to 6 carbon atoms, and preferably having 1 to 6 triple bonds. This term is further exemplified by such radicals as acetylenyl, prop-2-ynyl, pent-3-ynyl, hex-5-ynyl, 5-ethyldodec-3,6-diynyl, and the like.

The term "substituted alkynyl" refers to an alkynyl group as defined above having from 1 to 5 substituents, selected from the group consisting of alkoxy, substituted alkoxy, acyl, acylamino, acyloxy, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocycloxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, SO$_2$-heterocyclic, $NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic.

"Alkynylene" refers to a diradical of an unsaturated hydrocarbon radical, preferably having from 2 to 40 carbon atoms, more preferably 2 to 10 carbon atoms, even more preferably 2 to 6 carbon atoms, and preferably having 1 to 6 triple bonds. This term is further exemplified by such radicals as 1,3-prop-2-ynyl, 1,5-pent-3-ynyl, 1,4-hex-5-ynyl, 5-ethyl-1,12-dodec-3,6-diynyl, and the like.

The term "acyl" refers to the groups —CHO, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined-herein.

The term "acylamino" refers to the group —C(O)NRR where each R is independently hydrogen, alkyl, substituted alkyl, aryl, heteroaryl, heterocyclic or where both R groups are joined to form a heterocyclic group (e.g., morpholine) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g , phenyl) or multiple condensed (fused) rings (e.g., naphthyl or anthryl).

Unless otherwise constrained by the definition for the aryl substituent, such aryl groups can optionally be substituted with from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, $NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to a diradical derived from aryl or substituted aryl as defined above, and is exemplified by 1,2-phenylene, 1,3-phenylene, 1,4-phenylene, 1,2-naphthylene and the like.

The term "substituted arylene" refers to a diradical derived from aryl as defined above having from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, $NR_aR_b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic. Preferred arylene substituents include alkyl, alkoxy, halo, cyano, nitro, trihalomethyl, and thioalkoxy.

The term "carboxyalkyl" refers to the group "—C(O)Oalkyl" where alkyl is as defined above.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents selected from the group consisting of alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkylene" refers to a diradical derived from cycloalkyl or substituted cycloalkyl as defined above.

The term "substituted cycloalkylene" refers to a diradical derived from cycloalkyl as defined above having from 1 to 5 substituents selected from the group consisting of alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkenyl" refers to cyclic alkenyl groups of from 4 to 20 carbon atoms having a single cyclic ring or fused rings and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkenylene" refers to a diradical derived from cycloalkenyl or substituted cycloalkenyl as defined above.

The term "substituted cycloalkenylene" refers to a diradical derived from cycloalkenyl as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, azido, cyano, halogen, hydroxyl, keto. thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "halo" or "halogen" refers to fluoro, chloro, bromo and iodo.

"Haloalkyl" refers to alkyl as defined above substituted by 1 to 4 halo groups as defined above, which may be the same or different, such as trifluoromethyl, 3-fluorododecyl, 12,12,12-trifluorododecyl, 2-bromooctyl, -3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, mono-and di-alkylamino, mono- and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred heteroaryls include pyridyl, pyrrolyl and furyl.

The term "heteroaryloxy" refers to the group heteroaryl-O—.

The term "heteroarylene" refers to the diradical group derived from heteroaryl or substituted heteroaryl as defined above, and is exemplified by the groups 2,6-pyridylene, 2,4-pyridiylene, 1,2-quinolinylene, 1,8-quinolinylene, 1,4-benzofuranylene, 2,5-pyridinylene, 1,3-morpholinylene, 2,5-indolenyl, and the like.

The term "heterocycle" or "heterocyclic" refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Such heterocyclic groups can have a single ring or multiple condensed rings.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

A preferred class of heterocyclics include "crown compounds" which refers to a specific class of heterocyclic compounds having one or more repeating units of the formula [—(CH$_2$—)$_m$Y—] where m is equal to or greater than 2, and Y at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 3 to 10 heteroatoms and 8 to 40 carbon atoms.

The term "heterocyclooxy" refers to the group heterocyclic-O—.

The term "thioheterocyclooxy" refers to the group heterocyclic-S—.

The term "heterocyclene" refers to the diradical group derived from a heterocycle as defined herein, and is exemplified by the groups 2,6-morpholino, 2,5-morpholino and the like.

The term "substituted heterocyclene" refers to a diradical group derived from a heterocycle as defined herein having 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, aminoacyl, aminoacyloxy, oxyaminoacyl, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, -SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Such heterocyclic groups can have a single ring or multiple condensed rings.

The term "oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Heteroarylalkyl" refers to heteroaryl as defined above linked to alkyl as defined above, for example pyrid-2-ylmethyl, 8-quinolinylpropyl, and the like.

"Optional" or "optionally" means that the subsequently described event or circumstance may or may not occur, and that the description includes instances where said event or circumstance occurs and instances in which it does not. For example, optionally substituted alkyl means that alkyl may or may not be substituted by those groups enumerated in the definition of substituted alkyl.

The term "pharmaceutically acceptable salt" refers to salts which retain the biological effectiveness and properties of the multi-binding compounds of this invention and which are not biologically or otherwise undesirable. In many cases, the multi-binding compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thiol, amino or carboxyl group. See, generally, T. W. Greene & P. G. M. Wuts "Protective Groups in Organic Synthesis," $2^{nd}$ Ed, 1991, John Wiley and Sons, N.Y.

The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product. Preferred carboxyl protecting groups include esters such as methyl, ethyl, propyl, t-butyl etc. which can be removed by hydrolysis conditions compatible with the nature of the product.

As used herein, the terms "inert organic solvent" or "inert solvent" mean a solvent inert under the conditions of the reaction being described in conjunction therewith including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The term "Na$^+$ channel" or "sodium ion channel" refers to a biomembrane-associated structure that is capable of transporting sodium ions across a lipid membrane. The sodium channels pertinent to this invention are voltage-gated channels that mediate action potentials in mediate action potentials in excitable tissues (e.g., nerve and muscle).

Figure 2:
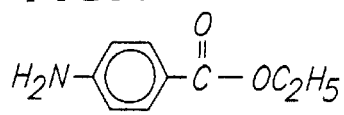
FIG. 2 shows representative clinically used local anesthetics agents.
Figure 2:
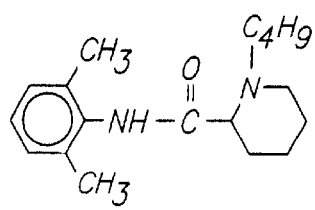
Figure 2:
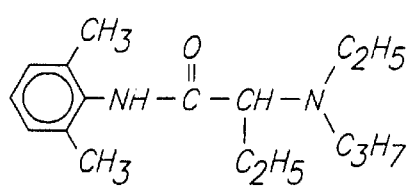
Figure 2:
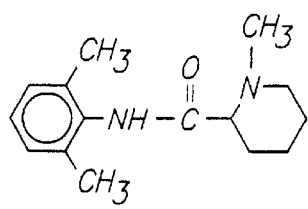
Figure 2:
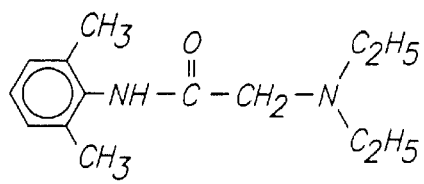
Figure 2:
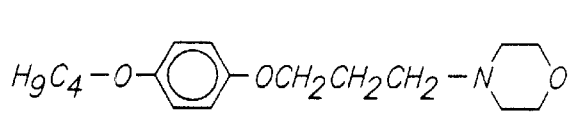
Figure 2:
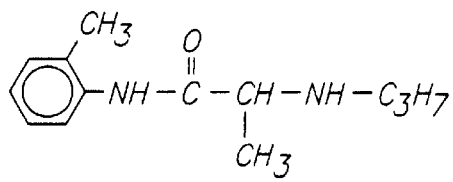
Figure 2:
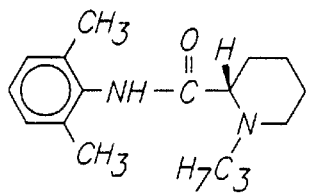
Figure 2:
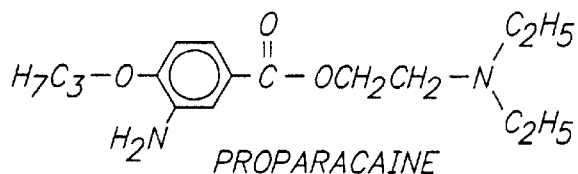
Figure 2:
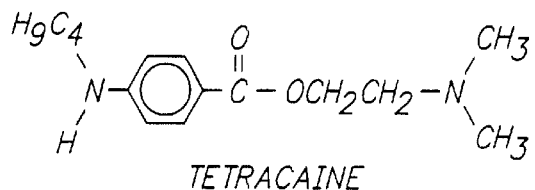

"Ligand" as used herein denotes a compound that is a binding partner for a receptor (e.g., a voltage-gated sodium ion channel). The specific region or regions of the ligand molecule that is recognized by the ligand binding site of the receptor is designated as the "ligand domain". A ligand may be either capable of binding to a receptor by itself, or may require the presence of one or more non-ligand components for binding (e.g. ions, a lipid molecule, a solvent molecule, and the like). Examples of ligands that are useful in this invention include, but are not limited, to lidocaine, bupivacaine, benzocaine, levobupivacaine, etidocaine, mepivacaine, prilocaine, ropivacaine, tetracaine, procaine, procainamide, dibucaine, alphabutyl lidocaine, proparacaine, 2-chloroprocaine and pramoxine. The structures of representative local anesthetic agents is shown in FIG. 2.

It should be understood that the ligands in multibinding compounds of this invention comprise a ligand group Ar—W (as defined in the Summary of the Invention) and an amine group. These features are indicated in the structures below by the bold underline. In some embodiments (exemplified by structure (1) below), the amine group is distinct from the linker.

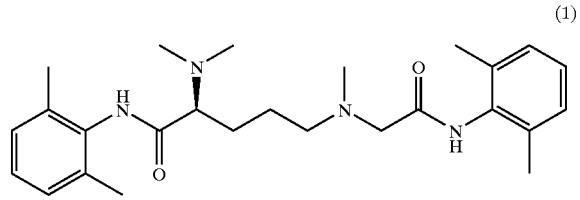

(1)

In other embodiments, the amine group is provided by the linker (exemplified by structure (2) below).

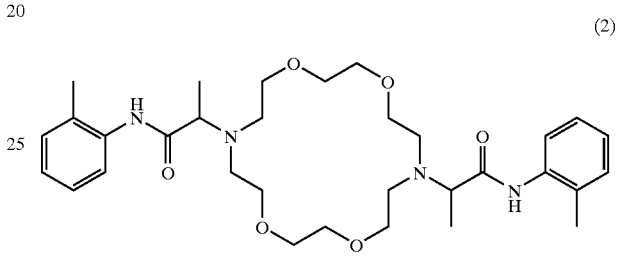

(2)

For purposes of the present invention, it should also be recognized that portions of the ligand structure that are not essential for specific molecular recognition and binding activity may be varied substantially, replaced with unrelated structures and, in some cases, omitted entirely without affecting the binding interaction. It is further understood that the term ligand is not intended to be limited to compounds known to be useful, for example, as sodium ion channel-binding compounds (i.e., known drugs). Those skilled in the art will understand that the term ligand can equally apply to a molecule that is not normally recognized for its channel binding properties. The primary requirement for a ligand as defined herein is that it has a ligand domain, as defined above, which is available for binding to a recognition site on a receptor (e.g., a voltage-gated sodium ion channel). In addition, it should be noted that ligands that exhibit marginal activity or lack useful activity as monomers can be highly active as multibinding compounds, because of the biological benefit conferred by multivalency.

The term "ligand" or "ligands" as used herein is intended to include the racemic forms of the ligands as well as individual enantiomers and diastereomers and non-racemic mixtures thereof.

The term "ligand precursor" refers to a compound that is a starting material or an intermediate in the synthesis of a completed ligand. The ligand precursor may be coupled to a linker with completion of ligand synthesis being carried out in a separate step (see, e.g., Scheme T of FIG. 14). Another example is provided in Scheme R of FIG. 12, wherein compound (e) having an R group —CH$_2$COOH is a ligand precursor in the synthesis of compound 145 and other compounds of Formula Ia where R is carboxyalkyl-substituted methylene.

"Multibinding agent" or "multibinding compound" refers to a compound that is capable of multivalency as defined below, and which has from 2 to 10 ligands covalently bound to one or more linkers. In all cases, each ligand and linker in the multibinding agent is independently selected such that the multibinding agents include both symmetric compounds (i.e., where each ligand is identical as well as each linker) and asymmetric compounds (i.e., where at least one ligand is different from he other ligand and/or at least one linker is different from other linkers). The multibinding agent provides a biologic and/or therapeutic effect greater than the aggregate of unlinked ligands equivalent thereto. That is to say, that the biologic and/or therapeutic effect of the ligands attached to the multi-binding compound is greater than that achieved by the same number of unlinked ligands made available for binding to the receptor or receptors. Examples of greater "biologic and/or therapeutic effect" include increased ligand-receptor binding interactions (e.g., increased affinity; increased agonist, antagonist or modulatory effects; improved kinetics), increased selectivity for the target, increased potency, increased efficacy, decreased toxicity, increased duration of action, altered bioavailability, improved pharmacokinetics, improved activity spectrum, increased therapeutic index, and the like. The multibinding compounds of this invention will exhibit at least one, and preferably more than one, of the above-mentioned effects.

The term "ligand binding site" as used herein denotes a site on a receptor, such as a $Na^+$ channel, that recognizes a ligand domain and provides a binding partner for the ligand. The ligand binding site may be defined by monomeric or multimeric structures. This interaction may be capable of producing a unique biological effect, for example agonism, antagonism, modulation, or may maintain an ongoing biological event, and the like.

It should be recognized that the ligand binding sites of $Na^+$ channels that participate in biological multivalent binding interactions are constrained to varying degrees by their intra- and intermolecular associations. For example, ligand binding sites may be covalently joined in a single structure, noncovalently associated in one or more multimeric structures, embedded in a membrane or biopolymer matrix, and so on, and therefore have less translational and rotational freedom than if the same sites were present as monomers in solution.

The terms "agonism" and "antagonism" are well known in the art. As used herein, the term "agonist" refers to a ligand that when bound to a voltage-gated $Na^+$ channel stimulates its activity. The term "antagonist" refers to a ligand that when bound to a voltage-gated $Na^+$ channel inhibits its activity. One skilled in the art will appreciate that the term "agonist" encompasses both full and partial agonists, the difference being that a partial agonist has a low efficacy relative to a full agonist.

Channel block or activation may result from allosteric effects of ligand binding to the channel rather than occupancy of the channel pore. These allosteric effects may produce changes in protein conformation that affect $Na^+$ binding sites, gating mechanisms and/or the pore region (i.e., ion permeation).

A $Na^+$ channel can exist in several states: C (closed resting state); O (open state); and I (inactivated state). The probability that a channel will exist in one of these three states changes with voltage. A given ligand may have different binding affinities for different states, and thereby be capable of producing agonist or antagonist activity or tonic or phasic block (see, generally, Strichartz, Chapter 2 In: *Neural Blockade in Clinical Anesthesia and Management of Pain,* Third Edition (Eds. M J Cousins and P. O. Bridenbaugh, Lippincott-Raben Publishers, 1998).

The term "modulatory effect" is intended to refer to the ability of a ligand to change the activity of a $Na^+$ channel through binding to the channel.

"Potency" as used herein refers to the minimum concentration at which a ligand is able to achieve a desirable biological or therapeutic effect. The potency of a ligand is typically proportional to its affinity for its receptor. In some cases, the potency may be non-linearly correlated with its affinity. In comparing the potency of two drugs, e.g., a multi-binding agent and the aggregate of its unlinked ligand, the dose-response curve of each is determined under identical test conditions (e.g. in an in vitro or in vivo assay, in an appropriate animal model (such as a human patient)). The finding that the multi-binding agent produces an equivalent biologic or therapeutic effect at a lower concentration than the aggregate unlinked ligand (e.g. on a per weight, per mole or per ligand basis) is indicative of enhanced potency.

"Univalency" as used herein refers to a single binding interaction between one ligand with one ligand binding site as defined herein. It should be noted that a compound having multiple copies of a ligand (or ligands) exhibits univalency when only one ligand of that compound interacts with a ligand binding site. Examples of univalent interactions are depicted below.

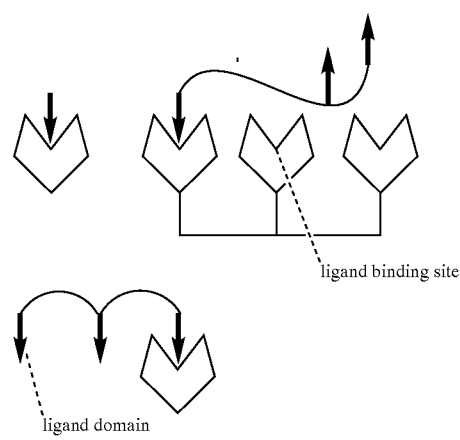

"Multivalency" as used herein refers to the concurrent binding of from 2 to 10 linked ligands (which may be the same or different) and two or more corresponding ligand binding sites, which may be the same or different. An example of trivalent binding is depicted below for illustrative purposes.

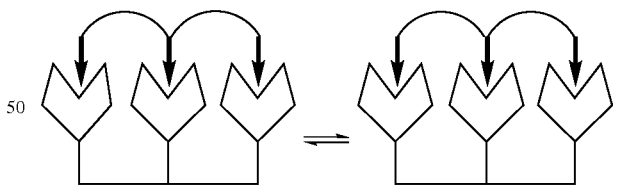

It should be understood that not all compounds that contain multiple copies of a ligand attached to a linker necessarily exhibit the phenomena of multivalency, i.e., that the biologic and/or therapeutic effect of the multi-binding agent is greater than that of the same number of unlinked ligands made available for binding to the receptor or receptors. For multi-valency to occur, the ligands that are connected by a linker or linkers have to be presented to their receptors by the linker(s) in a specific manner in order to bring about the desired ligand-orienting result, and thus produce a multi-binding interaction.

"Selectivity" or "specificity" is a measure of the binding preferences of a ligand for different receptors. The selectivity of a ligand with respect to its target receptor relative to another receptor is given by the ratio of the respective values of $K_d$ (i.e., the dissociation constants for each ligand-receptor complex) or, in cases where a biological effect is observed below the $K_d$, the ratio of the respective $EC_{50}$s (i.e., the concentrations that produce 50% of the maximum response for the ligand interacting with the two distinct receptors).

The term "treatment" refers to any treatment of a disease or condition in a mammal, particularly a human, and includes:

(i) preventing the disease or condition from occurring in a subject which may be predisposed to the condition but has not yet been diagnosed with the condition and, accordingly, the treatment constitutes prophylactic treatment for the pathologic condition;

(ii) inhibiting the disease or condition, i.e., arresting its development;

(iii) relieving the disease or condition, i.e., causing regression of the disease or condition; or (iv) relieving the symptoms resulting from the disease or condition, e.g., relieving pain without addressing the underlying disease or condition.

The term "disease or condition which is modulated by treatment with a local anesthetic" covers all disease states and/or conditions associated with pain sensation that are generally acknowledged in the art to be usefully treated with a local anesthetic ligand and those disease states and/or conditions that have been found to be usefully treated by a specific multibinding local anesthetic compound of our invention, i.e., the compounds of Formula I. Such disease states and conditions include, by way of example only, surgical anesthesia, post operative pain relief, post-arthroscopic pain management, long-duration surgical block, proctitis and active distal ulcerative colitis, and the like.

The term "therapeutically effective amount" refers to that amount of multi-binding compound that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable excipient" is intended to include vehicles and carriers capable of being coadministered with a multi-binding compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present invention.

The term "linker", identified where appropriate by the symbol X, refers to a group or groups that covalently links from 2 to 10 ligands (as defined above) in a manner that provides for a compound capable of multivalent interactions with voltage-gated $Na^+$ channels. Among other features, the linker is a ligand-orienting entity that permits attachment of multiple copies of a ligand (which may be the same or different) thereto. In some cases, the linker may itself be biologically active. The term "linker" does not, however, cover solid inert supports such as beads, glass particles, rods, and the like, but it is to be understood that the multi-binding compounds of this invention can be attached to a solid support if desired, for example, for use in separation and purification processes and for similar applications.

The extent to which multivalent binding is realized depends upon the efficiency with which the linker or linkers that joins the ligands presents them to their array of ligand binding sites. Beyond presenting these ligands for multivalent interactions with ligand binding sites, the linker spatially constrains these interactions to occur within dimensions defined by the linker. Thus the structural features of the linker (valency, geometry, orientation, size, flexibility, chemical composition) are features of multi-binding compounds that play an important role in determining their molecular interactions with receptors and efficacy.

The linkers used in this invention are selected to allow multivalent binding of ligands to any desired ligand binding sites of a voltage-gated $Na^+$ channel, whether such sites are located interiorly (e.g., within a channel/translocation pore), both interiorly and on the periphery of a channel, at the boundary region between the lipid bilayer and the channel, or at any intermediate position thereof. The distance between the nearest neighboring ligand domains is preferably in the range of about 2 Å to about 100 Å, more preferably in the range of about 2 Å to about 50 Å and even more preferably about 4–15 Å.

The ligands are covalently attached to the linker or linkers using conventional chemical techniques. The reaction chemistries resulting in such linkage are well known in the art and involve the use of reactive functional groups present on the linker and ligand. Preferably, the reactive functional groups on the linker are selected relative to the functional groups available on the ligand for binding or which can be introduced onto the ligand for binding. Again, such reactive functional groups are well known in the art. For example, reaction between a carboxylic acid of either the linker or the ligand and a primary or secondary amine of the ligand or the linker in the presence of suitable well-known activating agents results in formation of an amide bond covalently linking the ligand to the linker; reaction between an amine group of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalently linking the ligand to the linker.

Table 1 illustrates numerous reactive functional groups and the resulting bonds formed by reaction therebetween. Where functional groups are lacking, they can be created by suitable chemistries that are described in standard organic chemistry texts such as J March, "Advanced Organic Chemistry", 4th Edition, (Wiley-Interscience (New York), 1992.

TABLE 1

Attachment Chemistries

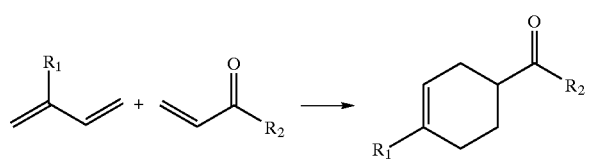

TABLE 1-continued

Attachment Chemistries

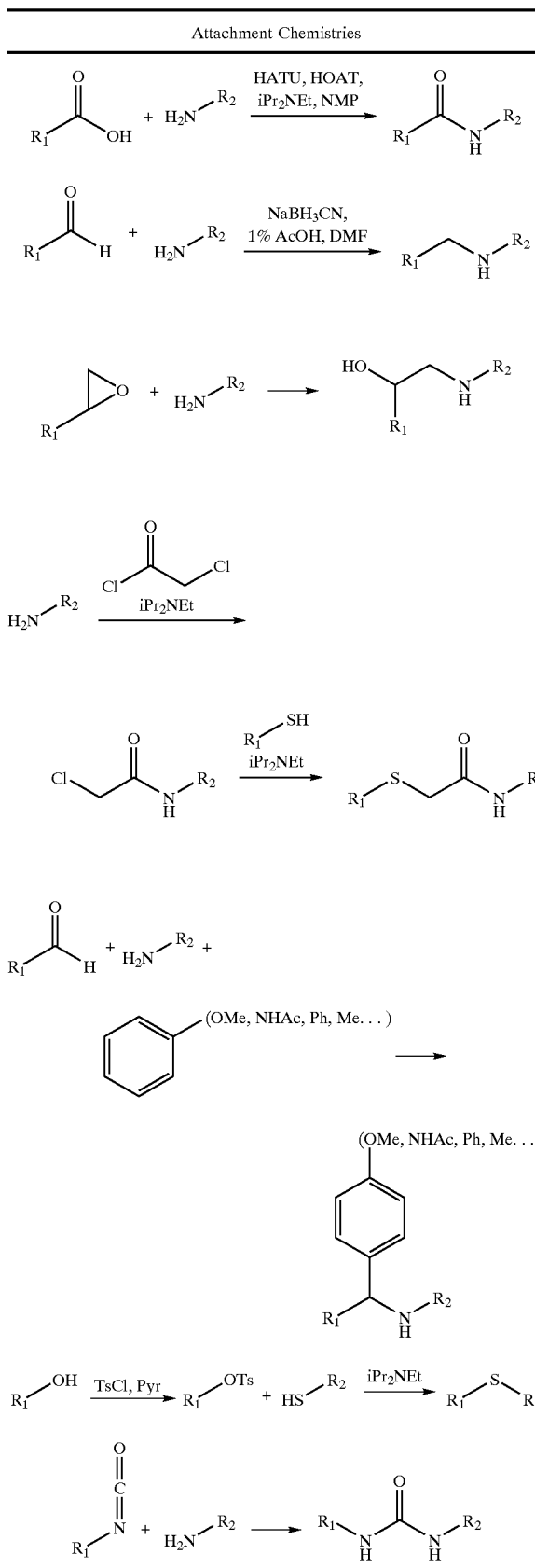

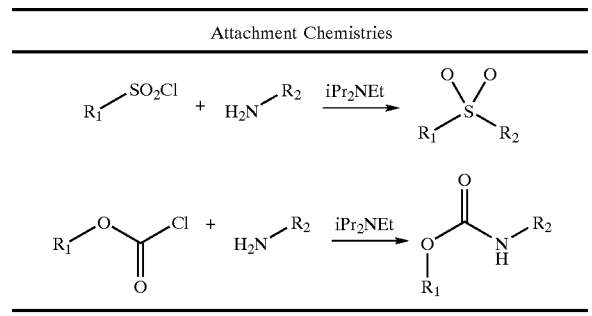

The linker is attached to the ligand at a position that retains ligand domain-receptor binding and specifically permits the ligand domain of the ligand to orient itself to bind to the ligand binding site. The determination of where acceptable substitutions can be made on a ligand is typically based on prior knowledge of structure-activity relationships of the ligand and/or congeners and/or structural information about ligand-receptor complexes (e.g., X-ray crystallography, NMR, and the like). Such positions and synthetic protocols for linkage are well known in the art and can be determined by those with ordinary skill in the art. For example, the arrows below indicate the possible positions for attachment of lidocaine to a linker.

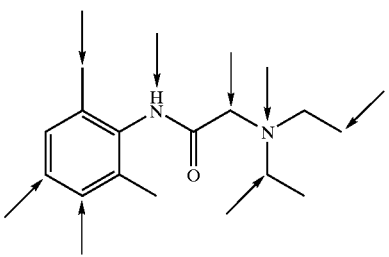

Following attachment of a ligand to the linker or a significant portion thereof (e.g., 2–10 atoms of linker), the linker-ligand conjugate may be tested for retention of activity in a relevant assay system (see Testing and Examples, below, for representative assays).

The relative orientation in which the ligand domains are displayed to the receptors depends both on the particular point (or points) of attachment of the ligands to the linker, and on the geometry of the linker framework. The term linker embraces everything that is not considered to be part of the ligand, e.g., ancillary groups such as solubilizing groups, lipophilic groups, groups that alter pharmacodynamics or pharmacokinetics, groups that modify the diffusability of the multi-binding compound, groups that attach the ligand to the linker, groups that aid the ligand-orienting function of the linker, for example, by imparting flexibility or rigidity to the linker as a whole, or to a portion thereof, and so on.

Nomenclature

The naming of the compounds of the present invention is illustrated below for representative compounds of formula (I).

For example, in the following compound of formula (I), compound 54 in Table 2 below (see Preferred Embodiments),

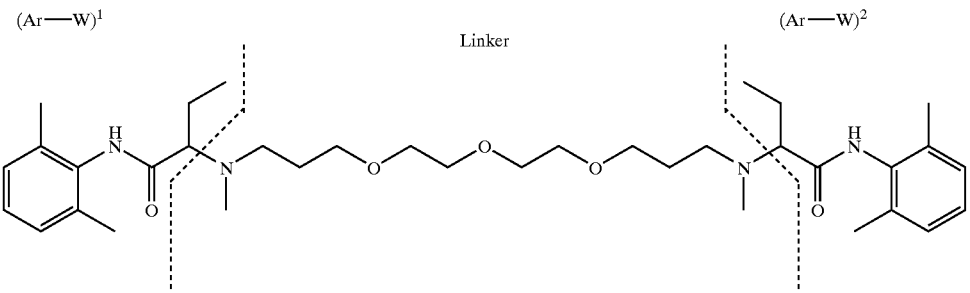

the ligand groups (Ar—W)¹ and (Ar—W)² are both named 2,6-dimethylphenyl-NH—C(O)—CH(CH$_2$CH$_3$)— and the linker is denoted by its chemical formula, —N(CH$_3$)—(CH$_2$)$_3$—O—(CH$_2$)$_2$—O—(CH$_2$)$_2$—O—(CH$_2$)$_3$—N(CH$_3$)—. The aryl ring substituents are numbered such that position 1 is the position of attachment of the linker to the ring.

In some instances, the ligand groups, (Ar—W)¹ and (Ar—W)² and the linkers are named according to IUPAC rules, using the Autonom® software program (Beilstein). Thus for example, in the compound shown above, the ligand groups are both named N-(2,6-dimethyl-phenyl)-butyramide and the linker is named methyl-(3-{2-[2-(3-methylamino-propoxy)-ethoxy]-ethoxy}-propyl)-amine.

The structures and names of several other representative compounds of formula (I) follow.

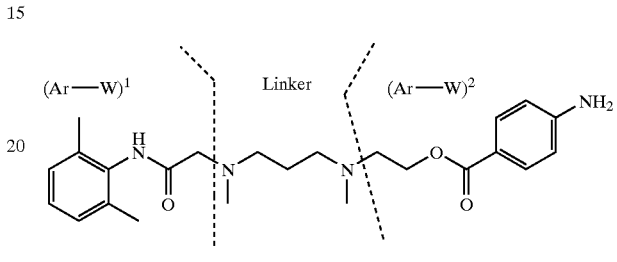

In the above compound, compound 73 in Table 2, ligand group (Ar—W)¹ is named 2,6-dimethylphenyl-NH—C(O)—CH$_2$—, ligand group (Ar—W)² is named 4-aminophenyl-C(O)—O—(CH$_2$)$_2$—, and the linker is —N(CH$_3$)—(CH$_2$)$_3$—N(CH$_3$)—.

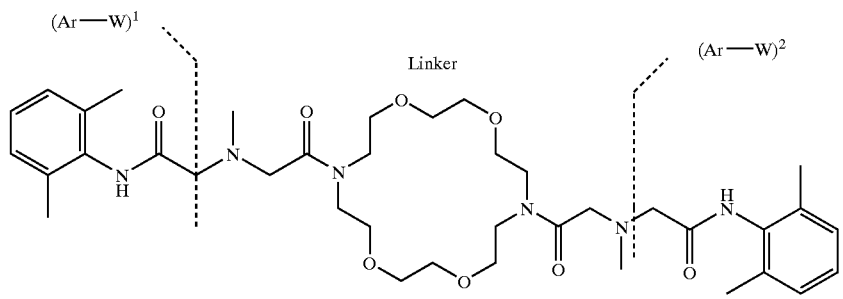

In the above compound, compound 90 in Table 2, the ligand groups (Ar—W)¹ and (Ar—W)² are both named 2,6-dimethylphenyl-NH—C(O)—CH$_2$—, and the linker is In IUPAC nomenclature, ligand group (Ar—W)¹ is named N-(2,6-dimethyl-phenyl)-acetamide, ligand group (Ar—W)² is named 4-amino-benzoic acid ethyl ester, and

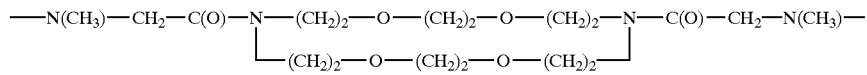

Using IUPAC nomenclature, the ligand groups are named N-(2,6-dimethyl-phenyl)-acetamide and the linker is named 2-methylamino-1-[16-(2-methylamino-acetyl)-1,4,10,13-tetraoxa-7,16-diaza-cyclooctadec-7-yl]ethanone.

the linker is named N,N'-dimethyl-propane-1,3-diamine.

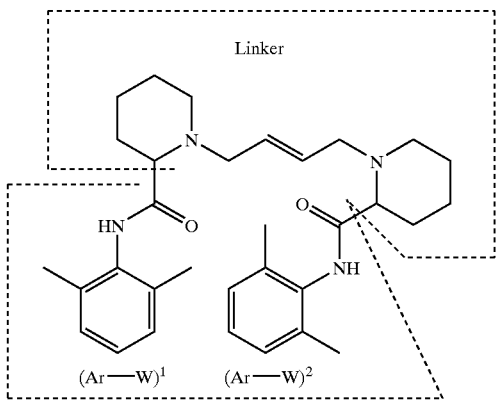

In the above compound, compound 41 in Table 2, the ligand groups (Ar—W)¹ and (Ar—W)² are named 2,6-dimethylphenyl-NH—C(O)— and the linker is:

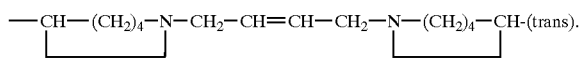

In IUPAC nomenclature, the ligand groups are named N-(2,6-dimethyl-phenyl)-formamide and the linker is named 1,1'-but-2-enylenedipiperidine.

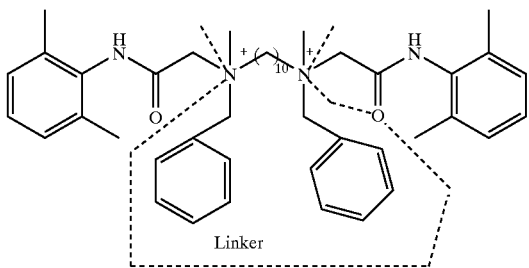

In the above compound, compound 111 in Table 2, the linker is named —N⁺(CH₃)(CH₂—Ph)—(CH₂)₁₀—N⁺(CH₃)(CH₂—Ph)—.

In IUPAC nomenclature, the linker is N,N'-dimethyl-N,N'dibenzyl-decane-1,10-diamine.

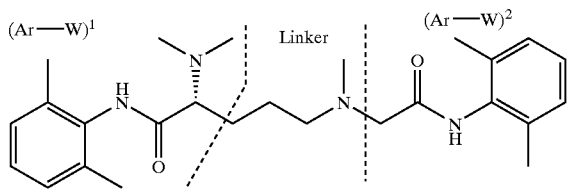

In the above compound, compound 124 in Table 2, the ligand group (Ar—W)¹ is named 2,6-dimethylphenyl-NH—C(O)—CH(N(CH₃)₂)— (R) isomer, the ligand group (Ar—W)² is named 2,6-dimethylphenyl-NH—C(O)—CH₂— and the linker is —(CH₂)₃N(CH₃)—.

In IUPAC nomenclature, ligand group (Ar—W)¹ is named 2-dimethylamino-N-2,6-dimethyl-phenyl)-acetamide, ligand group (Ar—W)² is named N-(2,6-dimethyl-phenyl)-acetamide, and the linker is named methyl-propyl-amine.

Compounds of Formula I

As explained above, the multibinding local anesthetic compounds described herein comprise 2–10 ligands of the same or different type attached covalently to a linker that links the ligands in a manner that allows their multivalent binding to ligand binding sites of sodium ion channels. The linker spatially constrains these interactions to occur within dimensions defined by the linker. This and other factors increases the biologic and/or therapeutic effect of the multibinding compound as compared to the same number of ligands used in monobinding form.

The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is provided below.

As noted previously, the linker may be considered as a framework to which ligands are attached. Thus, it should be recognized that the ligands can be attached at any suitable position on this framework, for example, at the termini of a linear chain or at any intermediate position thereof.

The simplest and most preferred multi-binding compound is a bivalent compound which can be represented as L—X—L, where L is a ligand and is the same or different and X is the linker. A trivalent compound could also be represented in a linear fashion, i.e., as a sequence of repeated units L—X—L—X—L, in which L is a ligand and is the same or different at each occurrence, as is X. However, a trivalent compound can also comprise three ligands attached to a central core, and thus be represented as $(L)_3X$, where the linker X could include, for example, an aryl, cycloalkyl or heterocyclic group. Tetravalent compounds can be represented in a linear array, L—X—L—X—L—X—L, or a branched array,

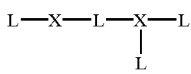

i.e., a branched construct analogous to the isomers of butane (n-butyl, iso-butyl, sec-butyl, and t- butyl). Alternatively, it could be represented as an aryl or cycloalkyl derivative as described above with four (4) ligands attached to the core linker.

The same considerations apply to higher multibinding compounds of this invention containing from 5–10 ligands. However, for multibinding agents attached to a central linker such as an aryl, cycloalkyl or heterocyclyl group, or a crown compound, there is a self-evident constraint that there must be sufficient attachment sites on the linker to accommodate the number of ligands present.

The formula $(L)_p(X)_q$ is also intended to be inclusive of a cyclic compound of formula $(—L—X—)_n$, where n is 2–10.

Figure 3:
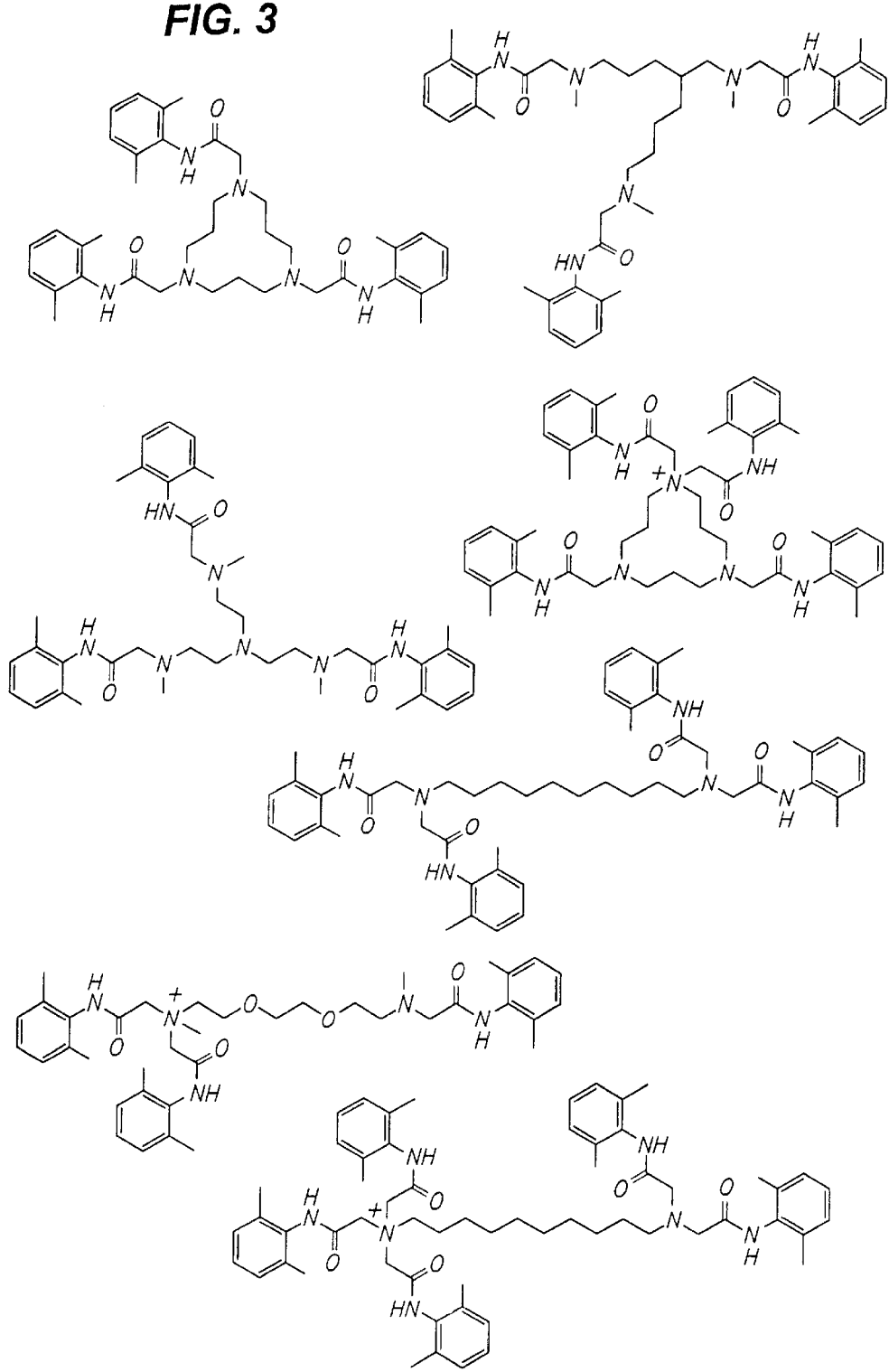
FIG. 3 shows trivalent and higher-order valency local anesthetic compounds of Formula I.

All of the above variations are intended to be within the scope of the invention defined by the formula $(L)_p(X)_q$. Representative multibinding compounds of Formula I , where p>2 are illustrated in FIG. 3.

With the foregoing in mind, a preferred linker for bivalent compounds may be represented by the following formula:

$$—X'—Z'''—(Y'—Z''')_v—X'— \qquad (V)$$

in which:

v is an integer of 0 to 20;

X' at each separate occurrence is independently alkylene, substituted alkylene, alkenylene, substituted alkenylene, alkynylene, substituted alkynylene, —O—, —S—, —S(O)—, —S(O)₂—, —NR—, —N⁺ R R'—, —C(O)—, —C(O)O—, —C(O)NR—, —NRC(O)—, —C(S)—, —C(S)O, —C(S)NR— or a covalent bond, where R and R' at each separate occurrence are independently as defined below for R' and R";

Z''' is at each separate occurrence independently selected from alkylene, substituted alkylene, (alkylene-O)$_w$-alkylene, where w is an integer of 1 to 10, alkylalkoxy, cycloalkylene, substituted cycloalkylene, alkenylene, substituted alkenylene, alkynylene, substituted alkynylene, cycloalkenylene, substituted cycloalkenylene, arylene, substituted arylene, heteroarylene, substituted heteroarylene, heterocyclene, substituted heterocyclene, crown compounds, or a covalent bond;

Y' at each separate occurrence is independently selected from —O—, NR', S, —C(O)—(CH$_2$)$_n$—NR'—, —NR—(CH$_2$)$_n$C(O)—, —NR'—C(O)—NR'—, —O—C(O)—O—, —NR'—C(═NR')—, —C(═NR')—NR'—, —NR'C(O)—O—, —N═C(X')—NR'—, —P(O)$_2$(OR')—O—, —S(O)$_n$—CR'R"—, —S(O)$_n$—NR—, S—S— and a covalent bond; where n is 0, 1, or 2; and R, R' and R" at each separate occurrence are selected from hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

Additionally, the linker moiety can be optionally substituted at any atom therein by one or more alkyl, substituted alkyl, cycloalkyl, substituted cycloalkyl, alkenyl, substituted alkenyl, alkynyl, substituted alkynyl, aryl, heteroaryl and heterocyclic groups.

Preferred Embodiments

Presently preferred compounds of Formula I are multibinding compounds of formula L—X—L and pharmaceutically acceptable salts thereof, wherein X is selected from structures of formula II (—N(R$^3$)—Z—N(R$^4$)—), formula III (—Y$^a$—Z'—Y$^b$—), and formula IV (—N$^+$(R$^3$)(R$^7$)—Z''-N$^+$(R$^4$)(R$^8$)—), where the substituents and linker components are as defined in the Summary of the Invention.

Each ligand L, which may be the same or different at each occurrence, independently comprises a group having the formula Ar—W—, where Ar is an aryl, heterocyclyl or heteroaryl group that is optionally substituted at one or more positions, and W is an atomic grouping through which attachment is made to the linker. As described in the Summary, W is selected from a covalent bond, —[CR$^1$R$^2$]$_r$—, [CR$^1$R$^2$]$_r$C(O), —C(O)O[CR$^1$R$^2$]$_r$, —OC(O)[ CR$^1$R$^2$]$_r$—, —O—[CR$^1$R$^2$]$_r$C(O)—, —C(O)—NH—[CR$^1$R$^2$]$_r$—, and —NH—C(O)[CR$^1$R$^2$]$_r$, where r is an integer of 0 to 10, and R$^1$ and R$^2$ are independently H, alkyl, substituted alkyl or a group —NR$^a$R$^b$—, where R$^a$ and R$^b$ are both alkyl.

One group of preferred ligands for use in multibinding compounds includes conventional local anesthetics such as those described above. Also included in this class of compounds are ligands that share common structural features with conventional local anesthetics, for example, an aryl ring linked via an ester or amide linkage to an aliphatic group having a terminal tertiary or quaternary amine. The number of atoms between the aryl ring and the amine, is typically about 3–7 atoms.

The modular, repeated tetrameric molecular structure of the sodium ion channel presents a plurality of cation binding sites. Accordingly, quaternary amines, guanidines and amidines are a second preferred class of binding group to be employed in a multi-binding local anesthetic compound. These positively charged amine moieties may comprise the terminal amine moiety of a local anesthetic-type binding group, or may be an ancillary group linked to a local anesthetic-type binding group, or to the linker framework of the multi-binding local anesthetic compound.

In addition to these interactions, the inclusion of one or more lipophilic ancillary groups, such as a long chain alkyl group or an aromatic hydrocarbon linked to the local anesthetic-type binding group, to a quaternary alkyl amine, or to the linker framework may provide for increased duration of binding of the multibinding local anesthetic compound.

The ligands, as described above, are linked together for multivalent binding interactions with ligand binding sites of a voltage-gated Na$^+$ ion channel. The multi-binding compound preferably includes at least two local anesthetic-type binding groups, and preferably additional ancillary groups from the second and third classes described above.

Preferred linkers comprises a linear, branched or cyclic chain having from two to fifty, and preferably two to twenty-four, non-hydrogen atoms, where the bonds making up the chain are selected from alkylene (carbon-carbon), alkenylene (double bonded carbon-carbon), alkylene ether (carbon-oxygen), alkylene thioether (carbon-sulfur), alkylene amino (carbon-nitrogen) linkages, or a combination thereof. The chain may further include one or more groups selected from cycloalkyl, heterocyclyl, aryl, heteroaryl, carbonyl, carboxy ester, carboxy amide, and sulfonyl, intervening between these bonds.

Figure 4A:
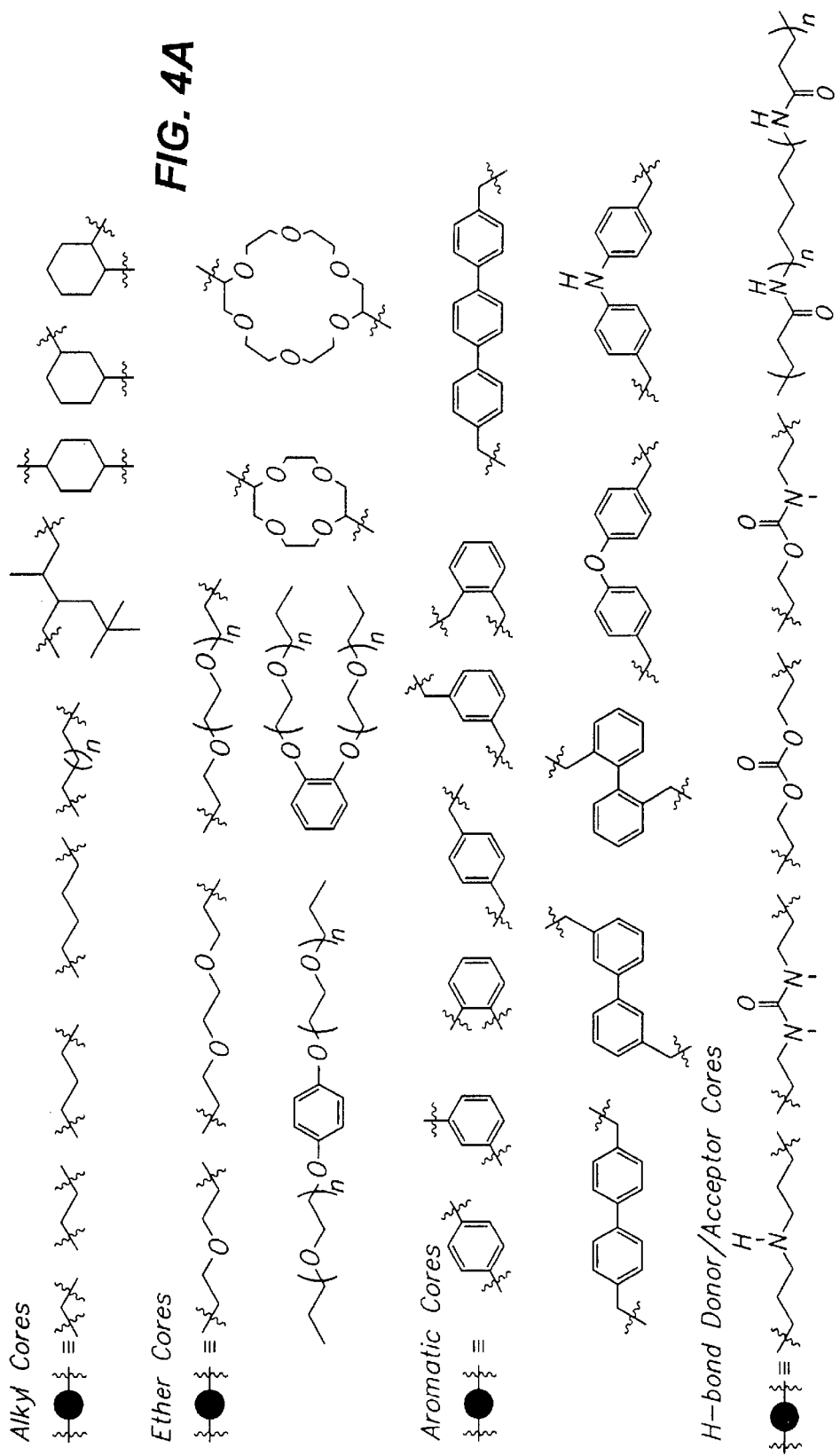
FIG. 4 illustrates representative types of linker cores for use in preparing multibinding compounds of Formula I.
Figure 4B:
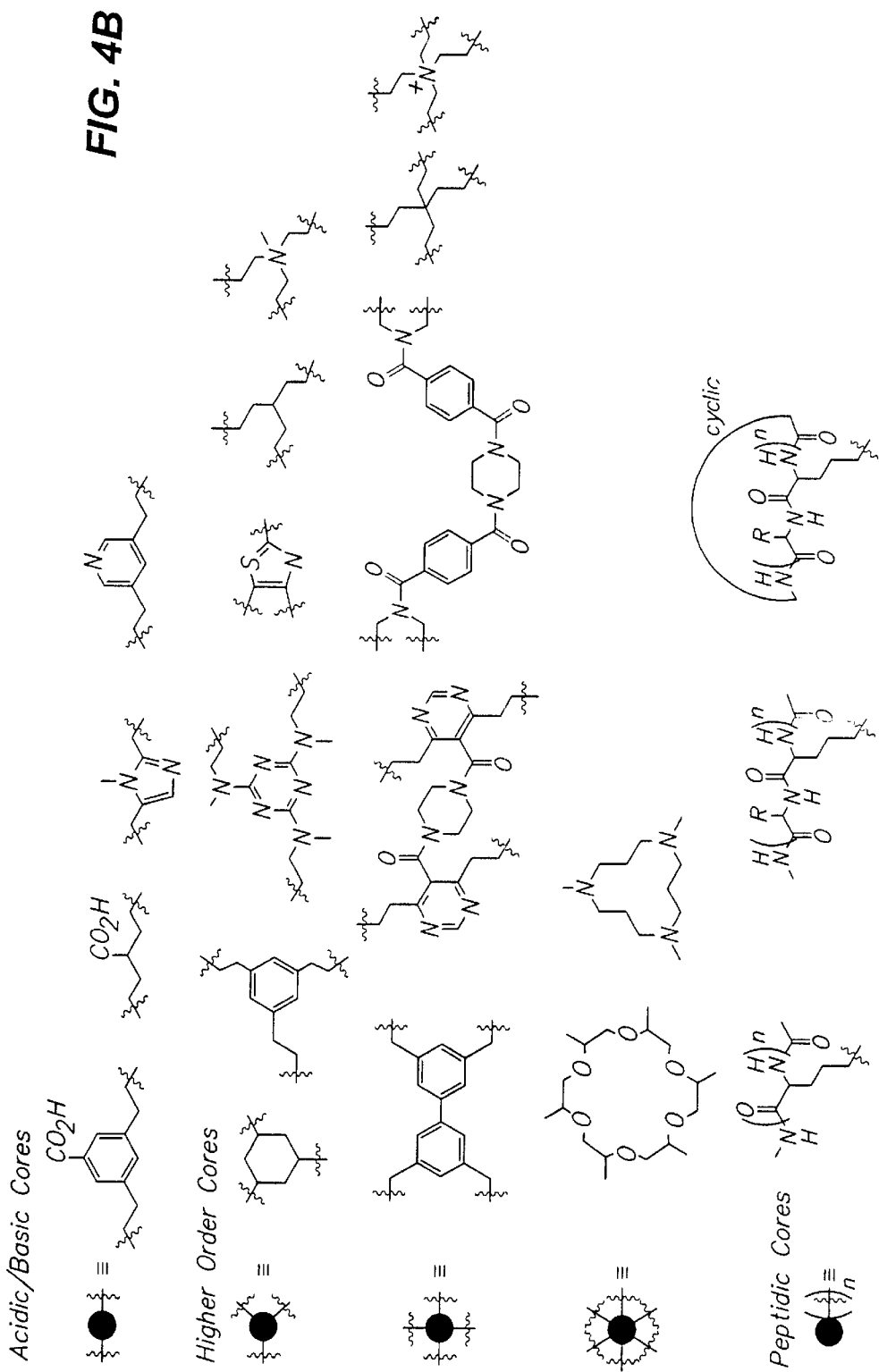
Figure 5A:
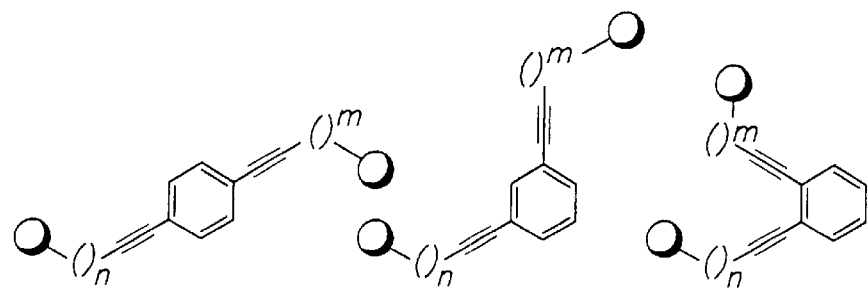
FIG. 5 illustrates a method for optimizing the linker geometry for presentation of ligands (filled circles) in bivalent compounds.
Figure 5B:
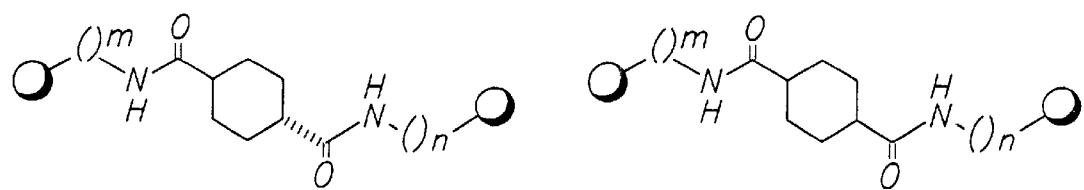
Figure 5B:
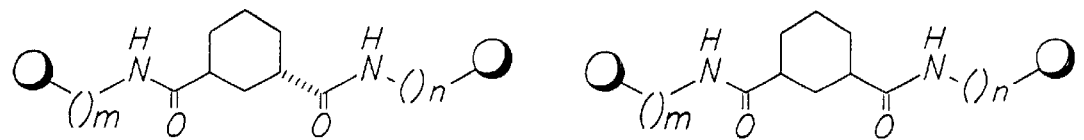
Figure 5B:
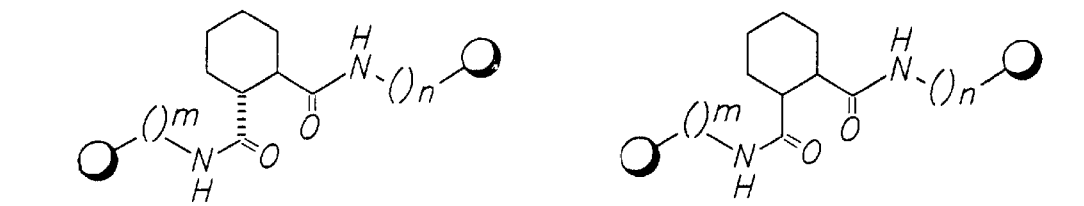

Local anesthetic-type ligands may be linked to the linker at different attachment points to achieve different orientations of the ligand domains, thereby to facilitate multivalency, as was discussed previously. This is illustrated below for lidocaine-based compounds of Formula I. In such compounds, lidocaine is preferably linked via the aliphatic amine moieties, via substituents on the benzene ring, or via the carbon which is alpha to the amide carbonyl group. The ligand and linkers shown below are selected for illustrative purposes only, and are not intended to limit the scope of the orientational analog compounds of this invention. As discussed previously, there are several classes of preferred linkers for local anesthetic-type compounds of this invention. Other preferred linkers and/or linker "cores" are exemplified below in Table 2 and FIG. 4.

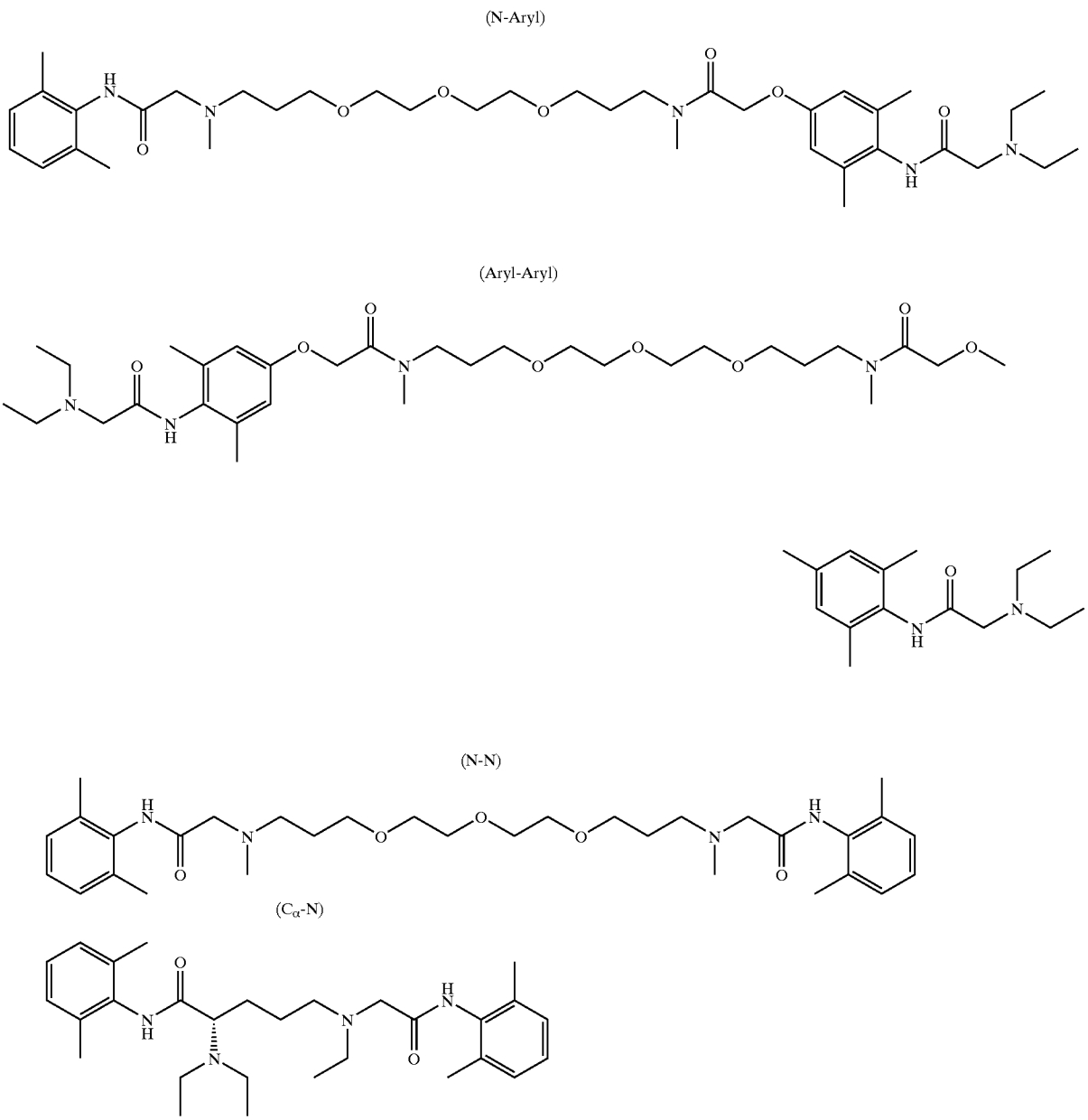

The multibinding compounds of this invention may also include one or more chiral centers; Such centers exist in the monobinding local anesthetic etidocaine, and non-racemic ligands, such as ropivacaine. The centers may be present in the linker of the compound, in the other types of binding groups, and in the ligands. Chirality may also be present in compounds lacking asymmetric atoms, e.g., in allene, biphenyl, spirane and helical compounds.

In one embodiment, the multibinding compound comprises ester linkages which provide for inactivation of the compound by plasma esterases should the compound enter the systemic circulation. Such linkages may be introduced into the linker or a pendant functionality, or into binding groups and ligands. In a particularly preferred embodiment of the invention that is generally applicable to compounds of Formula I, the cleavage of an ester bond in a ligand substituent converts a multibinding local anesthetic compound of long duration into a nontoxic membrane-impermeant compound, thereby eliminating or greatly reducing its systemic toxicity.

Accordingly, presently preferred embodiments are hereinafter represented by Formulas Ia, Ib and Ic,

| | |
|---|---|
| Ar-W-N($R^3$)-Z-N($R^4$)-W-Ar | Ia |
| Ar-W-$Y^a$-$Z^1$-$Y^b$-W-Ar | Ib |
| Ar-W-$N^+$($R^{3'}$)($R^7$)-$Z^{11}$-$N^+$($R^{4'}$)($R^8$)-W-Ar | Ic. |

Representative compounds are shown in Table 2. These compounds were characterized by mass spectroscopy and tested for activity in representative and well-accepted assays described herein (see Testing below). Compounds 156 and 170 are synthetic intermediates of compounds of Formula I.

TABLE 2

Compounds of Formula I

| # | Ar— | (Ar—W)[1] —W— | -Linker- | —W— | (W—Ar)[2] —Ar |
|---|---|---|---|---|---|
| 1 | 2,6-dimethylphenyl- | —NH—C(O)—CH₂— | —N(CH₃)—(CH₂)₆—N(CH₃)— | —CH₂—C(O)—NH— | -2,6-dimethylphenyl |
| 2 | 2,6-dimethylphenyl- | —NH—C(O)—CH₂— | —N(CH₂CH₃)—(CH₂)₂—N(CH₂CH₃)— | —CH₂—C(O)—NH— | -2,6-dimethylphenyl |
| 3 | 2,6-dimethylphenyl- | —NH—C(O)—CH₂— | —N(CH₃)—(CH₂)₃—N(CH₃)— | —CH₂—C(O)—NH— | -2,6-dimethylphenyl |
| 4 | 2,6-dimethylphenyl- | —NH—C(O)—CH₂— | —N(CH₃)—(CH₂)₂—N(CH₃)— | —CH₂—C(O)—NH— | -2,6-dimethylphenyl |
| 5 | 2,6-dimethylphenyl- | —NH—C(O)—CH₂— | —N(CH₃)—(CH₂)₁₀—N(CH₃)— | —CH₂—C(O)—NH— | -2,6-dimethylphenyl |
| 6 | 2,6-dimethylphenyl- | —NH—C(O)—CH₂— | —N(CH₃)—(CH₂)₁₂—N(CH₃)— | —CH₂—C(O)—NH— | -2,6-dimethylphenyl |
| 7 | 2,6-dimethylphenyl- | —NH—C(O)—CH₂— | —N((CH₂)₇CH₃)—(CH₂)₁₀—N((CH₂)₇CH₃)— | —CH₂—C(O)—NH— | -2,6-dimethylphenyl |
| 8 | 2,6-dimethylphenyl- | —NH—C(O)—CH₂— | —N(CH₂—Ph)—(CH₂)₁₀—N(CH₂—Ph)— | —CH₂—C(O)—NH— | -2,6-dimethylphenyl |
| 9 | 2,6-dimethylphenyl- | —NH—C(O)—CH₂— | —N(CH₃)—(CH₂)₄—N(CH₃)— | —CH₂—C(O)—NH— | -2,6-dimethylphenyl |
| 10 | 2,6-dimethylphenyl- | —NH—C(O)—CH₂— | —N(CH₂CH₃)—(CH₂)₃—N(CH₂CH₃)— | —CH₂—C(O)—NH— | -2,6-dimethylphenyl |
| 11 | 2,6-dimethylphenyl- | —NH—C(O)— | —CH—(CH₂)₄—N—(CH₂)₁₀—N—(CH₂)₄—CH— | —C(O)—NH— | -2,6-dimethylphenyl |
| 12 | 2,6-dimethylphenyl- | —NH—C(O)—CH₂— | —N(CH₃—CH₂OH)—(CH₂)₂—N(CH₃)— | —CH₂—C(O)—NH— | -2,6-dimethylphenyl |
| 13 | 2,6-dimethylphenyl- | —NH—C(O)—CH₂— | —N(CH₃)—(CH₂)₅—N(CH₃)— | —CH₂—C(O)—NH— | -2,6-dimethylphenyl |
| 14 | 2,6-dimethylphenyl- | —NH—C(O)—CH₂— | —N(CH₃)—(CH₂)₈—N(CH₃)— | —CH₂—C(O)—NH— | -2,6-dimethylphenyl |
| 15 | 2,6-dimethylphenyl- | —NH—C(O)—CH(CH₂CH₃)— | —NH—(CH₂)₅—NH— | —CH(CH₂CH₃)—C(O)—NH— | -2,6-dimethylphenyl |
| 16 | 2,6-dimethylphenyl- | —NH—C(O)—CH(CH₂CH₃)— | —NH—(CH₂)₄—NH— | —CH(CH₂CH₃)—C(O)—NH— | -2,6-dimethylphenyl |
| 17 | 2,6-dimethylphenyl- | —NH—C(O)—CH(CH₂CH₃)— | —N(CH₃)—(CH₂)₅—N(CH₃)— | —CH(CH₂CH₃)—C(O)—NH— | -2,6-dimethylphenyl |
| 18 | 2,6-dimethylphenyl- | —NH—C(O)—CH(CH₂CH₃)— | —N(CH₃)—(CH₂)₄—N(CH₃)— | —CH(CH₂CH₃)—C(O)—NH— | -2,6-dimethylphenyl |
| 19 | 2,6-dimethylphenyl- | —NH—C(O)—CH(CH₂CH₃)— | —N(CH₃)—(CH₂)₃—N(CH₃)— | —CH(CH₂CH₃)—C(O)—NH— | -2,6-dimethylphenyl |
| 20 | 2,6-dimethylphenyl- | —NH—C(O)—CH(CH₂CH₃)— | —NH—(CH₂)₃—NH— | —CH(CH₂CH₃)—C(O)—NH— | -2,6-dimethylphenyl |
| 21 | 2,6-dimethylphenyl- | —NH—C(O)—CH₂— | —N((CH₂)₂CH₃)—(CH₂)₃—N((CH₂)₂CH₃)— | —CH₂—C(O)—NH— | -2,6-dimethylphenyl |
| 22 | 2,6-dimethylphenyl- | —NH—C(O)—CH₂— | —N(CH₂CH₃)—(CH₂)₃—N(CH₂CH₃)— | —CH₂—C(O)—NH— | -2,6-dimethylphenyl |
| 23 | 2,6-dimethylphenyl- | —NH—C(O)—CH₂— | —N(CH₂—CH₂—OCH₃)—(CH₂)₃—N(CH₂—CH₂—OCH₃)— | —CH₂—C(O)—NH— | -2,6-dimethylphenyl |
| 24 | 2,6-dimethylphenyl- | —NH—C(O)—CH₂— | —N(CH₂—CH₂—OCH₃)—(CH₂)₂—N(CH₂—CH₂—OCH₃)— | —CH₂—C(O)—NH— | -2,6-dimethylphenyl |
| 25 | 2,6-dimethylphenyl- | —NH—C(O)—CH₂— | —N((CH₂)₂CH₃)—(CH₂)₂—N((CH₂)₂CH₃)— | —CH₂—C(O)—NH— | -2,6-dimethylphenyl |
| 26 | 2,6-dimethylphenyl- | —NH—C(O)—CH₂— | —N((CH₂)₂CH₃)—(CH₂)₅—N((CH₂)₂CH₃)— | —CH₂—C(O)—NH— | -2,6-dimethylphenyl |
| 27 | 2,6-dimethylphenyl- | —NH—C(O)—CH₂— | —N(CH₂—CH₂—OCH₃)—(CH₂)₄—N(CH₂—CH₂—OCH₃)— | —CH₂—C(O)—NH— | -2,6-dimethylphenyl |
| 28 | 2,6-dimethylphenyl- | —NH—C(O)—CH₂— | —N((CH₂)₂CH₃)—(CH₂)₄—N((CH₂)₂CH₃)— | —CH₂—C(O)—NH— | -2,6-dimethylphenyl |
| 29 | 2,6-dimethylphenyl- | —NH—C(O)—CH₂— | —N(CH₂—CH₂—OCH₃)—(CH₂)₅—N(CH₂—CH₂—OCH₃)— | —CH₂—C(O)—NH— | -2,6-dimethylphenyl |
| 30 | 2,6-dimethylphenyl- | —NH—C(O)—CH₂— | —N(CH₂CH₃)—(CH₂)₄—N(CH₂CH₃)— | —CH₂—C(O)—NH— | -2,6-dimethylphenyl |
| 31 | 2,6-dimethylphenyl- | —NH—C(O)—CH₂— | —N(CH₂CH₃)—(CH₂)₅—N(CH₂CH₃)— | —CH₂—C(O)—NH— | -2,6-dimethylphenyl |
| 32 | 2,6-dimethylphenyl- | —NH—C(O)—CH₂— | —N((CH₂)₂CH₃)—(CH₂)₅—N((CH₂)₂CH₃)— | —CH(CH₂CH₃)—C(O)—NH— | -2,6-dimethylphenyl |

TABLE 2-continued

Compounds of Formula I

| # | Ar— | (Ar—W)¹ —W— | Linker -Linker- | (W—Ar)² —W— | —Ar |
|---|---|---|---|---|---|
| 33 | 2,6-dimethylphenyl- | —CH(CH₂CH₃)— | —N((CH₂)₂CH₃)—(CH₂)₄—N((CH₂)₂CH₃)— | —CH(CH₂CH₃)—C(O)—NH— | -2,6-dimethylphenyl |
| 34 | 2,6-dimethylphenyl- | —NH—C(O)— | —N(CH₂CH₃)—(CH₂)₅—N(CH₂CH₃)— | —CH(CH₂CH₃)—C(O)—NH— | -2,6-dimethylphenyl |
| 35 | 2,6-dimethylphenyl- | —NH—C(O)— | —N(CH₃)—CH₂—OCH₃)—(CH₂)₅—N(CH₂—CH₂—OCH₃)— | —CH(CH₂CH₃)—C(O)—NH— | -2,6-dimethylphenyl |
| 36 | 2,6-dimethylphenyl- | —NH—C(O)— | —N(CH₂CH₃)—(CH₂)₄—N(CH₂—CH₂—OCH₃)— | —CH(CH₂CH₃)—C(O)—NH— | -2,6-dimethylphenyl |
| 37 | 2,6-dimethylphenyl- | —NH—C(O)— | —N(CH₂—CH₂—OCH₃)—(CH₂)₄—N(CH₂—CH₂—OCH₃)— | —CH(CH₂CH₃)—C(O)—NH— | -2,6-dimethylphenyl |
| 38 | 2,6-dimethylphenyl- | —NH—C(O)— | —CH—(CH₂)₄—N—(CH₂)₃—N—(CH₂)₄—CH— | —C(O)—NH— | -2,6-dimethylphenyl |
| 39 | 2,6-dimethylphenyl- | —NH—C(O)— | —CH—(CH₂)₄—N—(CH₂)₄—N—(CH₂)₄—CH— | —C(O)—NH— | -2,6-dimethylphenyl |
| 40 | 2,6-dimethylphenyl- | —NH—C(O)— | —CH—(CH₂)₄—N—(CH₂)₆—N—(CH₂)₄—CH— | —C(O)—NH— | 2,6-dimethylphenyl |
| 41 | 2,6-dimethylphenyl- | —NH—C(O)— | —CH—(CH₂)₄—N—CH₂—CH=CH—CH₂—N—(CH₂)₄—CH-trans | —C(O)—NH— | -2,6-dimethylphenyl |
| 42 | 2,6-dimethylphenyl- | —NH—C(O)—CH₂— | —N(CH₃)—CH₂—CH=CH—CH₂—N(CH₃)— | —CH₂—C(O)—NH— | -2,6-dimethylphenyl |
| 43 | 2,6-dimethylphenyl- | —NH—C(O)—CH₂— | —N(CH₃)—CH₂—1,4 phenyl-CH₂—N(CH₃)— | —CH₂—C(O)—NH— | -2,6-dimethylphenyl |
| 44 | 2,6-dimethylphenyl- | —NH—C(O)—CH₂— | —N(CH₃)—CH₂—2,6 napthyl-CH₂—N(CH₃)— | —CH₂—C(O)—NH— | -2,6-dimethylphenyl |
| 45 | 2,6-dimethylphenyl- | —NH—C(O)—CH₂— | —N(CH₃)—CH₂—1,4-phenyl-CH₂—CH₂—N(CH₃)— | —CH₂—C(O)—NH— | -2,6-dimethylphenyl |
| 46 | 2,6-dimethylphenyl- | —NH—C(O)—CH₂— | —N(CH₃)—CH₂—1,2 phenyl-CH₂—N(CH₃)— | —CH₂—C(O)—NH— | -2,6-dimethylphenyl |
| 47 | 2,6-dimethylphenyl- | —NH—C(O)—CH₂— | —N(CH₃)—CH₂—1,3 cyclohexane-CH₂—N(CH₃)— | —CH₂—C(O)—NH— | -2,6-dimethylphenyl |
| 48 | 2,6-dimethylphenyl- | —NH—C(O)—CH₂— | —N(CH₃)—(CH₂)₃—N,N-piperazine-(CH₂)₃—N(CH₃)— | —CH₂—C(O)—NH— | -2,6-dimethylphenyl |
| 49 | 2,6-dimethylphenyl- | —NH—C(O)—CH₂— | —N(CH₃)—(CH₂)₂—N(CH₃)—(CH₂)₂—N(CH₃)— | —CH₂—C(O)—NH— | -2,6-dimethylphenyl |
| 50 | 2,6-dimethylphenyl- | —NH—C(O)—CH₂— | —N(CH₃)—(CH₂)₂—O—(CH₂)₂—O—(CH₂)₂—N(CH₃)— | —CH₂—C(O)—NH— | -2,6-dimethylphenyl |
| 51 | 4-[O—(CH₂)₇CH₃]-2,6-dimethylphenyl | —NH—C(O)—CH₂— | —N(CH₃)—(CH₂)₃—O—(CH₂)₄—O—(CH₂)₃—N(CH₃)— | —CH₂—C(O)—NH— | 4-[O—(CH₂)₇CH₃]-2,6-dimethylphenyl |
| 52 | 2,6-dimethylphenyl- | —NH—C(O)—CH₂— | —N(CH₃)—(CH₂)₃—O—(CH₂)₃—N(CH₃)—C(O)—N(CH₃)—(CH₂)₃—O—(CH₂)₃—N(CH₃)— | —CH₂—C(O)—NH— | -2,6-dimethylphenyl |
| 53 | 2,6-dimethylphenyl- | —NH—C(O)—CH₂— | —N(CH₃)—(CH₂)₃—O—(CH₂)₄—O—(CH₂)₃—N(CH₃)— | —CH₂—C(O)—NH— | -2,6-dimethylphenyl |
| 54 | 2,6-dimethylphenyl- | —NH—C(O)—CH(CH₂CH₃)— | —N(CH₃)—(CH₂)₃—O—(CH₂)₂—O—(CH₂)₃—N(CH₃)— | —CH(CH₂CH₃)—C(O)—NH— | -2,6-dimethylphenyl |
| 55 | 2,6-dimethylphenyl- | —NH—C(O)—CH(CH₂CH₃)— | —N((CH₂)₂CH₃)—(CH₂)₃—O—(CH₂)₂—O—(CH₂)₃—N(((CH₂)₂CH₃)— | —CH(CH₂CH₃)—C(O)—NH— | -2,6-dimethylphenyl |

TABLE 2-continued

Compounds of Formula I

| # | Ar— | (Ar—W)$^1$ —W— | Linker -Linker- | —W— | (W—Ar)$^2$ —Ar |
|---|---|---|---|---|---|
| 56 | 2,6-dimethylphenyl- | —NH—C(o)—CH$_2$— | —NH—(CH$_2$)$_4$—NH— | | -2,6-dimethylphenyl |
| 57 | o-tolyl- | —NH—C(O)—CH(CH$_3$)— | —NH—(CH$_2$)$_4$—NH— | —CH$_2$—C(O)—NH— | -o-tolyl |
| 58 | 2,6-dimethylphenyl- | —NH—C(O)—CH$_2$— | —N(CH$_3$)—CH(C(O)—O—CH$_2$CH$_3$)—(CH$_2$)$_4$—N(CH$_3$)— (R) isomer | —CH$_2$(CH$_3$)—C(O)—NH— | -2,6-dimethylphenyl |
| 59 | 4-(C(O)—NH—(CH$_2$)$_2$—N(CH$_2$CH$_3$)$_2$)—phenyl- | — | —NH—(CH$_2$)$_4$—NH— | — | 4-(C(O)—NH—(CH$_2$)$_2$—N(CH$_2$CH$_3$)$_2$)—phenyl |
| 60 | 4-(C(O)—NH—(CH$_2$)$_2$—N(CH$_2$CH$_3$)$_2$)—phenyl- | — | —NH—(CH$_2$)$_4$—NH— | — | 4-(C(O)—NH—(CH$_2$)$_2$—N(CH$_2$CH$_3$)$_2$)—phenyl |
| 61 | 4-(C(O)—NH—(CH$_2$)$_2$—N(CH$_2$CH$_3$)$_2$)—phenyl- | — | —NH—(CH$_2$)$_5$—NH— | — | 4-(C(O)—NH—(CH$_2$)$_2$—N(CH$_2$CH$_3$)$_2$)—phenyl |
| 62 | 4-(C(O)—NH—(CH$_2$)$_2$—N(CH$_2$CH$_3$)$_2$)—phenyl- | — | —NH—(CH$_2$)$_7$—NH— | — | 4-(C(O)—NH—(CH$_2$)$_2$—N(CH$_2$CH$_3$)$_2$)—phenyl |
| 63 | 4-(C(O)—NH—(CH$_2$)$_2$—N(CH$_2$CH$_3$)$_2$)—phenyl- | — | —NH—(CH$_2$)$_8$—NH— | — | 4-(C(O)—NH—(CH$_2$)$_2$—N(CH$_2$CH$_3$)$_2$)—phenyl |
| 64 | 4-(C(O)—NH—(CH$_2$)$_2$—N(CH$_2$CH$_3$)$_2$)—phenyl- | — | —NH—(CH$_2$)$_9$—NH— | — | 4-(C(O)—NH—(CH$_2$)$_2$—N(CH$_2$CH$_3$)$_2$)—phenyl |
| 65 | 4-(C(O)—NH—(CH$_2$)$_2$—N(CH$_2$CH$_3$)$_2$)—phenyl- | — | —NH—(CH$_2$)$_{10}$—NH— | — | 4-(C(O)—NH—(CH$_2$)$_2$—N(CH$_2$CH$_3$)$_2$)—phenyl |
| 66 | 4-(C(O)—NH—(CH$_2$)$_2$—N(CH$_2$CH$_3$)$_2$)—phenyl- | — | —NH—(CH$_2$)$_{12}$—NH— | — | 4-(C(O)—NH—(CH$_2$)$_2$—N(CH$_2$CH$_3$)$_2$)—phenyl |
| 67 | 4-butylaminophenyl- | —C(O)— | —N(CH$_3$)—(CH$_2$)$_2$—O—(CH$_2$)$_2$—O—(CH$_2$)$_3$—NH— | —C(O)— | 4-butylaminophenyl |
| 68 | 2,6-dimethylphenyl- | —O—C(O)—CH$_2$— | —N(CH$_3$)—(CH$_2$)$_3$—O—(CH$_2$)$_2$—O—(CH$_2$)$_3$—N(CH$_3$) | —CH$_2$—C(O)—O— | -2,6-dimethylphenyl |
| 69 | 2,6-dimethylphenyl- | —NH—C(O)—CH$_2$— | —N(CH$_3$)—(CH$_2$)$_3$—O—(CH$_2$)$_2$—O—(CH$_2$)$_3$—N(CH$_3$) | —(CH$_2$)$_3$— | -phenyl |
| 70 | 2,6-dimethylphenyl- | —NH—C(O)—CH$_2$— | —N(CH$_3$)—(CH$_2$)$_3$—O—(CH$_2$)$_2$—O—(CH$_2$)$_3$—N(CH$_3$) | —C(O)—(CH$_2$)$_2$— | -phenyl |
| 71 | 2,6-dimethylphenyl- | —NH—C(O)—CH$_2$— | —N(CH$_3$)—(CH$_2$)$_3$—O—(CH$_2$)$_2$—O—(CH$_2$)$_3$—N(CH$_3$) | —CH$_2$—C(O)—O— | -2,6-dimethylphenyl |
| 72 | 2,6-dimethylphenyl- | —NH—C(O)—CH$_2$— | —N(CH$_3$)—(CH$_2$)$_3$—O—(CH$_2$)$_2$—O—(CH$_2$)$_3$—N(CH$_3$) | —CH$_2$—C(O)—O— | -3,5-dimethyl-4-(NH—C(O)—CH$_2$—N(CH$_2$CH$_3$)$_2$)—phenyl |
| 73 | 2,6-dimethylphenyl- | —NH—C(O)—CH$_2$— | —N(CH$_3$)—(CH$_2$)$_3$—N(CH$_3$) | —(CH$_2$)$_2$—O—C(O)— | 4-aminophenyl |
| 74 | 2,6-dimethylphenyl- | —NH—C(O)—CH$_2$— | —N(CH$_3$)—(CH$_2$)$_3$—N(CH$_3$) | —C(O)— | 4-aminophenyl |
| 75 | 2,6-dimethylphenyl- | —NH—C(O)—CH$_2$— | —N—(CH$_2$)$_3$—NH—(CH$_2$)$_3$—N— | —CH$_2$—C(O)—NH— | -2,6-dimethylphenyl |
| 76 | 2,6-dimethylphenyl- | —NH—C(O)—CH$_2$— | —N—(CH$_2$)$_2$—O—(CH$_2$)$_2$—N— (CH$_2$)$_2$—O—(CH$_2$)$_2$— | —CH$_2$—C(O)—NH— | -2,6-dimethylphenyl |

TABLE 2-continued

Compounds of Formula I

| # | Ar— | (Ar—W)¹ —W— | Linker -Linker- | (W—Ar)² —W— | —Ar |
|---|---|---|---|---|---|
| 77 | 2,6-dimethylphenyl- | —NH—C(O)—CH₂— | —N—(CH₂)₂—O—(CH₂)₂—N—<br>          (CH₂)₂—O—(CH₂)₂ | —CH₂—C(O)—NH— | 2,6-dimethylphenyl |
| 78 | 4-methoxyphenyl- | —NH—C(O)—CH₂— | —N—(CH₂)₂—O—(CH₂)₂—N—<br>          (CH₂)₂—O—(CH₂)₂ | —CH₂—C(O)—NH— | 4-methoxyphenyl |
| 79 | o-tolyl- | —NH—C(O)—CH₂— | —N—(CH₂)₂—O—(CH₂)₂—N—<br>          (CH₂)₂—O—(CH₂)₂ | —CH₂—C(O)—NH— | o-tolyl- |
| 80 | phenyl- | —NH—C(O)—CH₂— | —N—(CH₂)₂—O—(CH₂)₂—N—<br>          (CH₂)₂—O—(CH₂)₂ | —CH₂—C(O)—NH— | phenyl- |
| 81 | 4-chlorophenyl- | —NH—C(O)—CH₂— | —N—(CH₂)₂—O—(CH₂)₂—N—<br>          (CH₂)₂—O—(CH₂)₂ | —CH₂—C(O)—NH— | 4-chlorophenyl |
| 82 | 2-methyl-4-methoxyphenyl- | —NH—C(O)—CH₂— | —N—(CH₂)₂—O—(CH₂)₂—N—<br>          (CH₂)₂—O—(CH₂)₂ | —CH₂—C(O)—NH— | 2-methyl-4-methoxyphenyl |
| 83 | 2-methyl-4-chlorophenyl- | —NH—C(O)—CH₂— | —N—(CH₂)₂—O—(CH₂)₂—N—<br>          (CH₂)₂—O—(CH₂)₂ | —CH₂—C(O)—NH— | 2-methyl-4-chlorophenyl |
| 84 | 2,6-dimethylphenyl- | —NH—C(O)—CH₂— | —N—(CH₂)₃—O—(CH₂)₂—O—(CH₂)₃—N—<br>          (CH₂)₂—O—(CH₂)₂—O—(CH₂)₂ | —CH₂—C(O)—NH— | 2,6-dimethylphenyl |
| 85 | 2,6-dimethylphenyl- | —NH—C(O)—CH(CH₂CH₃)— | —N—(CH₂)₂—O—(CH₂)₂—N—<br>          (CH₂)₂—O—(CH₂)₂ | —CH(CH₂CH₃)—C(O)—NH— | 2,6-dimethylphenyl |
| 86 | 2,6-dimethylphenyl- | —NH—C(O)—CH₂— | —N—(CH₂)₂—O—(CH₂)₂—N—<br>          (CH₂)₆ | —CH₂—C(O)—NH— | 2,6-dimethylphenyl |

TABLE 2-continued

Compounds of Formula I

| # | Ar— | (Ar—W)$^1$ —W— | Linker -Linker- | —W— | (W—Ar)$^2$ —Ar |
|---|---|---|---|---|---|
| 87 | 2,6-dimethylphenyl- | —NH—C(O)—CH$_2$— | —N—(CH$_2$)$_2$—O—(CH$_2$)$_2$—N— with —(CH$_2$)$_6$— bridge | —CH$_2$—C(O)—NH— | 2,6-dimethylphenyl |
| 88 | 2,6-dimethylphenyl- | —NH—C(O)—CH$_2$— | —N—(CH$_2$)$_2$—O—(CH$_2$)$_2$—N—(CH$_2$)$_2$—O—(CH$_2$)$_2$— | —CH$_2$—C(O)—NH— | 2,6-dimethylphenyl |
| 89 | 2,6-dimethylphenyl- | —NH—C(O)—CH((CH$_2$)$_3$CH$_3$)— | —N—(CH$_2$)$_2$—O—(CH$_2$)$_2$—N—(CH$_2$)$_2$—O—(CH$_2$)$_2$— | —CH((CH$_2$)$_3$CH$_3$)—C(O)—NH— | 2,6-dimethylphenyl |
| 90 | 2,6-dimethylphenyl- | —NH—C(O)—CH$_2$— | —N(CH$_3$)—CH$_2$—C(O)—N—(CH$_2$)$_2$—O—(CH$_2$)$_2$—N—C(O)—CH$_2$—N(CH$_3$)— with (CH$_2$)$_2$—O—(CH$_2$)$_2$ bridge | —CH$_2$—C(O)—NH— | 2,6-dimethylphenyl |
| 91 | 2,6-dimethylphenyl- | —NH—C(O)—CH$_2$— | —N—(CH$_2$)$_2$—O—(CH$_2$)$_2$—N—C(O)—CH$_2$—N(CH$_3$)— with —(CH$_2$)$_2$—O—(CH$_2$)$_2$— | —CH$_2$—C(O)—NH— | 2,6-dimethylphenyl |
| 92 | 2,6-dimethylphenyl- | —NH—C(O)—CH$_2$— | —N—(CH$_2$)$_2$—O—(CH$_2$)$_2$—N—C(O)—(CH$_2$)$_3$—N(CH$_3$)— with —(CH$_2$)$_2$—O—(CH$_2$)$_2$— | —CH$_2$—C(O)—NH— | 2,6-dimethylphenyl |
| 93 | 2,6-dimethylphenyl- | —NH—C(O)—CH(CH$_2$CH$_3$)— | —N—(CH$_2$)$_2$—O—(CH$_2$)$_2$—N—(CH$_2$)$_2$—O—(CH$_2$)$_2$— | —CH$_2$—C(O)—NH— | 2,6-dimethylphenyl |
| 94 | 2,6-dimethylphenyl- | —NH—C(O)—CH(CH$_3$)— | —N—(CH$_2$)$_2$—O—(CH$_2$)$_2$—N—(CH$_2$)$_2$—O—(CH$_2$)$_2$— | —CH(CH$_3$)—C(O)—NH— | 2,6-dimethylphenyl |
| 95 | o-tolyl- | —NH—C(O)—CH(CH$_3$)— | —N—(CH$_2$)$_2$—O—(CH$_2$)$_2$—N—(CH$_2$)$_2$—O—(CH$_2$)$_2$— | —CH(CH$_3$)—C(O)—NH— | o-tolyl |
| 96 | 2,6-dimethylphenyl- | —NH—C(O)—CH(CH$_2$CH$_3$)— | —N—(CH$_2$)$_2$—O—(CH$_2$)$_2$—N—(CH$_2$)$_2$—O—(CH$_2$)$_2$— | —CH(CH$_3$)—C(O)—NH— | o-tolyl |

TABLE 2-continued

Compounds of Formula I

| # | Ar— | (Ar—W)$^1$ -W— | Linker -Linker- | (W—Ar)$^2$ -W— | -Ar |
|---|---|---|---|---|---|
| 97 | 2,6-dimethylphenyl- | —NH—C(O)—CH(CH$_2$CH$_3$)— | —N[(CH$_2$)$_2$—O—(CH$_2$)$_2$][(CH$_2$)$_2$—O—(CH$_2$)$_2$]— | —CH(CH$_3$)—C(O)—NH— | -2,6-dimethylphenyl |
| 98 | 2,6-dimethylphenyl- | —NH—C(O)—CH$_2$— | —N[(CH$_2$)$_2$—O—(CH$_2$)$_2$][(CH$_2$)$_2$—O—(CH$_2$)$_2$]— | —CH(CH$_3$)—C(O)—NH— | -o-tolyl |
| 99 | phenyl- | —(CH$_2$)$_2$—C(O)— | —N[(CH$_2$)$_2$—O—(CH$_2$)$_2$][(CH$_2$)$_2$—O—(CH$_2$)$_2$]— | —C(O)—(CH$_2$)$_2$— | phenyl- |
| 100 | 4-aminophenyl- | —C(O)—O—(CH$_2$)$_2$— | —N[(CH$_2$)$_2$—O—(CH$_2$)$_2$][(CH$_2$)$_2$—O—(CH$_2$)$_2$]— | —(CH$_2$)$_2$—O—C(O)— | -4-aminophenyl |
| 101 | 4-nitrophenyl- | —C(O)—O—(CH$_2$)$_2$— | —N[(CH$_2$)$_2$—O—(CH$_2$)$_2$][(CH$_2$)$_2$—O—(CH$_2$)$_2$]— | —(CH$_2$)$_2$—O—C(O)— | -4-nitrophenyl |
| 102 | 2,6-dimethylphenyl- | —O—C(O)—CH$_2$— | —N[(CH$_2$)$_2$—O—(CH$_2$)$_2$][(CH$_2$)$_2$—O—(CH$_2$)$_2$]— | —CH$_2$—C(O)—O— | -2,6-dimethylphenyl |
| 103 | 2-chloro-4-nitrophenyl- | —C(O)—O—(CH$_2$)$_2$— | —N[(CH$_2$)$_2$—O—(CH$_2$)$_2$][(CH$_2$)$_2$—O—(CH$_2$)$_2$]— | —(CH$_2$)$_2$—O—C(O)— | -2-chloro-4-nitrophenyl |
| 104 | 2,6-dimethylphenyl- | —NH—C(O)—CH$_2$— | —N[(CH$_2$)$_2$][(CH$_2$)$_2$]— | —CH$_2$—C(O)—NH— | -2,6-dimethylphenyl |
| 105 | 2,6-dimethylphenyl- | —NH—C(O)—CH$_2$— | —N[(CH$_2$)$_2$—CH—(CH$_2$)$_2$][(CH$_2$)$_2$]— | —CH$_2$—C(O)—NH— | -2,6-dimethylphenyl |
| 106 | 2,6-dimethylphenyl- | —NH—C(O)—CH$_2$— | —N[(CH$_2$)$_2$—CH—(CH$_2$)$_2$—CH—(CH$_2$)$_2$][(CH$_2$)$_2$]— | —CH$_2$—C(O)—NH— | -2,6-dimethylphenyl |
| 107 | 2,6-dimethylphenyl- | —NH—C(O)—CH$_2$— | —N[(CH$_2$)$_2$—CH—(CH$_2$)$_3$—CH—(CH$_2$)$_2$][(CH$_2$)$_2$]— | —CH$_2$—C(O)—NH— | -2,6-dimethylphenyl |

TABLE 2-continued

Compounds of Formula I

| # | Ar— | (Ar—W)[1] —W— | Linker -Linker- | (W—Ar)[2] —W— | —Ar |
|---|---|---|---|---|---|
| 108 | 4-aminophenyl- | —C(O)—O—(CH$_2$)$_2$— | —N(CH$_3$)— | —(CH$_2$)$_2$—O—C(O)— | 4-aminophenyl |
| 109 | 2,6-dimethylphenyl- | —NH—C(O)—CH$_2$— | —N$^+$(CH$_3$)((CH$_2$)$_7$CH$_3$)—(CH$_2$)$_{10}$—N$^+$(CH$_3$)((CH$_2$)$_7$CH$_3$)— | —CH$_2$—C(O)—NH— | 2,6-dimethylphenyl |
| 110 | 2,6-dimethylphenyl- | —NH—C(O)—CH$_2$— | —N$^+$(CH$_3$)$_2$—(CH$_2$)$_{10}$—N$^+$(CH$_3$)$_2$— | —CH$_2$—C(O)—NH— | 2,6-dimethylphenyl |
| 111 | 2,6-dimethylphenyl- | —NH—C(O)—CH$_2$— | —N$^+$(CH$_3$)(CH$_2$—Ph)—(CH$_2$)$_{10}$—N$^+$(CH$_3$)(CH$_2$—Ph)— | —CH$_2$—C(O)—NH— | 2,6-dimethylphenyl |
| 112 | 2,6-dimethylphenyl- | —NH—C(O)—CH$_2$— | —N$^+$(CH$_3$)$_2$—(CH$_2$)$_3$—O—(CH$_2$)$_2$—O—(CH$_2$)$_2$—O—(CH$_2$)$_3$—N$^+$(CH$_3$)$_2$— | —CH$_2$—C(O)—NH— | 2,6-dimethylphenyl |
| 113 | 2,6-dimethylphenyl- | —NH—C(O)—CH$_2$— | —N$^+$(CH$_3$)$_2$—CH$_2$-1,4 phenyl-CH$_2$—N$^+$(CH$_3$)$_2$— | —CH$_2$—C(O)—NH— | 2,6-dimethylphenyl |
| 114 | 2,6-dimethylphenyl- | —NH—C(O)—CH$_2$— | —N$^+$(CH$_3$)$_2$—CH$_2$-1,2 phenyl-CH$_2$—N$^+$(CH$_3$)$_2$— | —CH$_2$—C(O)—NH— | 2,6-dimethylphenyl |
| 115 | 2,6-dimethylphenyl- | —NH—C(O)—CH$_2$— | —N$^+$(CH$_3$)$_2$—CH$_2$-2,6 napthyl—CH$_2$—N$^+$(CH$_3$)$_2$— | —CH$_2$—C(O)—NH— | 2,6-dimethylphenyl |
| 116 | 2,6-dimethylphenyl- | —NH—C(O)—CH(N(CH$_3$)$_2$)— (S) isomer | —(CH$_2$)$_3$—N(CH$_3$)— | —CH$_2$—C(O)—NH— | 2,6-dimethylphenyl |
| 117 | o-tolyl- | —NH—C(O)—CH(CH$_3$)— | —N(CH$_3$)—(CH$_2$)$_4$—N(CH$_3$)— | —CH(CH$_3$)—C(O)—NH— | o-tolyl |
| 118 | o-tolyl- | —NH—C(O)—CH(CH$_3$)— | —N(CH$_3$)—(CH$_2$)$_5$—N(CH$_3$)— | —CH(CH$_3$)—C(O)—NH— | o-tolyl |
| 119 | o-tolyl- | —NH—C(O)—CH(CH$_3$)— | —NH—(CH$_2$)$_4$—NH— | —CH(CH$_3$)—C(O)—NH— | o-tolyl |
| 120 | 2,6-dimethylphenyl- | —NH—C(O)—CH$_2$— | —NH—(CH$_2$)$_4$—NH— | —CH$_2$—C(O)—NH— | 2,6-dimethylphenyl |
| 121 | 2,6-dimethylphenyl- | —NH—C(O)—CH$_2$— | —(CH$_2$)$_4$—N(CH$_3$)— | —CH$_2$—C(O)—NH— | 2,6-dimethylphenyl |
| 122 | 2,6-dimethylphenyl- | —CH(N(CH$_3$)$_2$)— (S) isomer | —(CH$_2$)$_3$—N(CH$_2$CH$_3$)— | —CH$_2$—C(O)—NH— | 2,6-dimethylphenyl |
| 123 | 2,6-dimethylphenyl- | —NH—C(O)—CH(N(CH$_3$)$_2$)—(R) isomer | —(CH$_2$)$_4$—N(CH$_3$)— | —CH$_2$—C(O)—NH— | 2,6-dimethylphenyl |
| 124 | 2,6-dimethylphenyl- | —NH—C(O)—CH(N(CH$_3$)$_2$)—(R) isomer | —(CH$_2$)$_5$—N(CH$_3$)— | —CH$_2$—C(O)—NH— | 2,6-dimethylphenyl |
| 125 | 4-(C(O)—O—(CH$_2$)$_2$—N(CH$_3$)$_2$)—phenyl- | — | —NH—(CH$_2$)$_5$—NH— | — | 4-(C(O)—O—(CH$_2$)$_2$—N(CH$_3$)$_2$)—phenyl |
| 126 | 2,6-dimethylphenyl- | —NH—C(O)—CH$_2$— | —N(cyclopropyl)—CH$_2$—CH=CH—CH$_2$—N(cyclopropyl)— | —CH$_2$—C(O)—NH— | 2,6-dimethylphenyl |
| 127 | 2,6-dimethylphenyl- | —NH—C(O)—CH(N(CH$_3$)$_2$)— (S) isomer | —(CH$_2$)$_2$—N(CH$_3$)— | —CH$_2$—C(O)—NH— | 2,6-dimethylphenyl |
| 128 | 4-(C(O)—O—(CH$_2$)$_2$—N(CH$_3$)$_2$)—phenyl- | — | —NH—(CH$_2$)$_8$—NH— | — | 4-(C(O)—O—(CH$_2$)$_2$—N(CH$_3$)$_2$)—phenyl |
| 129 | 4-(C(O)—NH(CH$_3$))—phenyl- | — | —NH—(CH$_2$)$_8$—NH— | — | 4-(C(O)—NH—CH$_2$)$_2$)—phenyl |
| 130 | 4-(C(O)—O—(CH$_2$)$_2$—N(CH$_3$)$_2$)-phenyl- | — | —NH—(CH$_2$)$_8$—N(CH$_3$)— | —CH$_2$—C(O)—NH— | 2,6-dimethylphenyl |
| 131 | 2,6-dimethylphenyl- | —NH—C(O)—CH(CH$_2$CH$_3$)—(R) isomer | —N—(CH$_2$)$_2$—O—(CH$_2$)$_2$—N—(CH$_2$)$_2$—O—(CH$_2$)$_2$— | —CH(CH$_2$CH$_3$)—C(O)—NH— (R) isomer | 2,6-dimethylphenyl |

TABLE 2-continued

Compounds of Formula I

| # | Ar— | (Ar—W)[1] —W— | Linker -Linker- | (W—Ar)[2] —W— | —Ar |
|---|-----|------|--------|------|-----|
| 132 | 4-(C(O)—O—(CH$_2$)$_2$—N(CH$_3$)$_2$)-phenyl- | — | —N(C(O)—CF$_3$)—(CH$_2$)$_8$—N(CH$_3$)— | —CH$_2$—C(O)—NH— | -2,6-dimethylphenyl |
| 133 | 4-(C(O)—O—(CH$_2$)$_2$—N(CH$_3$)$_2$)-phenyl- | — | —NH—(CH$_2$)$_5$—N(CH$_3$)— | —CH$_2$—C(O)—NH— | -2,6-dimethylphenyl |
| 134 | 4-(C(O)—O—(CH$_2$)$_2$—N(CH$_3$)$_2$)-phenyl- | — | —NH—(CH$_2$)$_8$—N(CH$_3$)— | —CH$_2$—C(O)—NH— | -2,6-dimethylphenyl |
| 135 | 2,6-dimethylphenyl- | —NH—C(O)—CH(CH$_2$CH$_3$)— | —N[—(CH$_2$)$_2$—O—(CH$_2$)$_2$—]$_2$N— | —CH(CH$_2$CH$_3$)—C(O)—NH— | -o-tolyl |
| 136 | o-tolyl- | —NH—C(O)—CH(CH$_2$CH$_3$)— | —N[—(CH$_2$)$_2$—O—(CH$_2$)$_2$—]$_2$N— | —CH(CH$_2$CH$_3$)—C(O)—NH— | -o-tolyl |
| 137 | 2,6-dimethylphenyl- | —NH—C(O)—CH(N(CH$_2$CH$_3$)$_2$)— (S) isomer | —(CH$_2$)$_4$—N(CH$_2$CH$_3$)— | —CH$_2$—C(O)—NH— | -2,6-dimethylphenyl |
| 138 | 2,6-dimethylphenyl- | —NH—C(O)—CH(N(CH$_2$CH$_3$)$_2$)— | —(CH$_2$)$_4$—N(CH$_2$CH$_3$)— | —CH$_2$—C(O)—NH— | -2,6-dimethylphenyl |
| 139 | 2,6-dimethylphenyl- | —NH—C(O)—CH(N(CH$_2$CH$_3$)$_2$)— (R) isomer | —(CH$_2$)$_5$—N(CH$_2$CH$_3$)— | —CH$_2$—C(O)—NH— | -2,6-dimethylphenyl |
| 140 | 2,6-dimethylphenyl- | —NH—C(O)—CH$_2$— | —N(CH$_2$—CH=CH$_2$)—(CH$_2$)$_4$—N(CH$_2$—CH=CH$_2$)— | —CH$_2$—C(O)—NH— | -2,6-dimethylphenyl |
| 141 | 2,6-dimethylphenyl- | —NH—C(O)—CH$_2$— | —NH—(CH$_2$)$_4$—N(CH$_2$—CH=CH$_2$)— | —CH$_2$—C(O)—NH— | -2,6-dimethylphenyl |
| 142 | 2,6-dimethylphenyl- | —NH—C(O)—CH$_2$— | —N(CH$_3$)—(CH$_2$)$_4$—N(CH$_3$)— | —CH(CH$_2$CH$_3$)—C(O)—NH— | -2,6-dimethylphenyl |
| 143 | 2,6-dimethylphenyl- | —NH—C(O)—CH$_2$— | —N(CH$_3$)—(CH$_2$)$_4$—N(CH$_3$)— | —CH(CH$_3$)—C(O)—NH— | -2,6-dimethylphenyl |
| 144 | 4-[O—(CH$_2$)$_3$CH$_3$]-2,6-dimethylphenyl | —NH—C(O)—CH$_2$— | —N(CH$_3$)—(CH$_2$)$_4$—N(CH$_3$)— | —CH$_2$—C(O)—NH— | -2,6-dimethylphenyl |
| 145 | 4-[O—CH$_2$—C(O)—OCH$_3$]-2,6-dimethylphenyl | —NH—C(O)—CH$_2$— | —N(CH$_3$)—(CH$_2$)$_4$—N(CH$_3$)— | —CH$_2$—C(O)—NH— | -2,6-dimethylphenyl |
| 146 | 2,6-dimethylphenyl- | —NH—C(O)—CH$_2$— | —N(CH$_3$)—(CH$_2$)$_4$—N(CH$_3$)— | —CH$_2$—C(O)—NH— | -o-tolyl |
| 147 | -2,4,6-trimethylphenyl | —NH—C(O)—CH(CH$_2$CH$_3$)— | —N[—(CH$_2$)$_2$—O—(CH$_2$)$_2$—]$_2$N— | —CH(CH$_2$CH$_3$)—C(O)—NH— | -2,4,6-trimethylphenyl |
| 148 | 2-ethyl-6-methylphenyl- | —NH—C(O)—CH(CH$_2$CH$_3$)— | —N[—(CH$_2$)$_2$—O—(CH$_2$)$_2$—]$_2$N— | —CH(CH$_2$CH$_3$)—C(O)—NH— | -2-ethyl-6-methylphenyl |

TABLE 2-continued

Compounds of Formula I

| # | Ar— | (Ar—W)¹ —W— | Linker -Linker- | (W—Ar)² —W— | —Ar |
|---|---|---|---|---|---|
| 149 | 2,6-dimethylphenyl- | —NH—C(O)—CH(CH₂CH₃)— (S) isomer | —N[—(CH₂)₂—O—(CH₂)₂—][—(CH₂)₂—O—(CH₂)₂—]N— | —CH(CH₂CH₃)—C(O)—NH— (S) isomer | —2,6-dimethylphenyl |
| 150 | 2,6-dimethylphenyl- | —NH—C(O)—CH(CH₂CH₃)— (S) isomer | —N[—(CH₂)₂—O—(CH₂)₂—][—(CH₂)₂—O—(CH₂)₂—]N— | —CH(CH₂CH₃)—C(O)—NH— (R) isomer | —2,6-dimethylphenyl |
| 151 | 2,6-dimethylphenyl- | —NH—C(O)—CH((CH₂)₂CH₃)— | —N[—(CH₂)₂—O—(CH₂)₂—][—(CH₂)₂—O—(CH₂)₂—]N— | —CH((CH₂)₂CH₃)—C(O)—NH— | —2,6-dimethylphenyl |
| 152 | 4-[O—CH₂—C(O)—CH₃]-2,6-dimethylphenyl- | —NH—C(O)—CH₂— | —N(CH₃)—(CH₂)₄—N(CH₃)— | —CH₂—C(O)—NH— | 4-[O—(CH₂)₃CH₃]-2,6-dimethylphenyl |
| 153 | 4-[O—CH₂—C(O)—O]-2,6-dimethylphenyl- | —NH—C(O)—CH₂— | —N(CH₃)—(CH₂)₄—N(CH₃)— | —CH₂—C(O)—NH— | 4-[O—(CH₂)₃CH₃]-2,6-dimethylphenyl |
| 154 | 4-[O—CH₂—C(O)—O]-2,6-dimethylphenyl- | —NH—C(O)—CH(N(CH₂CH₃)₂)— (R) isomer | —(CH₂)₃—N(CH₂CH₃)— | —CH₂—C(O)—NH— | 4-[O—CH₂C(O)OCH₃]-2,6-dimethylphenyl |
| 155 | 4-[O—CH₂—C(O)—O—CH₂CH₃]-2,6-dimethylphenyl- | —NH—C(O)—CH(CH₃)— | —N[—(CH₂)₂—O—(CH₂)₂—][—(CH₂)₂—O—(CH₂)₂—]N— | —CH(CH₂CH₃)—C(O)—NH— | —2,6-dimethylphenyl |
| 156 | 4-[O—CH₂—C(O)]—O-2,6-dimethylphenyl- | —NH—C(O)—CH(CH₂CH₃)— | —N[—(CH₂)₂—O—(CH₂)₂—][—(CH₂)₂—O—(CH₂)₂—]N— | —CH(CH₂CH₃)—C(O)—NH— | —2,6-dimethylphenyl |
| 157 | 4-[O—(CH₂)₃CH₃]-2,6-dimethylphenyl | —NH—C(O)—CH₂— | —N[—(CH₂)₂—O—(CH₂)₂—][—(CH₂)₂—O—(CH₂)₂—]N— | —CH₂—C(O)—NH— | —2,6-dimethylphenyl |
| 158 | 4-[O—CH₂—C(O)]—O-2,6-dimethylphenyl- | —NH—C(O)—CH₂— | —N[—(CH₂)₂—O—(CH₂)₂—][—(CH₂)₂—O—(CH₂)₂—]N— | —CH₂—C(O)—NH— | —2,6-dimethylphenyl |
| 159 | 4-[O—CH₂—C(O)—O—CH₂CH₃]-2,6-dimethylphenyl- | —NH—C(O)—CH₂— | —N(CH₃)—(CH₂)₄—N(CH₃)— | —CH₂—C(O)—NH— | —2,6-dimethylphenyl |
| 160 | 4-[C(O)—O—CH₂CH₃]-2,6-dimethylphenyl- | —NH—C(O)—CH₂— | —N(CH₃)—(CH₂)₄—N(CH₃)— | —CH₂—C(O)—NH— | —2,6-dimethylphenyl |

TABLE 2-continued

Compounds of Formula I

| # | Ar— | (Ar—W)[1] —W— | Linker -Linker- | —W— | (W—Ar)[2] —Ar |
|---|---|---|---|---|---|
| 161 | 4-[C(O)—O—CH₃]-2,6-dimethylphenyl- | —NH—C(O)—CH(CH₂CH₃)— | —N[—(CH₂)₂—O—(CH₂)₂—][—(CH₂)₂—O—(CH₂)₂—]N— | —CH(CH₂CH₃)—C(O)—NH— | -2,6-dimethylphenyl |
| 162 | 4-[O—CH₂—C(O)—O—(CH₂)₄CH₃]-2,6-dimethylphenyl- | —NH—C(O)—CH₂— | —N(CH₃)—(CH₂)₄—N(CH₃)— | —CH₂—C(O)—NH— | -2,6-dimethylphenyl |
| 163 | 4-[C(O)—O—CH₃]-2-methylphenyl- | —NH—C(O)—CH(CH₂CH₃)— | —N[—(CH₂)₂—O—(CH₂)₂—][—(CH₂)₂—O—(CH₂)₂—]N— | —CH(CH₂CH₃)—C(O)—NH— | -2,6-dimethylphenyl |
| 164 | 4-[C(O)—O—CH₃]-2,6-dimethylphenyl- | —NH—C(O)—CH(CH₃)— | —N[—(CH₂)₂—O—(CH₂)₂—][—(CH₂)₂—O—(CH₂)₂—]N— | —CH(CH₃)—C(O)—NH— | -2,6-dimethylphenyl |
| 165 | 4-[O—CH₂—C(O)—O—CH(CH₃)₂]-2,6-dimethylphenyl- | —NH—C(O)—CH₂— | —N(CH₃)—(CH₂)₄—N(CH₃)— | —CH₂—C(O)—NH— | -2,6-dimethylphenyl |
| 166 | 4-[O—(CH₂)₃—C(O)—O—CH₂CH₃]-2,6-dimethylphenyl- | —NH—C(O)—CH₂— | —N(CH₃)—(CH₂)₄—N(CH₃)— | —CH₂—C(O)—NH— | -2,6-dimethylphenyl |
| 167 | 4-[O—(CH₂)₂CH₃]-2,6-dimethylphenyl- | —NH—C(O)—CH₂— | —N(CH₃)—(CH₂)₄—N(CH₃)— | —CH₂—C(O)—NH— | -2,6-dimethylphenyl |
| 168 | 4-[O—(CH₂)₃CH₃]-2,6-dimethylphenyl | —NH—C(O)—CH₂— | —N(CH₃)—(CH₂)₄—N(CH₃)— | —CH₂—C(O)—NH— | 4-[C(O)—CH₂CH₃]-2,6-dimethylphenyl |
| 169 | 4-[O—CH(CH₃)₂]-2,6-dimethylphenyl | —NH—C(O)—CH₂— | —N(CH₃)—(CH₂)₄—N(CH₃)— | —CH₂—C(O)—NH— | -2,6-dimethylphenyl |
| 170 | 4-[O—CH₂—COOH]-2,6-dimethylphenyl- | —NH—C(O)—CH₂— | —N(CH₃)—(CH₂)₄—N(CH₃)— | —CH₂—C(O)—NH— | -2,6-dimethylphenyl |
| 171 | 2-methylphenyl | —NH—C(O)—CH(CH₃)— | —N[—(CH₂)₂—O—(CH₂)₂—][—(CH₂)₂—O—(CH₂)₂—]N— | —CH(C₂H₃)—C(O)—NH— | 2-methyl-6-(carboxymethyl)phenyl |
| 172 | 2-methylphenyl | —NH—C(O)—CH(C₂H₅)— | —N[—(CH₂)₂—O—(CH₂)₂—][—(CH₂)₂—O—(CH₂)₂—]N— | —CH(C₂H₅)—C(O)—NH— | 2-methyl-6-(carboxymethyl)phenyl |
| 173 | 2,6-dimethylphenyl | —NH—C(O)—CH₂— | —N(CH₃)—(CH₂)₄—N(CH₃)— | —CH₂—C(O)—NH— | 2-methyl-4-(carboxymethyl)phenyl |
| 174 | 2-methylphenyl | —NH—C(O)—CH(C₂H₅)— | —N(CH₃)—(CH₂)₄—N(CH₃)— | —CH(C₂H₅)—C(O)—NH | 2,6-dimethyl-4-(carboxymethyl)phenyl |
| 175 | 2-methylphenyl | —NH—C(O)—CH(CH₃)— | —N(CH₃)—(CH₂)₄—N(CH₃)— | —CH₂—C(O)—NH— | 2,6-dimethyl-6-n-butoxy- |

TABLE 2-continued

Compounds of Formula I

| # | Ar— | —W— | -Linker- | —W— | —Ar |
|---|---|---|---|---|---|
| | (Ar—W)[1] | | Linker | (W—Ar)[2] | |
| 176 | 2,6-dimethylphenyl | —NH—C(O)—CH($C_2H_5$)— | —NH—($CH_2$)$_2$—O—($CH_2$)$_2$—O—($CH_2$)$_2$—N— | —CH($C_2H_5$)—C(O)—NH | phenyl 2,6-dimethylphenyl |
| 177 | 2-methylphenyl | —NH—C(O)—CH($CH_3$)— | —N—($CH_2$)$_2$—O—($CH_2$)$_2$—O—($CH_2$)$_2$—N—<br>  ($CH_2$)$_2$—O—($CH_2$)$_2$—O—($CH_2$)$_2$— | —CH($C_2H_5$)—C(O)—NH | 2,6-dimethyl-4-(carboxymethyl)phenyl |
| 178 | 2,6-dimethylphenyl | —NH—C(O)—C($CH_3$)$_2$— | NH—($CH_2$)$_2$—O—($CH_2$)$_2$—O—($CH_2$)$_2$—N— | —C($CH_3$)$_2$—NH—C(O)— | 2,6-dimethylphenyl |
| 179 | 2,6-dimethyl-6-n-butoxy-phenyl | —NH—C(O)—$CH_2$— | —N($CH_3$)—($CH_2$)$_4$—N($CH_3$)— | —CH($CH_3$)—NH—C(O)— | 2,6-dimethylphenyl |
| 180 | 2-methyl-6-methoxyphenyl | —NH—C(O)—CH($C_2H_5$)— | —N—($CH_2$)$_2$—O—($CH_2$)$_2$—O—($CH_2$)$_2$—N—<br>  ($CH_2$)$_2$—O—($CH_2$)$_2$—O—($CH_2$)$_2$— | —CH($C_2H_5$)—C(O)—NH | 2-methyl-6-methoxyphenyl |
| 181 | 2,6-dimethylphenyl | —NH—C(O)—$CH_2$— | —N($CH_3$)—($CH_2$)$_4$—N($CH_3$)— | —$CH_2$—C(O)—NH | 2,6-dimethyl-4-n-pentoxyphenyl |
| 182 | 2,6-dimethylphenyl | —NH—C(O)—$CH_2$— | —N($CH_3$)—($CH_2$)$_4$—N($CH_3$)— | —$CH_2$—C(O)—NH | 2,6-dimethyl-4-n-hexyloxyphenyl |
| 183 | 2-methyl-6-carboxyphenyl | —NH—C(O)—CH($C_2H_5$)— | —N—($CH_2$)$_2$—O—($CH_2$)$_2$—O—($CH_2$)$_2$—N—<br>  ($CH_2$)$_2$—O—($CH_2$)$_2$—O—($CH_2$)$_2$— | —CH($C_2H_5$)—C(O)—NH | 2-methylphenyl |
| 184 | 2,6-dimethylphenyl | —NH—C(O)—C($CH_3$)$_2$— | —N—($CH_2$)$_2$—O—($CH_2$)$_2$—O—($CH_2$)$_2$—N—<br>  ($CH_2$)$_2$—O—($CH_2$)$_2$—O—($CH_2$)$_2$— | —C($CH_3$)$_2$—NH—C(O)— | 2,6-dimethylphenyl |
| 185 | 2-methyl-4-n-butoxyphenyl | —NH—C(O)—$CH_2$— | —N($CH_3$)—($CH_2$)$_4$—N($CH_3$)— | —$CH_2$—C(O)—NH | 2,6-dimethylphenyl |
| 186 | 4-n-butoxyphenyl | —NH—C(O)—$CH_2$— | —N($CH_3$)—($CH_2$)$_4$—N($CH_3$)— | —$CH_2$—C(O)—NH | 2,6-dimethylphenyl |
| 187 | 2,6-dimethyl-4-(methoxyethoxy)phenyl | —NH—C(O)—$CH_2$— | —N($CH_3$)—($CH_2$)$_4$—N($CH_3$)— | —$CH_2$—C(O)—NH | 2,6-dimethylphenyl |
| 188 | 2,6-dimethyl-4-(ethoxyethoxy)phenyl | —NH—C(O)—CH($CH_3$)— | —N—($CH_2$)$_2$—O—($CH_2$)$_2$—O—($CH_2$)$_2$—N—<br>  ($CH_2$)$_2$—O—($CH_2$)$_2$—O—($CH_2$)$_2$— | —$CH_2$—C(O)—NH | 2,6-dimethylphenyl |
| 189 | 2-methylphenyl | —NH—C(O)—CH($CH_3$)— | —N—($CH_2$)$_2$—O—($CH_2$)$_2$—O—($CH_2$)$_2$—N—<br>  ($CH_2$)$_2$—O—($CH_2$)$_2$—O—($CH_2$)$_2$— | —CH($C_2H_5$)—C(O)—NH | 2,6-dimethyl-6-(1-butyl-carbonyloxymethoxy-carbonyl)phenyl |
| 190 | 2,6-dimethyl-4-(methoxycarbonylethyl)phenyl | —NH—C(O)—CH($C_2H_5$)— | —N—($CH_2$)$_2$—O—($CH_2$)$_2$—O—($CH_2$)$_2$—N—<br>  ($CH_2$)$_2$—O—($CH_2$)$_2$—O—($CH_2$)$_2$— | —CH($C_2H_5$)—C(O)—NH | 2-methylphenyl |

TABLE 2-continued

Compounds of Formula I

| # | Ar— | (Ar—W)¹ —W— | Linker -Linker- | —W— | (W—Ar)² —Ar |
|---|---|---|---|---|---|
| 191 | 2,6-dimethyl-4-(methoxycarbonylethyl)phenyl | —NH—C(O)—CH(C₂H₅)— | —N—(CH₂)₂—O—(CH₂)₂—N—(CH₂)₂—O—(CH₂)₂ | —CH(C₂H₅)—C(O)—NH | 2,6-dimethylphenyl |
| 192 | 2-methyl-3-(ethoxycarbonylmethoxy)-phenyl | —NH—C(O)—CH(C₂H₅)— | —N—(CH₂)₂—O—(CH₂)₂—N—(CH₂)₂—O—(CH₂)₂ | —CH(CH₃)—C(O)—NH | 2-methylphenyl |
| 193 | 2,6-dimethylphenyl | —NH—C(O)—CH(C₂H₅)— | —N—(CH₂)₂—O—(CH₂)₂—N—(CH₂)₂—O—(CH₂)₂ | —CH(C₂H₅)—C(O)—NH | 2-methyl-3-(ethoxycarbonylmethoxy) |
| 194 | 2,6-dimethyl-4-(methoxycarbonylethyl)phenyl | —NH—C(O)—CH(C₂H₅)— | —N—(CH₂)₂—O—(CH₂)₂—N—(CH₂)₂—O—(CH₂)₂ | —CH(CH₃)—C(O)—NH | 2-methylphenyl |
| 195 | 2-methyl-6-(methoxycarbonylvinyl)phenyl | —NH—C(O)—CH(C₂H₅)— | —N—(CH₂)₂—O—(CH₂)₂—N—(CH₂)₂—O—(CH₂)₂ | —CH(C₂H₅)—C(O)—NH | 2,6-dimethylphenyl |
| 196 | 2,6-dimethyl-4-(ethoxycarbonylmethyl)phenyl | —NH—C(O)—CH(C₃H₇)— | —N—(CH₂)₂—O—(CH₂)₂—N—(CH₂)₂—O—(CH₂)₂ | —CH(CH₃)—C(O)—NH | 2-methylphenyl |
| 197 | 2,6-dimethylphenyl | —NH—C(O)—CH(C₂H₅)— | —N—(CH₂)₂—O—(CH₂)₂—N—(CH₂)₂—O—(CH₂)₂ | —CH(C₂H₅)—C(O)—NH | 2,6-di-methylphenyl |
| 198 | 2,6-dimethylphenyl | —NH—C(O)—CH(C₂H₅)— | —N—(CH₂)₂—O—(CH₂)₂—N—(CH₂)₂—O—(CH₂)₂ | —CH(C₂H₅)—C(O)—NH | 2,6-di-methylphenyl |

TABLE 2-continued

Compounds of Formula I

| | | (Ar—W)¹ | | Linker | (W—Ar)² | |
|---|---|---|---|---|---|---|
| # | Ar— | —W— | -Linker- | | —W— | —Ar |
| 199 | 2-methyl-6-(methoxycarbonylethyl)phenyl | —NH—C(O)—CH(C₂H₅)— | —N—(CH₂)₂—O—(CH₂)₂—N—<br>            |<br>      (CH₂)₂—O—(CH₂)₂ | | —CH(C₂H₅)—C(O)—NH— | 2,6-dimethylphenyl |
| 199 | 2,6-dimethyl-4-(ethoxycarbonylmethyl)phenyl | —NH—C(O)—CH₂— | —N(CH₃)—(CH₂)₄—N(CH₃)— | | —CH₂—C(O)—NH— | 2,6-dimethylphenyl |
| 200 | 2,6-dimethyl-4-(ethoxycarbonylmethyl)phenyl | —NH—C(O)—CH(C₂H₅)— | —N—(CH₂)₂—O—(CH₂)₂—N—<br>            |<br>      (CH₂)₂—O—(CH₂)₂ | | —CH(C₂H₅)—C(O)—NH— | 2,6-dimethylphenyl |
| 201 | 2,6-dimethyl-4-(ethoxycarbonylmethyl)phenyl | —NH—C(O)—CH(C₂H₅)— | —N—(CH₂)₂—O—(CH₂)₂—N—<br>            |<br>      (CH₂)₂—O—(CH₂)₂ | | —CH(C₂H₅)—C(O)—NH— | 2-methylphenyl |
| 202 | 2,6-dimethyl-4-phenoxyphenyl | —NH—C(O)—CH₂— | —N(CH₃)—(CH₂)₄—N(CH₃)— | | —CH₂—C(O)—NH— | 2,6-dimethylphenyl |
| 203 | 2-methyl-6-(methoxycarbonylvinyl)phenyl | —NH—C(O)—CH(C₂H₅)— | —N—(CH₂)₂—O—(CH₂)₂—N—<br>            |<br>      (CH₂)₂—O—(CH₂)₂ | | —CH(CH₃)—C(O)—NH— | 2-methylphenyl |
| 204 | 2-methyl-6-(methoxycarbonylethyl)phenyl | —NH—C(O)—CH(C₂H₅)— | —N—(CH₂)₂—O—(CH₂)₂—N—<br>            |<br>      (CH₂)₂—O—(CH₂)₂ | | —CH(CH₃)—C(O)—NH— | 2-methylphenyl |

Of the compounds numbered above, preferred compounds include numbers 131, 151, 190, 193, and 203.

Similarly, the following compounds of Formula I are prepared:

| # | Ar— | (Ar—W)¹ —W— | Linker -Linker- | (W—Ar)² —W— | —Ar |
|---|---|---|---|---|---|
| | 2,6-dimethyl-4-butoxyphenyl | —NH—C(O)—CH(C₂H₅)— | —NH—(CH₂)₂—O—(CH₂)₂—O—(CH₂)₂—N— | —CH(C₂H₅)—C(O)—NH | 2,6-dimethylphenyl |
| | 2-methylphenyl | —NH—C(O)—CH(CH₃)— | —N—(CH₂)₂—O—(CH₂)₂—O—(CH₂)₂—N— / (CH₂)₂—O—(CH₂)₂—O—(CH₂)₂ | —CH(C₂H₅)—C(O)—NH | 2,6-dimethyl-4-(carboxymethyl)phenyl |
| | 2,6-dimethylphenyl 2,6-dimethyl-6-n-butoxyphenyl | —NH—C(O)—C(CH₃)₂— —NH—C(O)—CH₂ | NH—(CH₂)₂—O—(CH₂)₂—O—(CH₂)₂—N— / —N(CH₃)—(CH₂)₄—N(CH₃)— | —C(CH₃)₂—NH—C(O)— —CH(CH₃)—NH—C(O)— | 2,6-dimethylphenyl 2,6-dimethylphenyl |
| | 2-methyl-6-methoxyphenyl | —NH—C(O)—CH(C₂H₅)— | —N—(CH₂)₂—O—(CH₂)₂—N— / (CH₂)₂—O—(CH₂)₂ | —CH(C₂H₅)—C(O)—NH | 2-methyl-6-methoxyphenyl |
| | 2,6-dimethyl-4-(ethoxycarbonylethyl)phenyl | —NH—C(O)—CH(C₂H₅)— | —N—(CH₂)₂—O—(CH₂)₂—N— / (CH₂)₂—O—(CH₂)₂ | —CH(C₂H₅)—C(O)—NH | 2-methylphenyl |
| | 2,6-dimethyl-4-(n-propoxycarbonylethyl)phenyl | —NH—C(O)—CH(C₂H₅)— | —N—(CH₂)₂—O—(CH₂)₂—N— / (CH₂)₂—O—(CH₂)₂ | —CH(C₂H₅)—C(O)—NH | 2-methylphenyl |
| | 2,6-dimethyl-4-(isopropoxycarbonylethyl)phenyl | —NH—C(O)—CH(C₂H₅)— | —N—(CH₂)₂—O—(CH₂)₂—N— / (CH₂)₂—O—(CH₂)₂ | —CH(C₂H₅)—C(O)—NH | 2-methylphenyl |
| | 2,6-dimethyl-4-(n-butoxycarbonylethyl)phenyl | —NH—C(O)—CH(C₂H₅)— | —N—(CH₂)₂—O—(CH₂)₂—N— / (CH₂)₂—O—(CH₂)₂ | —CH(C₂H₅)—C(O)—NH | 2-methylphenyl |
| | 2,6-dimethyl-4-(sec-butoxycarbonylethyl)phenyl | —NH—C(O)—CH(C₂H₅)— | —N—(CH₂)₂—O—(CH₂)₂—N— / (CH₂)₂—O—(CH₂)₂ | —CH(C₂H₅)—C(O)—NH | 2-methylphenyl |
| | 2,6-dimethyl-4-(t-butoxycarbonylethyl)phenyl | —NH—C(O)—CH(C₂H₅)— | —N—(CH₂)₂—O—(CH₂)₂—N— / (CH₂)₂—O—(CH₂)₂ | —CH(C₂H₅)—C(O)—NH | 2-methylphenyl |

| # | Ar— | —W— | -Linker- | —W— | —Ar |
|---|---|---|---|---|---|
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-benzyloxyphenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-(pyridin-2-ylmethoxy)phenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-[2-(pyridin-2-yl)ethoxy)]phenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-[3-(pyridin-2-yl)propoxy)phenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-[4-(pyridin-2-yl)butoxy)]phenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-phenoxyphenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-[pyridin-2-yloxy))phenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-[pyridin-4-yloxy)phenyl |
| | 2,6-dimethylphenyl | —NH—C(O)—CH$_2$— | —N(CH$_3$)—(CH$_2$)$_4$—N(CH$_3$)— | —CH$_2$—C(O)—NH— | 2,6-dimethyl-4-[pyridin-4-ylbutoxy)phenyl |
| | 2,6-dimethyl-4-ethoxy-phenyl | —NH—C(O)—CH$_2$— | —N(CH$_3$)—(CH$_2$)$_4$—N(CH$_3$)— | —CH$_2$—C(O)—NH— | 2,6-dimethylphenyl |
| | 2,6-dimethyl-4-(n-propoxy)phenyl | —NH—C(O)—CH$_2$— | —N(CH$_3$)—(CH$_2$)$_4$—N(CH$_3$)— | —CH$_2$—C(O)—NH— | 2,6-dimethylphenyl |
| | 2,6-dimethyl-4-(n-pentoxy)phenyl | —NH—C(O)—CH$_2$— | —N(CH$_3$)—(CH$_2$)$_6$—N(CH$_3$)— | —CH$_2$—C(O)—NH— | 2,6-dimethylphenyl |
| | 2,6-dimethyl-4-(t-butylcarbonyloxymethoxycarbonyl)phenyl | —NH—C(O)—CH$_2$— | —N(CH$_3$)—(CH$_2$)$_8$—N(CH$_3$)— | —CH$_2$—C(O)—NH— | -2,6-dimethylphenyl |
| 193 | 2,6-dimethylphenyl | —NH—C(O)—CH(C$_2$H$_5$)— | —N—(CH$_2$)$_2$—O—(CH$_2$)$_2$—N— <br>  (CH$_2$)$_2$—O—(CH$_2$)$_2$ | 2-methyl-3-(methoxycarbonylmethoxy) | -2,6-dimethylphenyl |
| 193 | 2,6-dimethylphenyl | —NH—C(O)—CH(C$_2$H$_5$)— | —N—(CH$_2$)$_2$—O—(CH$_2$)$_2$—N— <br>  (CH$_2$)$_2$—O—(CH$_2$)$_2$ | 2-methyl-3-(n-propoxycarbonylmethoxy) | |

Methods of Preparation of Compounds of Formula I

Linkers

The linker or linkers, when covalently attached to multiple copies of the ligands, provides a biocompatible, substantially non-immunogenic multi-binding compound. The biological activity of the multibinding $Na^+$ channel binding compound is highly sensitive to the geometry, composition, size, flexibility or rigidity, the presence or absence of anionic or cationic charge, the relative hydrophobicity/hydrophilicity, and similar properties of the linker. Accordingly, the linker is preferably chosen to maximize the biological activity of the multi-binding compound. The linker may be biologically "neutral," i.e., not itself contribute any biological activity to the multi-binding compound, or it may be chosen to enhance the biological activity of the compound. In general, the linker may be chosen from any organic molecule construct that orients two or more ligands to the receptors to permit multivalency. In this regard, the linker can be considered as a "framework" on which the ligands are arranged in order to bring about the desired ligand-orienting result, and thus produce a multi-binding compound.

For example, different orientations of ligands can be achieved by varying the geometry of the framework (linker) by use of mono- or polycyclic groups, such as aryl and/or heteroaryl groups, or structures incorporating one or more carbon—carbon multiple bonds (alkenyl, alkenylene, alkynyl or alkynylene groups). The optimal geometry and composition of frameworks (linkers) used in the multi-binding compounds of this invention are based upon the properties of their intended receptors. For example, it may be preferred in some cases to use rigid cyclic groups (e.g., aryl, heteroaryl), or in other cases non-rigid cyclic groups (e.g., cycloalkyl or crown groups) to reduce conformational entropy when desired.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines" (class of surfactants).

Different frameworks can be designed to provide preferred orientations of the ligands. The identification of an appropriate framework geometry for ligand domain presentation is an important first step in the construction of a multibinding agent with enhanced activity. Systematic spatial searching strategies can be used to aid in the identification of preferred frameworks through an iterative process. FIG. 5 illustrates a useful strategy for determining an optimal framework display orientation for ligand domains and can be used for preparing the bivalent compounds of this invention. Various alternative strategies known to those skilled in the art of molecular design can be substituted for the one described here.

As shown in FIG. 5, the ligands (shown as filled circles) are attached to a central core structure such as phenyldiacetylene (Panel A) or cyclohexane dicarboxylic acid (Panel B). The ligands are spaced apart from the core by an attaching moiety of variable lengths m and n. If the ligand possesses multiple attachment sites (see discussion below), the orientation of the ligand on the attaching moiety may be varied as well. The positions of the display vectors around the central core structures are varied, thereby generating a collection of compounds. Assay of each of the individual compounds of a collection generated as described will lead to a subset of compounds with the desired enhanced activities (e.g., potency, selectivity). The analysis of this subset using a technique such as Ensemble Molecular Dynamics will suggest a framework orientation that favors the properties desired.

The process may require the use of multiple copies of the same central core structure or combinations of different types of display cores. It is to be noted that core structures other than those shown here can be used for determining the optimal framework display orientation of the ligands. The above-described technique can be extended to trivalent compounds and compounds of higher-order valency.

A wide variety of linkers are commercially available (see, e.g., Chem Sources USA and Chem Sources International; the ACD electronic database; and Chemical Abstracts). Many of the linkers that are suitable for use in this invention fall into this category. Others can be readily synthesized by methods known in the art, and as described below. Examples are given below and in FIG. 4, but it should be understood that various changes may be made and equivalents may be substituted without departing from the true spirit and scope of the invention.

For example, properties of the linker can be modified by the addition or insertion of ancillary groups into the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto the linker enhances the hydrophilicity and water solubility of the multibinding compound, increases both molecular weight and molecular size and, depending on the nature of the unPEGylated linker, may increase the in vivo retention time. Further, PEG may decrease antigenicity and potentially enhances the overall rigidity of the linker.

Ancillary groups that enhance the water solubility/hydrophilicity of the linker, and accordingly, the resulting multibinding compounds, are useful in practicing this invention. Thus, it is within the scope of the present invention to use ancillary groups such as, for example, small repeating units of ethylene glycols, alcohols, polyols, (e.g., glycerin, glycerol propoxylate, saccharides, including mono-, oligosaccharides, etc.) carboxylates (e.g., small repeating units of glutamic acid, acrylic acid, etc.), amines (e.g., tetraethylenepentamine), and the like to enhance the water solubility and/or hydrophilicity of the multibinding compounds of this invention. In preferred embodiments, the ancillary group used to improve water solubility/hydrophilicity will be a polyether. In particularly preferred embodiments, the ancillary group will contain a small number of repeating ethylene oxide (—$CH_2CH_2O$—) units.

The incorporation of lipophilic ancillary groups within the structure of the linker to enhance the lipophilicity and/or hydrophobicity of the compounds of Formula I is also within the scope of this invention. Lipophilic groups useful with the linkers of this invention include, but are not limited to, lower alkyl, aromatic groups and polycyclic aromatic groups. The aromatic groups may be either unsubstituted or substituted with other groups, but are at least substituted with a group which allows their covalent attachment to the linker. As used herein the term "aromatic groups" incorporates both aromatic hydrocarbons and heterocyclic aromatics. Other lipophilic groups useful with the linkers of this invention include fatty acid derivatives which may or may not form micelles in aqueous medium and other specific lipophilic groups which modulate interactions between the multibinding compound and biological membranes.

Also within the scope of this invention is the use of ancillary groups which result in the compound of Formula I being incorporated into a vesicle, such as a liposome, or a micelle. The term "lipid" refers to any fatty acid derivative that is capable of forming a bilayer or micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidylethanolamine, dipalmitoylphosphatidylcholine, dioleoylphosphatidylcholine, distearoyl-phosphatidylcholine and dilinoleoylphosphatidylcholine. Other compounds lacking phosphorus, such as sphingolipid and glycosphingolipid families, are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker, or bonds between the linker and the ancillary group(s), or bonds between the linker and the ligands. Rigid groups can include, for example, those groups whose conformational freedom is restrained by the presence of rings and/or π-bonds, for example, aryl, heteroaryl, heterocyclic, alkenylene and alkynylene groups. Other groups that can impart rigidity include polypeptide groups such as oligo-or polyproline chains.

Rigidity can also be imparted electrostatically. Thus, if the ancillary groups are either positively or negatively charged, the similarly charged ancillary groups will force the linker into a configuration affording the maximum distance between each of the like charges. The energetic cost of bringing the like-charged groups closer to each other, which is inversely related to the square of the distance between the groups, will tend to hold the linker in a configuration that maintains the separation between the like-charged ancillary groups. Further, ancillary groups bearing opposite charges will tend to be attracted to their oppositely charged counterparts and potentially may enter into both inter- and intramolecular ionic bonds. This non-covalent mechanism will tend to hold the linker in a conformation which allows interaction between the oppositely charged groups. The addition of ancillary groups which are charged, or alternatively, protected groups that bear a latent charge which is unmasked, following addition to the linker, by deprotection, a change in pH, oxidation, reduction or other mechanisms known to those skilled in the art, is within the scope of this invention.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon π/bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity (entropic control) is imparted by the presence of alicyclic (e.g., cycloalkyl), aromatic and heterocyclic groups. In other preferred embodiments, this comprises one or more multi-membered rings (e.g., 6-membered rings). In still further preferred embodiments, the ring is an aryl group such as, for example, phenyl or naphthyl, or a macrocyclic ring such as, for example, a crown compound.

In view of the above, it is apparent that the appropriate selection of a linker group providing suitable orientation, entropy and physico-chemical properties is well within the skill of the art.

Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

Preparation of Bivalent Compounds of Formula I

As indicated above, the preferred compounds of Formula I are bivalent compounds which can be represented as L—X—L, where L is a ligand that is the same or different at each occurrence, and X is the linker. Accordingly, examples of bivalent compounds of Formula I may be prepared as described below, with reference to FIGS. 6–14 which illustrate Reaction Schemes A to T. It should be noted, however, that the same techniques can be used to generate higher order multibinding compounds, i.e., the compounds of the invention where p is 3–10 (see, e.g., Scheme S in FIG. 13). The substituent groups and linker components illustrated in Schemes A to P of FIGS. 6–10 (e.g., $R^1$, $R^2$, Z, etc.) have the same meanings as described in the Summary of the Invention, unless otherwise specified.

A simplification in the description of the preparations is where a compound is represented by a formula containing a linking group such as an alkylene chain—$(CH_2)_m$— (e.g., compounds (9) and (10) in Scheme C). It should be understood that—$(CH_2)_m$— is not intended to signify or imply that the scope of this reaction (or of the invention) is limited to straight (i.e. unbranched) alkylene chains, but rather —$(CH_2)_m$— is intended to include branched alkylenes, substituted alkylenes, and the like, as defined and disclosed herein.

Unless specified to the contrary, the solvents used in the reactions of the present invention are inert organic solvents as defined herein.

The reactions described therein take place at atmospheric pressure within a temperature range of from 5° C. to 100° C., preferably from 10° C. to 50° C., most preferably at "room" or "ambient" temperature, e.g., 20° C., but the preferred temperature ranges will be those where the reagents will react within a reasonable period, preferably less than 12 hours, unless specified to the contrary. Further, unless otherwise specified, the reaction times and conditions are intended to be approximate. Parameters given in the Examples are intended to be specific, not approximate.

Reactions performed under standard amide coupling conditions are carried out in an inert polar solvent (e.g., DMF, DMA) in the presence of a hindered base (e.g., TEA, DIPEA) and standard amide coupling reagents (e.g., DPPA, PyBOP, HATU, DCC).

Preparation of Compounds of Formulae Ia. Ib and Ic

As described previously, the compounds of Formula Ia, Ib and Ic represent subgenera of bivalent compounds of Formula I, in which X is respectively a linker of Formula II, III and IV (as defined in the Summary of the Invention).

Figure 6:
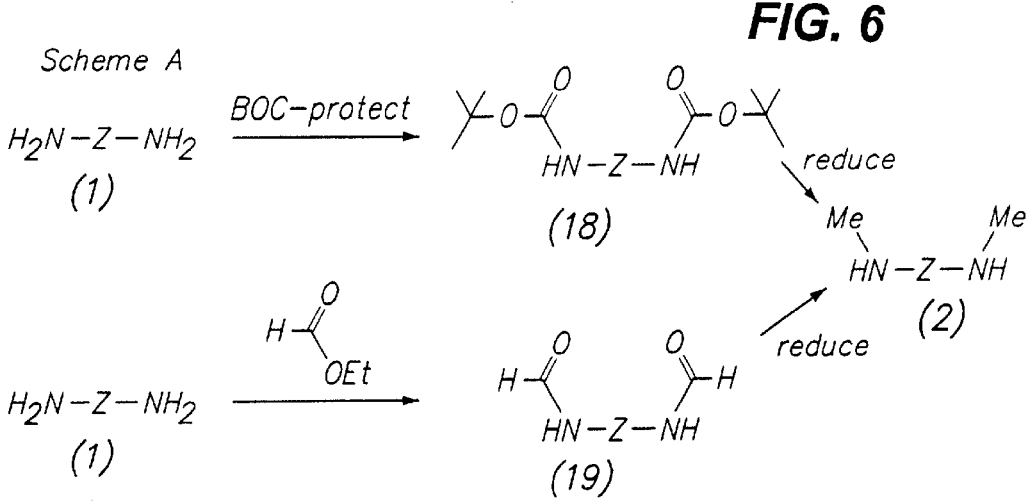
Figure 6:
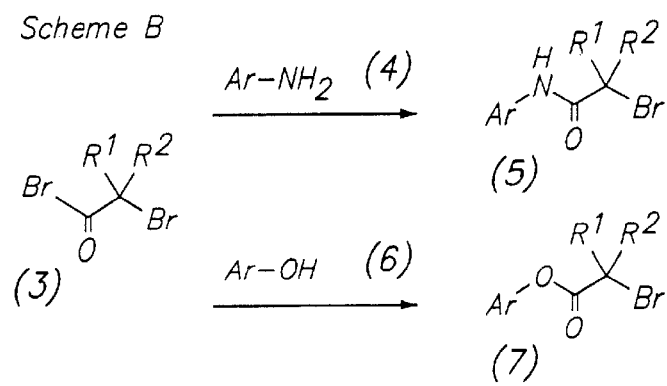
Figure 6:
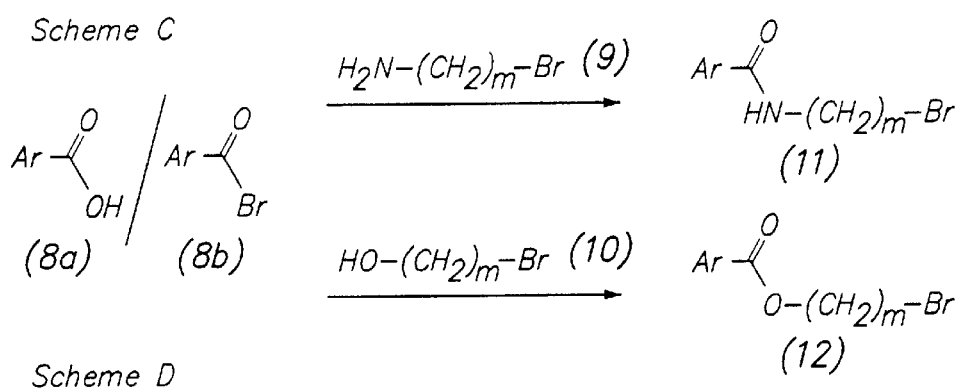

The preparation of ligand precursors for use in preparing compounds of Formulae Ia, Ib and Ic, and of linkers used in compounds of Formula Ia, is illustrated in Reaction Schemes A through D (FIG. 6).

Preparation of Linkers

Starting materials—In general, the diamine and dihalide linkers that are used in preparing the compounds of Formula Ia are commercially available or can be prepared by conventional methods known to those of ordinary skill in the art of synthetic organic chemistry.

Formula (2)—The preparation of a compound of formula (2) from a primary diamine is shown in Scheme A. A primary diamine (1) is dissolved under nitrogen in an inert organic solvent such as dichloromethane and is stirred at room temperature with a Boc protecting agent (e.g., $Boc_2O$) for several hours until the reaction is complete, to yield a di-Boc-protected diamine (18). Alternatively, diamine (1) is reacted with ethyl formate under standard conditions to yield a diformamide (19). The acylated products (18) or (19) are collected by precipitation and filtration and are reduced under nitrogen to the N,N'-methyl diamine (2), using a suitable reducing agent in an inert organic solvent (e.g., $LiAlH_4$ in dry THF). When reduction is complete, the solution is quenched (e.g., with $Na_2SO_4$ decahydrate solution), and compound (2) is isolated by filtration and evaporation of solvent.

Preparation of Ligand Precursors

Starting materials—α-halo acid halides (3), anilines (4), phenols (6) and benzoic acids or their acid halide derivatives (8) are commercially available. It is preferred that compounds (4), (6), and (8) are substituted on the aryl group with one or more substituents as described herein (for examples, see Definitions, Examples and Table 2). For the preparation of benzoate ester derivatives of formula (5), the preferred starting material is an aminobenzoic acid. Esterification of the acid group is typically carried out prior to use of the starting material in the synthesis of formula (5).

Formula (5)—Compounds of formula (5) are prepared as shown in Scheme B. An α-halo acid halide (3) is reacted under nitrogen with an aniline (4). It will be recognized that in preparing those compounds of formula (5) where $R^1$ and/or $R^2$ are other than hydrogen, the bromo acid halide derivative of compounds of formula (3) is preferred, rather than the chloro derivative.

The addition of the halide is carried out with cooling in an inert organic solvent (e.g., dichloromethane) in the presence of a suitable base (e.g., DIPEA) to scavenge the acid generated. The reaction is thereafter continued at room temperature for approximately an hour, then the reaction mixture is concentrated and washed with ether to yield an α-halo amide (5).

Formula (7)—Compounds of formula (7) are prepared as shown in Scheme B by reacting a compound of formula (3) with a phenol (6) to yield an α-halo ester (7). The reaction is carried out under nitrogen with cooling in an inert organic solvent (e.g., dichloromethane) in the presence of a suitable base (e.g., DIPEA), then partitioned into ether and water. The ether phase is collected, and rinsed with water, brine, dried ($MgSO_4$), filtered, concentrated and purified by chromatography to yield an α-halo ester (7).

Formula (1)—ω-halo benzylamide compounds of formula (11) are prepared as shown in Scheme C, by reacting a benzoic acid (8a) under standard amide coupling conditions to an ω-halo-amine (9), where $m \leq 10$ and preferably not 4 or 5, to yield amide (11). Benzoic acids are coupled using standard amide coupling reactions. Preferably, a hindered base is employed, preferably diisopropylethylamine, in the presence of benzotriazol-1-yloxytripyrrolidino phosphonium hexafluorophosphate (PyBOP) and 1-hydroybenzotriazole (HOBT). The reaction is conducted in an inert polar solvent, for example, N,N-dimethylformamide (DMF) or dimethyl sulfoxide (DMSO), or preferably a mixture of both, at about room temperature.

Formula (12)-ω-halo benzylester compounds of formula (12) are prepared as shown in Scheme C, by reacting an appropriately substituted benzoyl halide compound (8b) with an ω-halo alcohol (10), where $m \leq 10$ and preferably not 4 or 5, in the presence of a nonnucleophilic base (e.g. pyridine) in an inert solvent (e.g. ether) to yield a precipitate. The crude product is redissolved in ether, water soluble impurities are removed by washing, and the ether layer is concentrated to yield ω-halo benzylester (12).

Formula (16)—The preparation of ligand precursors with alkyl ether sidechain substitutions of the aryl group, i.e., compounds of Formula (16) where $R^{10}$ is an alkyl group typically having one or more carbon atoms is shown in Scheme D. Nitrophenol (13) is prepared by reacting an appropriately substituted phenol with sodium nitrate as described in Example 5 below. Nitrophenol (13) is reacted under a nitrogen atmosphere in an inert solvent (e.g., DMF) with an alkyl halide in the presence of base (e.g., potassium carbonate) for about 12 hours to yield nitro-substituted arylether (14). Compound (14) is extracted from the reaction mixture into ethyl acetate/hexanes (1:1 v/v) and concentrated. Catalytic hydrogenation of compound (14) yields amine (15). After removal of the catalyst by filtration, the filtrate is concentrated to provide amine (15). Amine (15) is dissolved in an inert solvent (e.g., dichloromethane), then coupled in the presence of DIPEA to α-halo acid halide (3) to yield (16). Compound (16) is isolated by organic phase extraction and concentration.

Compounds of Formula Ia

Figure 7:
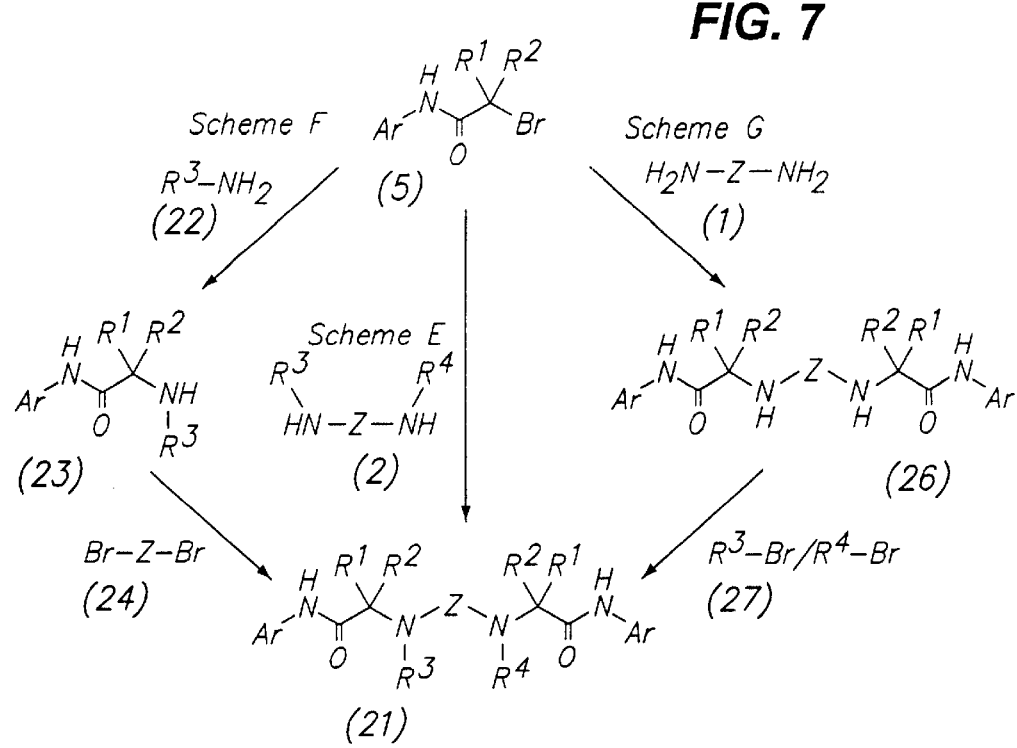
Figure 7:
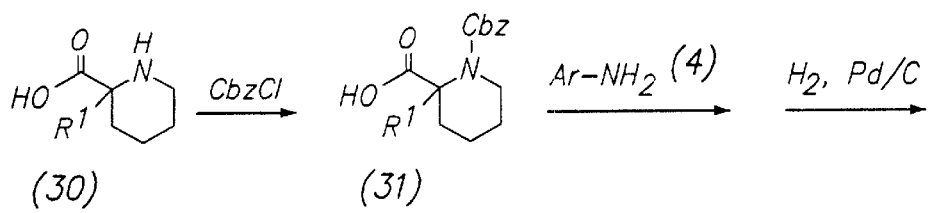
Figure 7:
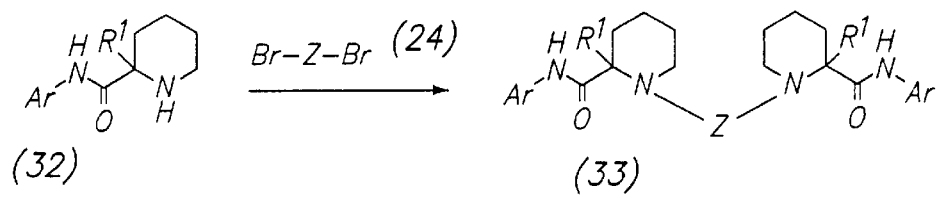
Figure 8:
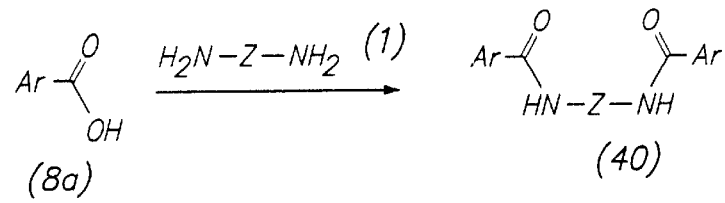
Figure 8:
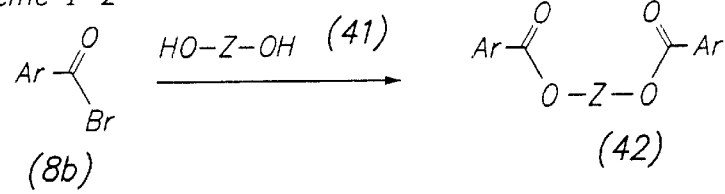
Figure 8:
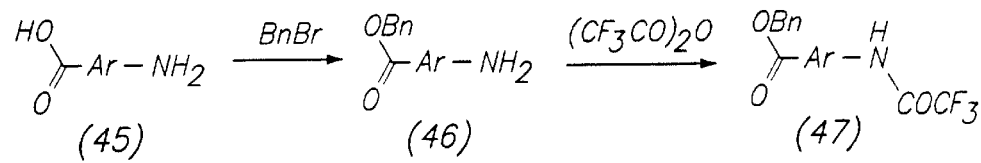
Figure 8:
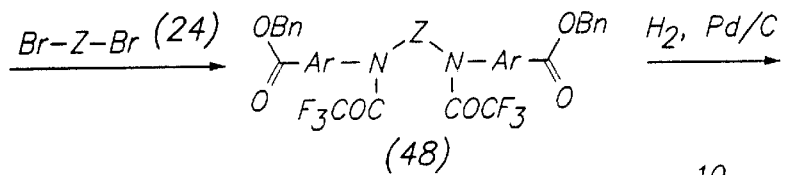
Figure 8:
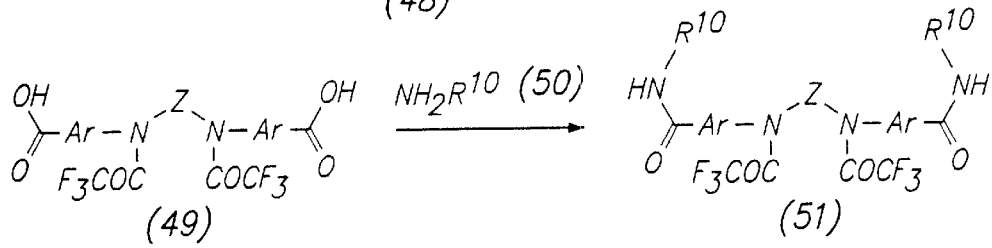
Figure 8:
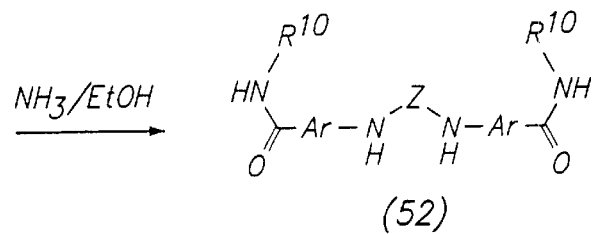

The preparation of compounds of Formula Ia is illustrated in Reaction Schemes E through J of FIGS. 7 and 8.

Formula (21)—A compound of Formula Ia represented by formula (21), is preferably prepared by Scheme E (where $R^3$ and $R^4$ may be the same or different substitutents) or G (where $R^3$ and $R^4$ are the same substituent). In Scheme E, approximately 2 equivalents of an appropriately substituted α-halo amide (5), one equivalent of linker (2) and 2.5 equivalents of base (e.g.,DIPEA) are dissolved in an inert organic solvent (e.g., ethanol) under a nitrogen atmosphere and refluxed at about 85° C. until the reaction is complete. The bivalent compound of formula (21) is isolated by crystallization from the reaction mixture at room temperature.

An alternate route is shown in Scheme G. The first step is carried out with a linker of formula (1) essentially as described above for Scheme E to yield a compound of Formula Ia represented by formula (26). In the next step, one equivalent of (26) is dissolved in alcohol and refluxed for about 12 hours under a nitrogen atmosphere with approximately two equivalents of alkyl halide (27) to yield a compound of Formula Ia represented by formula (21). Compound (21) is purified by chromatography (e.g., silica gel), converted to an acid salt and and precipitated from an organic solvent.

Another possible route for preparing compound (21) is shown in Scheme F of FIG. 7. According to Scheme F of FIG. 7, compound (5) is coupled to a primary alkylamine (22) in the presence of base to yield a compound of formula (23). Compound (23) is then coupled with a dihalide linker

(24) in the presence of base to yield compound (21). Using a variation of Scheme F (see, e.g., Preparation of Bivalent Heterovalomers), compounds of Formula Ia can be synthesized where $R^3 \neq R^4$ Formula (33)—Compounds of Formula Ia having the structure of Formula (33) are prepared according to Scheme H of FIG. 7. Accordingly, a pipecolinic acid derivative (30) is reacted with an amine-protecting group (e.g., Cbz) under standard conditions to form an N-protected compound of formula (31). Compound (31) is reacted under nitrogen with an equivalent of suitably substituted aniline (4) under standard amide coupling conditions. The amide product is deprotected by catalytic hydrogenation, and following removal of the catalyst by filtration, the deprotected amide (32) is concentrated. Two equivalents of compound (32) is reacted under nitrogen with one equivalent of a dihalide linker (24) in the presence of base at 80° C. for about 12 hours. A compound of Formula Ia represented by formula (33) is isolated from the reaction mixture by preparative HPLC, followed by lyophilization.

Formula (40)—Compounds of Formula Ia having the structure represented by formula (40) are prepared as illustrated in Scheme I-1 of FIG. 8. Approximately two equivalents of an appropriately substituted benzoic acid (8a) is reacted overnight in an inert organic solvent (e.g., DMF) under a nitrogen atmosphere and under standard amide coupling conditions with approximately one equivalent of linker (1). The product, compound (40) is purified by preparative HPLC.

Formula (52)—Compounds of Formula Ia having the structure represented by formula (52) are prepared as illustrated in Scheme J of FIG. 8. An aminobenzoic acid compound (45) is dissolved in a polar solvent (e.g., acetonitrile) under nitrogen and is reacted at elevated temperature (e.g., 90° C.) with a carboxy-protecting agent such as benzyl bromide to yield a compound of formula (46).

Compound (46) is dissolved in an inert organic solvent (e.g., ether) and is reacted under nitrogen with an amine-protecting group (e.g., trifluoroacetic anhydride, 20° C.) for several hours, then concentrated to yield a compound of formula (47).

Approximately two equivalents of compound (47) is coupled with one equivalent of a dihalide (24) by refluxing with base and a catalyst (e.g., benzyltriethyl ammonium chloride) in an inert solvent for about 48 hours, then concentrated and purified (e.g., by silica gel chromatography) to yield a compound of formula (48). Compound (48) is deprotected at the COOH group to yield (49). Amide coupling with amine (50) (where $R^{10}$ is alkylene or substituted alkylene, preferably dialkylaminoalkyl) is carried out at room temperature for several days under nitrogen under standard coupling conditions to yield compound (51), which, after concentration and purification (e.g., by chromatography) is N-deprotected to yield a compound of Formula Ia having the structure represented by formula (52).

Compounds of Formula Ib

Figure 9:
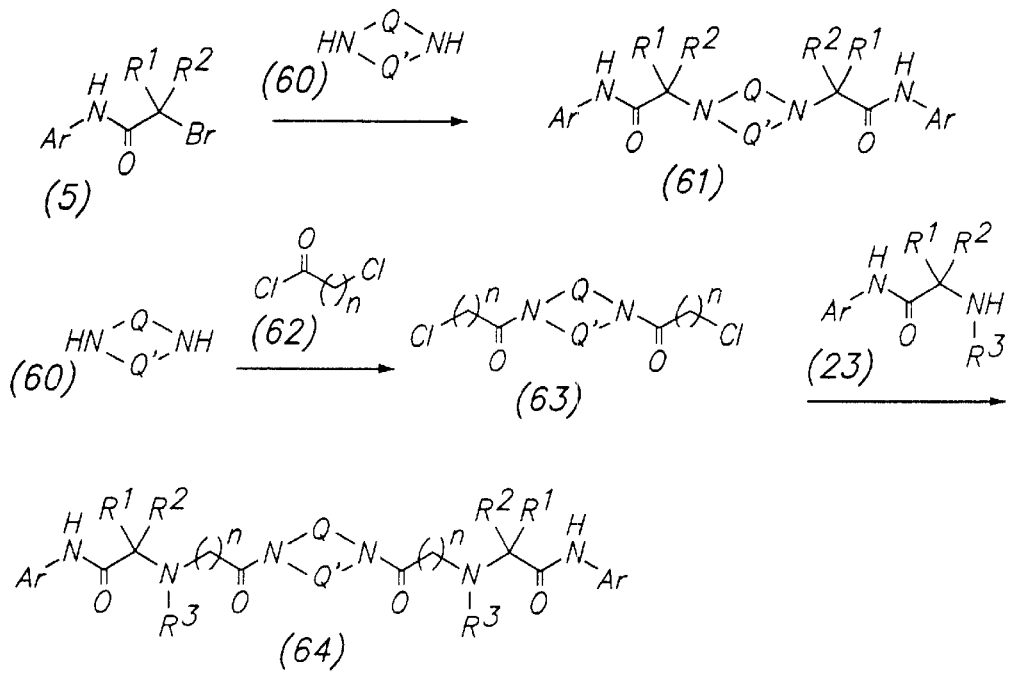
Figure 9:
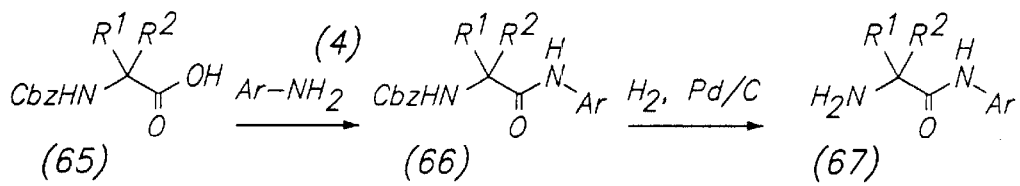
Figure 9:
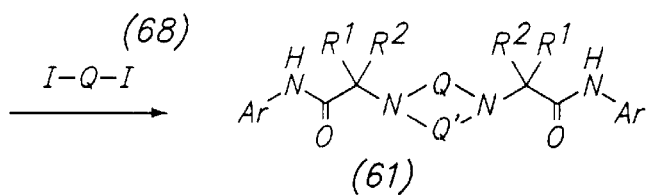

Reaction Schemes K-M of FIG. 9 illustrate the preparation of compounds of Formula Ib having cyclic secondary amine linkers of the formula shown below,

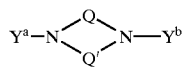

where Q and Q' may be the same or different alkylene or substituted alkylene chains (preferably oligoethylene glycol chains), and $Y^a$ and $Y^b$ may be the same or different and are defined as in the Summary of the Invention.

The preparation of a compound of Formula Ib where linker X is a piperazine group is described below in Example 13B.

Although not shown here, it should be understood that those compounds of Formula Ib with linkers comprising multiple N-containing heterocyclic rings can be prepared by reactions analogous to those shown in Schemes K-M of FIG. 9.

Starting materials—In general, the cyclic secondary amine linkers that are used in preparing the compounds of Formula Ib are commercially available or can be prepared by methods known to those of ordinary skill in the art of synthetic organic chemistry.

Formula (61)—Compounds of Formula Ib having the structure represented by formula (61) are prepared as illustrated in Scheme K of FIG. 9.

Approximately one equivalent of a compound of formula (60) is dissolved in alcohol and refluxed under nitrogen with approximately 2.5 equivalents of an electrophilic precursor (5) in the presence of a hindered base (e.g., DIPEA) for about a week to yield a compound of Formula Ib having the structure of formula (61). Compound (61) is isolated by organic extraction and purified by chromatography (e.g., on silica gel).

An alternative synthesis of a compound of formula (61) is shown in Scheme M of FIG. 9. It will be recognized that the use of a chiral amino acid (65) affords stereoselective synthesis of compound (61). As shown in Scheme M, N-protected amino acid (65) is coupled under nitrogen and under standard amide coupling conditions (e.g., HATU, HOAt, DIPEA in DMF) to aniline (4) to form compound (66). Compound (66) is deprotected (e.g., by catalytic hydrogenation) to form compound (67). Compound (67) is concentrated, dissolved in ethanol under nitrogen and two or more equivalents is reacted with an equivalent of dihalide (68), where Q is preferably alkylene or substituted alkylene, for several days in the presence of base at elevated temperature (e.g., 75° C.) to yield compound (61) after conventional isolation and purification (e.g., concentration and silica gel chromatography).

It should be noted also that Scheme M can be used to prepare chiral compounds of Formula Ia (e.g., by linking a chiral compound (67) to an alkyl halide).

Formula (64)—Compounds of Formula Ib having the structure represented by formula (64) are prepared according to Scheme L of FIG. 9.

Approximately 1 equivalent of Compound (60) is reacted with cooling with approximately 2 equivalents of a halogen-substituted acyl chloride (62), which is commercially available or otherwise prepared by methods known in the art. The resulting intermediate (63) is refluxed for several days under nitrogen with approximately 2.5 equivalents of compound (23) (prepared as shown in Scheme F of FIG. 7), then isolated and purified by conventional methods (e.g., organic phase extraction and silica gel chromatography) to yield compound (64).

Formula (42)—Compounds of Formula Ib having the structure represented by formula (42) are prepared according to Scheme 1-2 of FIG. 8. Two or more equivalents of an appropriately substituted benzoyl halide (8b) (e.g., chloride) are coupled to an equivalent of diol linker (41) in the presence of nonnucleophilic base (e.g. pyridine) in an inert solvent (e.g., THF, dichloromethane) to form a bivalent compound having the structure of formula (42). Compound (42) is purified by chromatography (e.g., silica gel).

Figure 14:
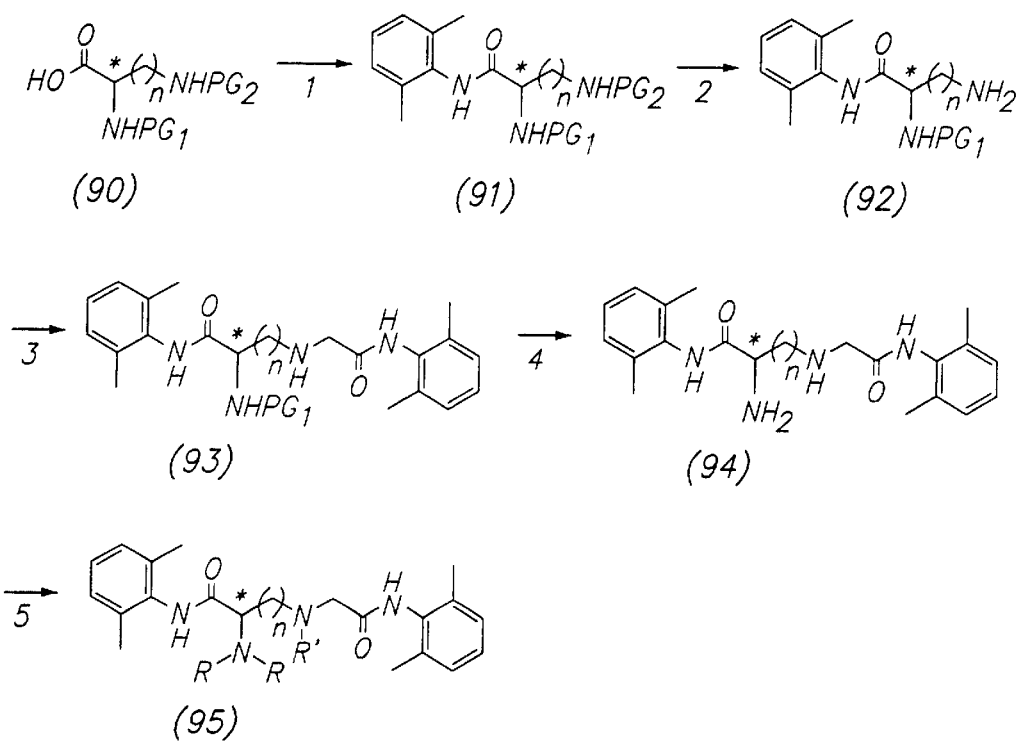

Formula (95)—Compounds of Formula Ib having the structure represented by formula (95) (where R and $R^1$ are alkyl groups, which may be the same or different, n=1–10, preferably 2–5, and the chiral center is denoted by an asterisk) are prepared according to Scheme T of FIG. 14. It should be understood that the aryl groups shown here are for illustrative purposes and are not intended to limit the scope of the invention.

Referring to Scheme T, a diaminoacid compound of formula (90) (where PG, and $PG_2$ are differentially removed N-protecting groups (e.g., Boc and Cbz or Boc and Fmoc)) is coupled with an aryl group (e.g., 2,6-dimethylaniline) (not shown) under standard amide coupling conditions (e.g., HATU, HOAT, DIPEA) to form a compound of formula (91). Compounds of formula (90) having $n \leq 5$ are commercially available, whereas compounds with n>5 can be synthesized by conventional well-known methods.

The compound of formula (91) is converted to a compound of formula (92) by removal of the $PG_2$ group as follows, for example,: where $PG_1$ is Boc and $PG_2$ is Fmoc, the compound is incubated with piperidine in DMF; where $PG_1$ is Boc and $PG_2$ is Cbz, the compound is treated with $H_2$ in the presence of 10% Pd/C catalyst; and when $PG_1$ is Fmoc and $PG_2$ is Boc, the compound is treated with TFA in dichloromethane.

A compound of formula (92) is alkylated by a compound of formula (5) (Scheme B) at elevated temperature (e.g., 80° C.) in the presence of base (e.g., DIPEA), to afford a compound of formula (93), which is purified by chromatography (e.g., silica gel).

Deprotection of a compound of formula (93) is carried out by treatment with piperidine in DMF (Fmoc removal), or by treatment with TFA in dichloromethane (Boc removal) for example, thus yielding a compound of formula (94). Compounds of formula (94) are optionally alkylated (by reductive alkylation or direct alkylation) to form compounds of formula (95).

Alternatively, alkylation can be carried out after Step 3 and before Step 4, and the alkylated product isolated by chromatography (e.g., silica gel). Following deprotection to remove $PG_1$, the deprotected amino group is then alkylated. This procedure is used for example to synthesize compounds of formula (95) where R≠R'.

Compounds of Formula Ic

Figure 10:
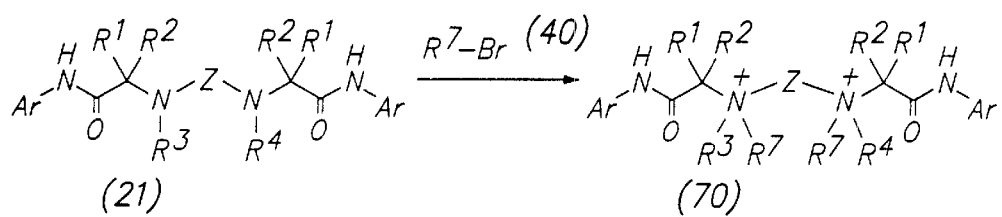
Figure 10:
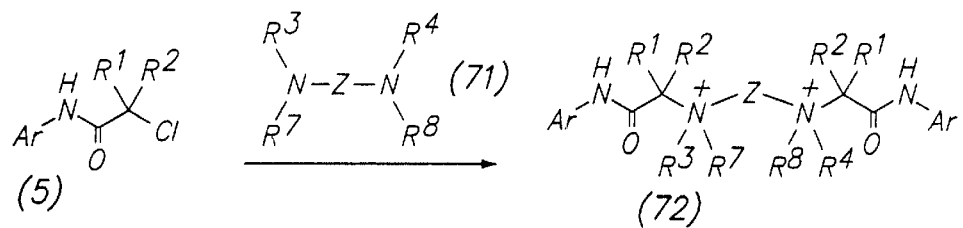
Figure 10:
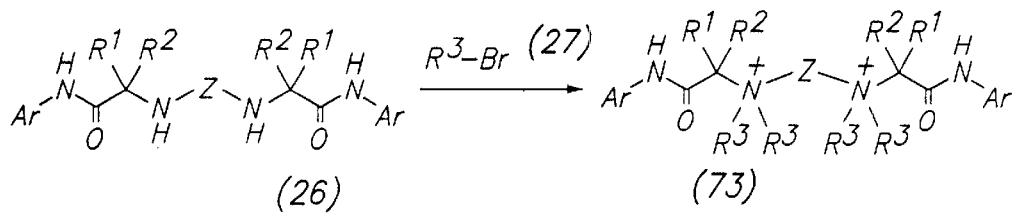

The preparation of compounds of Formula Ic (i.e., bivalent compounds having a bis-quaternary amine linker) is shown in Schemes N to P of FIG. 10.

Formula (70)—Compounds of formula (70) are prepared preferably as shown in Scheme N, where $R^3$, $R^4$ and $R^7$ may be the same or different. A compound of formula (21) (prepared according to Schemes E-G of FIG. 7), is reacted with an excess of alkylating agent (40) in the presence of base at elevated temperature (e.g. 85° C.) for about 24 hours, to yield a compound of formula (70).

Formula (72)—Compounds of formula (72) can be prepared by coupling two or more equivalents of ligand precursor (5) to an equivalent of tertiary amine linker (71) in the presence of base to yield a compound of formula (72).

Formula (73)—Compounds of formula (73) are prepared by reacting a compound of formula (26) (prepared as described in Scheme G of FIG. 7) with excess alkylating agent (27) in the presence of base to yield a compound of formula (73).

It is understood that altering reaction stoichiometries and conditions will yield a mixed quaternary/tertiary amine of the formula,

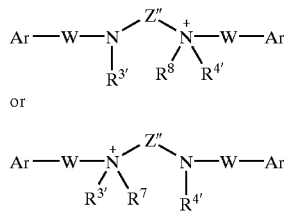

Such compounds are covered by Formula IV, wherein one of $R^7$ or $R^8$ is not present.

Preparation of Bivalent Heterovalomers

Heterovalomers (i.e., multibinding compounds with non-identical ligands) are prepared for example by the following methods.

Method 1: Synthesis of a monoadduct (i.e., linker-ligand conjugate) followed by coupling to a nonidentical ligand.

Figure 11:
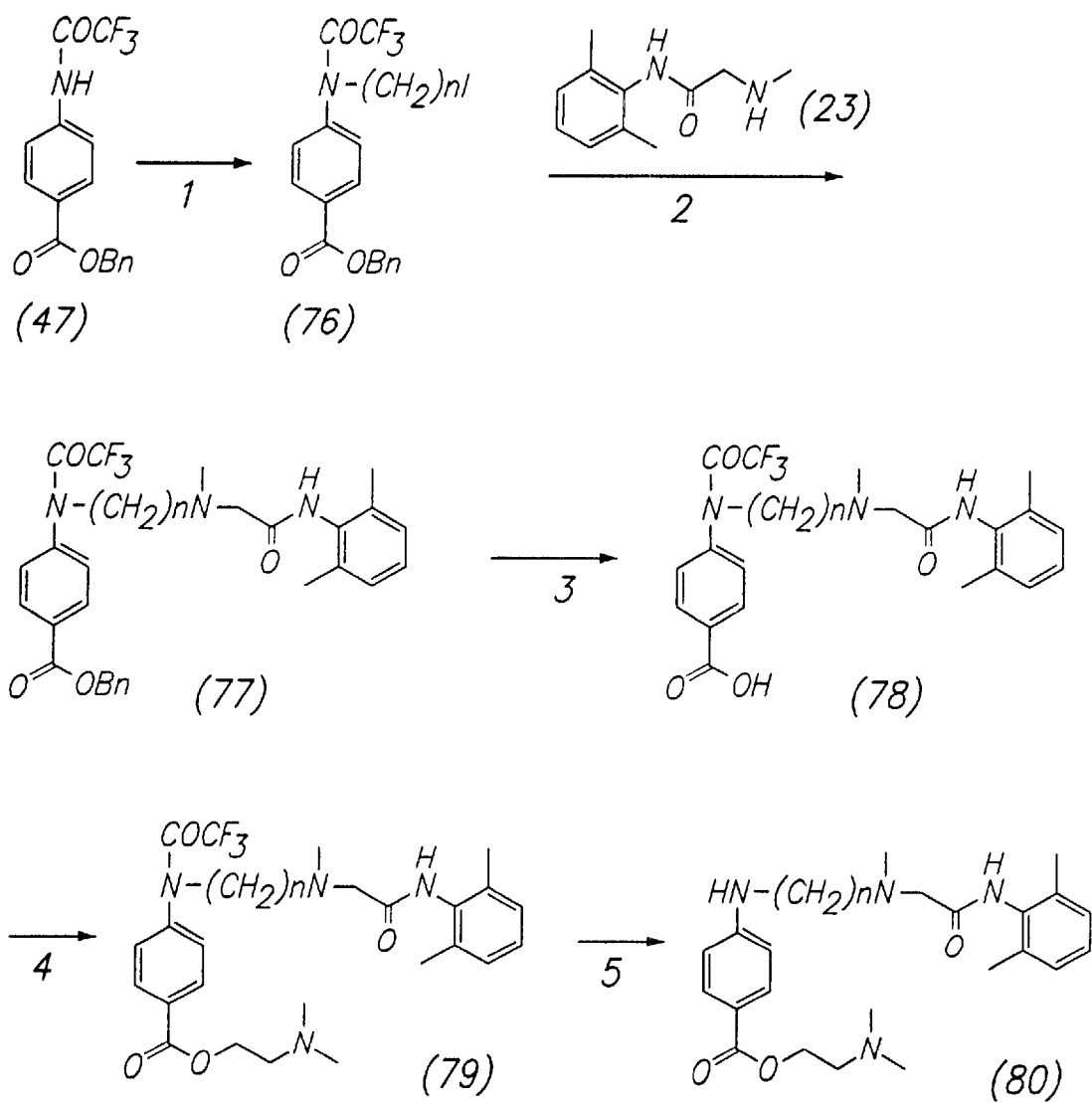
Figure 12:
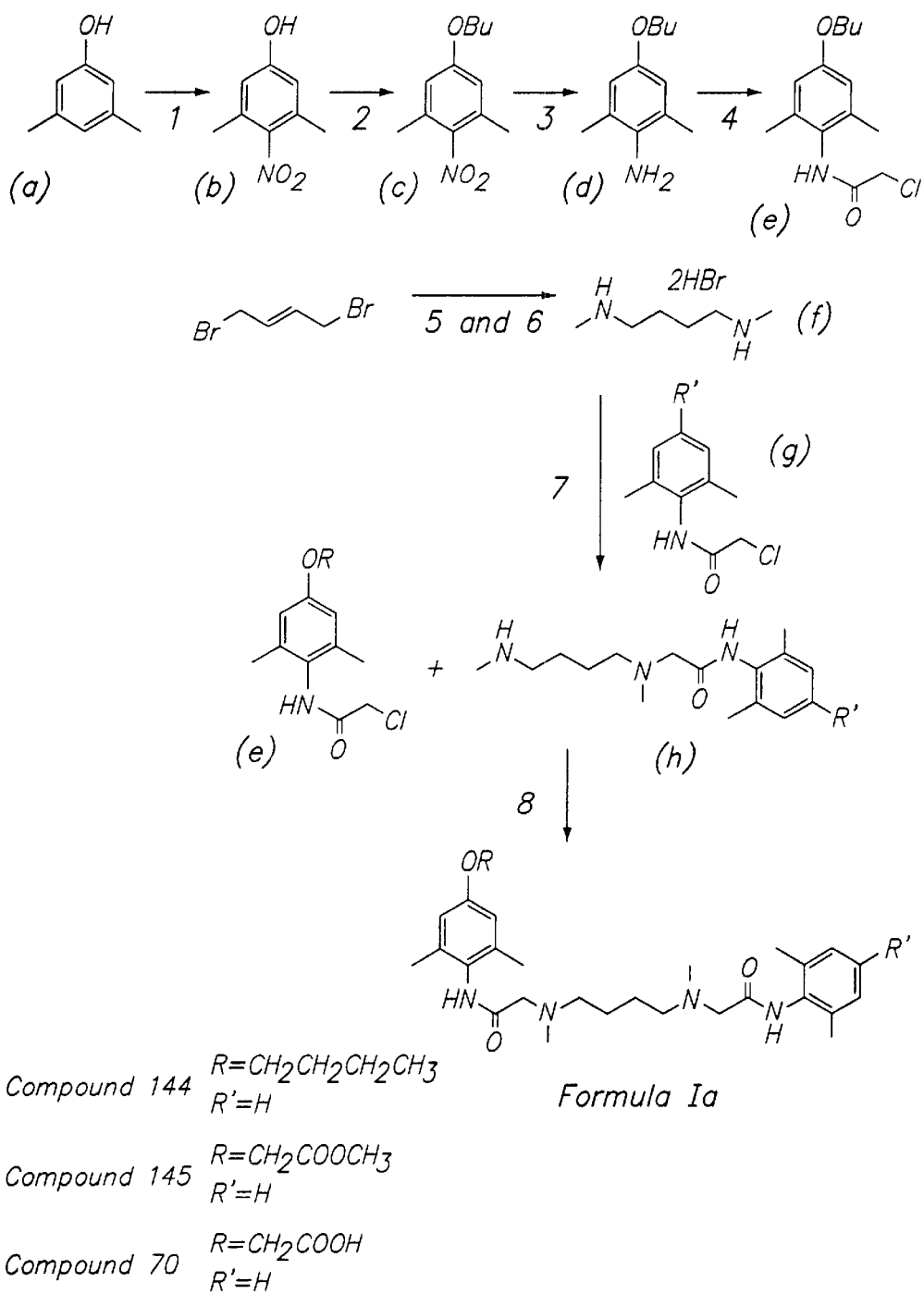
Figure 13:
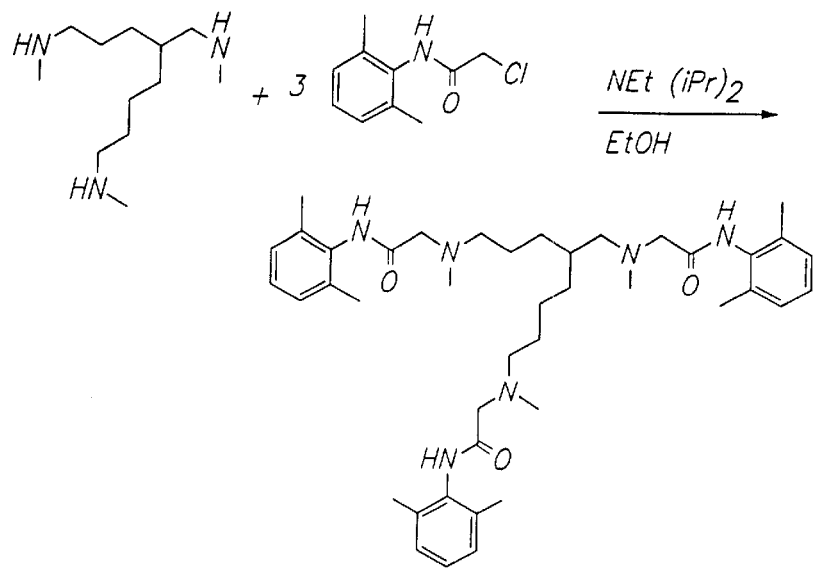

The preparation of Aryl-N linked heterovalomers having the structure represented by formula (80) is shown, for example, in Scheme Q of FIG. 11.

Formula (80)—A compound of formula (47) (prepared as described in Scheme J of FIG. 7), is reacted with five equivalents of a dihalide such as di-iodoalkane, under reflux with base and a catalyst (e.g., triethylbenzylammonium bromide) in an inert organic solvent overnight, then concentrated and purified (e.g., by silica gel chromatography) to yield a compound of formula (76). Compound (76) is reacted with two equivalents of a compound of formula (23) (prepared for example as shown in Scheme F of FIG. 7) in the presence of base in an organic solvent at about 60° C. with stirring overnight to afford a compound of formula (77) which is concentrated and purified chromatographically (e.g., silica gel). Compound (77) is deprotected at the carboxy group to yield (78). Compound (78) is esterified by reaction with N,N-dimethylethanolamine in the presence of DIPEA, HATU and HOAT to form a compound of formula (79), which is purified by chromatography (e.g., silica gel).

Deprotection of compound (79) is carried out by reaction with methylamine in THF to afford an (N-Aryl) heterovalomer of formula (80), which is purified by chromatography (e.g., silica gel).

Method 2: Isolation of monoadduct from dimerization reactions

A side product of the previously described dimerization reactions is the monoadduct (i.e., linker-ligand conjugate), which can be separated from the dimer by conventional chromatographic techniques. The stoichiometry of the reaction can be adjusted to favor production of the monoadduct (e.g., a 1:1 molar ratio of linker to ligand).

A monoadduct comprising one type of ligand can be coupled to a different ligand using essentially the same reaction conditions as described above with reference to Schemes E-M of FIGS. 7–9. This method is illustrated in Scheme R of FIG. 12 for compounds 144 and 145 (Table 2) and is described in detail in Example 22 below.

Preparation of Orientational Analogs of Bivalent Compounds

The orientation of a ligand with respect to the linker may be varied, as described previously, by coupling two ligands of the same type to a linker through different functional attachment points. The preparation of such compounds may be carried out by conventional variations of the methods described above for heterovalomers.

Alternatively, such compounds may be prepared by using a monoprotected linker to form a ligand-linker conjugate, which is then deprotected and coupled to a second ligand of the same type through a different functionality. A variation of this method is shown, for example, in Scheme T of FIG. 14 and exemplified in Example 24. Scheme T of FIG. 14 illustrates a preferred route for the synthesis of $C_\alpha$—N orientational analogs, using a ligand precursor to form a ligand precursor-linker conjugate. The synthesis of this ligand is completed after the second ligand is linked to the linker (i.e., in steps 4 and 5).

Preparation of Compounds of Formula I where p=3–10

Compounds of Formula I of higher order valency, i.e. p>2, can be prepared by simple extension of the above strategies, for example, by coupling ligands to a central core bearing multiple functional groups (see, e.g., Reaction Scheme S of FIG. 13) or to a tetrahedral atom such as carbon or nitrogen. The reaction conditions are the same as described above for the preparation of bivalent compounds, with appropriate adjustments made in the molar quantities of ligand and reagents.

Referring to Reaction Scheme S, three or more molar equivalents of an appropriately substituted N-aryl-2-haloacetamide is reacted with one equivalent of a triamine or triamine salt, preferably in an ethanolic solution containing diisopropylethylamine under an inert atmosphere with mild heating, e.g. 80° C., for several hours until the reaction is complete. For reaction of secondary amines, the solution is preferably heated at reflux.

The trivalent compound is isolated and purified by conventional means, preferably by precipitation and filtration. For preparation of compounds of higher-order valency, a similar procedure is followed, using an appropriate number of moles of halocompound.

When it is desired to incorporate degradable ester linkages into the multivalent compound, this may be accomplished by the use of a local anesthetic-type binding group having an ester rather than an amide linkage (see, e.g., Table 2, compounds 71, 73, 100 and others.) An alternative route is shown in Scheme I-1 of FIG. 8 (formation of compound (42)). Alternatively, one or more ester linkages may be incorporated into the linking framework, as illustrated below.

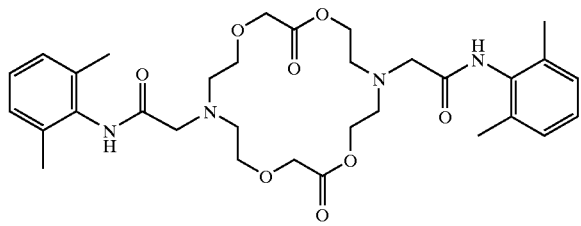

Isolation and Purification of the Compounds

Isolation and purification of the compounds and intermediates described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples herein below. However, other equivalent separation or isolation procedures could, of course, also be used.

Testing

Local anesthetics can be tested for activity in various well-known assays (e.g., the batrachotoxin (BTX) displacement assay (McNeal et al, *J Med. Chem.* 28: 381 (1985)), patch clamp method (see, generally, Neher and Sakmann, "The Patch Clamp Technique," *Scientific American* pp. 44–51 (1992); Hamill et al, *Pflügers Arch.* 391: 85 (1981); intact isolated nerve assay, e.g., isolated frog sciatic nerve (see Example 13 described below); blockage of the cutaneous trunci muscle reflex (CTMR) in guinea pigs (Bulbring et al, *J Pharmacol. Exp. Therap.* 85: 78–84 (1945); Blight et al, *J Compar. Neurology* 296: 614–633 (1990), Choi et al, *Life Sci.* 61: PL177–84 (1997)). Evaluation of motor and sympathetic function during sciatic nerve block in the rat is described, e.g., in Grant et al, *Anesth. Analg.* 75: 889–94 (1992), and Thalhammer et al., *Anesthesiology* 82: 1013–25 (1995).

The multi-binding compounds prepared as described above were screened for voltage-gated $Na^+$ ion channel binding and functional activities as exemplified in Examples 25–28 below.

Utility

The compounds of Formula I are useful in modulating the activity of voltage-gated $Na^+$ channels in mammals, e.g., humans. They will typically be used for the prevention and alleviation of pain, e.g., for topical anesthesia, infiltration anesthesia, field block anesthesia, nerve block anesthesia, spinal anesthesia, epidural anesthesia, post-operative analgesia, post-arthroscopic pain management, inflammatory pain, neuropathic pain, depression, seizure (epilepsy) and neuroprotection (stroke) and are useful for other indications, e.g., protection and recovery from ischemia (Lantos et al, *Arch. Int. Pharmacodyn. Ther.* 331: 179 (1996)), asthma (Hunt et al., *Mayo Clin. Proc.* 71: 361 (1996), rapid heartbeat (Gorgels et al *Am. J. Cardiol.* 78: 43 (1996)), cardiac arrhythmia (Rosen et al, *Am. Heart J.* 89: 526 (1975), natriuresis (Wyeth et al, *Life Sci.* 60: 473 (1997) proctitis and active distal ulcerative colitis (Arlander et al, *Aliment. Pharmacol. Ther.* 10: 73 (1996)), inflammatory bowel disease and irritable bowel syndrome.

Pharmaceutical Formulations

When employed as pharmaceuticals, the compounds of Formula I are usually administered in the form of pharmaceutical compositions. This invention therefore provides pharmaceutical compositions which contain, as the active ingredient, one or more of the compounds of Formula I above or a pharmaceutically acceptable salt thereof and one or more pharmaceutically acceptable excipients, carriers, diluents, permeation enhancers, solubilizers and adjuvants. One or more compounds of Formula I may be administered alone or in combination with other therapeutic agents (e.g., vasoconstrictors, anti-inflammatory agents, antibiotics, other monobinding anesthetic bases and salts, counter-irritants), carriers, adjuvants, permeation enhancers, and the like. The compounds may be formulated using conventional techniques such as those described in *Remington's Pharmaceutical Sciences,* Mace Publishing Co., Philadelphia, Pa. $17^{th}$ Ed. (1985) and "Modern Pharmaceutics," Marcel Dekker, Inc. $3^{rd}$ Ed. (G. S. Banker & C. T. Rhodes, Eds.). Pharmaceutically acceptable salts of the active agents (e.g., acid addition salts) may be prepared using standard procedures known to those skilled in the art of synthetic organic chemistry and described, e.g., by J. March, *Advanced Organic Chemistry: Reactions, Mechanisms and Structure,* $4^{th}$ Ed. (New York: Wiley-Interscience, 1992).

The compounds of Formula I may be administered by any of the accepted modes of administration of agents having similar utilities, for example, by oral, topical, or by parenteral routes (e.g., intradermal, intravenous, subcutaneous, intramuscular), intra-articular, intraspinal, epidural, rectal, vaginal, or transdermal/transmucosal routes. The most suitable route will depend on the nature and severity of the condition being treated. Subcutaneous, intradermal and percutaneous injections (intended to deliver the agent in close proximity to a peripheral nerve trunk) are preferred routes for the compounds of this invention. In making the compositions of this invention, the active ingredient is customarily diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Alternatively, the compounds of this invention may be solubilized and capsulated (e.g., in a liposome or a biodegradable polymer), or used in the form of microcrystals coated with an appropriate nontoxic lipid (see, e.g., P. J. Kuzma et al, *Regional Anesthesia* 22 (6): 543–551 (1997).

The compositions may be formulated to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across tissue barriers.

These compositions may be formulated as oral sprays. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

For topical use, the compositions can be in the form of emulsions, creams, jelly, solutions, ointments containing, for example, up to 5% by weight of the active compound. For parenteral administration, the compositions can be in the form of sterile injectable solutions and sterile packaged powders. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, *Regional Anesthesia* 22 (6): 543–551 (1997), all of which are incorporated herein by reference.

Another preferred formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252; 5,719,197; and 4,992,445, all of which are incorporated herein by reference. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., an ampoule).

The multibinding compounds of the present invention, or their pharmaceutically acceptable salts, are administered in a therapeutically effective amount. The duration of action and/or potency of such compounds will be increased by comparison with monobinding local anesthetics, thus dosage and dosing schedule must be adjusted accordingly. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

The following formulation examples illustrate representative pharmaceutical compositions of the present invention and should not be considered as limiting in any way the invention being disclosed. In particular, a vasoconstrictor, preferably epinephrine, may be added to the following formulations in order to provide a preparation that has a longer duration of action. Additionally, addition of lidocaine to the formulations provides a preparation with an enhanced onset time of anesthesia.

Formulation Example 1
Solution for Injection

| Ingredient | Quantity |
|---|---|
| Sodium Chloride | 0.9% (0.9 g/100 mL) |
| Methylparaben | 1 mg/mL |
| Compound of Formula I | 0.5% (0.5 g/100 mL) |
| Water for injection | to 100 mL |

Formulation Example 2
Paste

| Ingredient | Quantity (%) |
|---|---|
| Compound of Formula I | 1 |
| Zinc oxide | 25 |
| Starch | 25 |

-continued

Formulation Example 2
Paste

| Ingredient | Quantity (%) |
| --- | --- |
| Calamine | 5 |
| White petrolatum | to 100 |

Formulation Example 3
Ointment

| Ingredient | Quantity (%) |
| --- | --- |
| Compound of Formula I | 10 |
| White petrolatum | to 100 |
| White wax | 5 |

Formulation Example 4
Cream

| Ingredient | Quantity (%) |
| --- | --- |
| Compound of Formula I | 0.5 |
| Oleaginous phase | |
| Spermaceti | 12.5 |
| White wax | 12.0 |
| Almond Oil | 55.5 |
| Aqueous phase | |
| Sodium borate | 0.5 |
| Stronger rose water | 2.5 |
| Purified water | 16.5 |
| Aromatic | |
| Roseoil | 0.02 |

Formulation Example 5
Gel

| Ingredient | Quantity (%) |
| --- | --- |
| Compound of Formula I | 2 |
| Methocel 90 H.C. 4000 | 0.8 |
| Carbopol 934 | 0.24 |
| Propylene glycol | 16.7 |
| Methylparaben | 0.015 |
| Purified water | to 100 |

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

Numbered compounds referred to in the examples below (e.g. compound 85) correspond to compounds of Formula I shown in Table 2.

Additionally, the following abbreviations have the following meanings. If an abbreviation is not defined, it has its generally accepted meaning.

| | |
| --- | --- |
| BOC | teri-butyloxycarbonyl |
| BTX | batrachotoxin |
| Cbz | carbobenzyloxy |
| DCC | N,N-dicyclohexylcarbodiimide |
| DIPEA | diisopropylethylamine, Hunig's base |
| DMA | N,N-dimethylacetamide |
| DMF | N,N-dimethylformamide |
| DMSO | dimethylsulfoxide |
| DPPA | diphenylphosphoryl azide |
| HATU | 6-(7-azabenzotriazol-1-yl)-N,N,N'N'-tetramethyluronium hexafluorophosphate |
| HBTU | 1-hydroxybenzotriazole |
| HOAT | 1-hydroxy-7-azabenzotriazole |
| PyBOP | pyridine benzotriazol-1-yloxy-tris(dimethyl-amino)phosphonium hexafluorophosphate |
| TEA | triethylamine |
| TFA | trifluoroacetic acid |
| THF | tetrahydrofuran |

Example 1

Preparation of a Linker of Formula (2), where Z= $(CH_2)_4$ 1,4-Diaminobutane (34.0 mmol) was dissolved in 100 mL dichloromethane under a nitrogen atmosphere. Di-tert-butyl dicarbonate ($Boc_2O$) (119.12 mmol) dissolved in 100 mL dichloromethane was added dropwise to the stirred solution and stirring was continued at room temperature until the reaction was complete (4 hours). The course of the reaction was followed by TLC (50% ethyl acetate and 50% hexanes). The reaction mixture was evaporated giving a precipitate that was collected by filtration. The precipitate was rinsed with ether to yield a white solid (9.02 grams; 92% yield).

Lithium aluminum hydride (LAH) (63.3 mmol) was dissolved in 200 mL tetrahydrofuran (THF) in an ice bath under nitrogen atmosphere. Di-Boc-protected diamine (12.7 mmol) was dissolved in 50 mL THF and added dropwise to the LAH/THF solution. The reaction was stirred with cooling, then warmed to room temperature, placed in an oil bath and the temperature was raised by increments of 10° C. to 85° C. over a 30 minute period. The mixture was stirred at reflux for 18 hours, then cooled to room temperature and placed in an ice bath. Sodium sulfate decahydrate was slowly added to quench the excess LAH. The solids were removed by filtration and rinsing with THF. The filtrate was concentrated to a thick syrup and excess solvent removed under vacuum to yield N,N-dimethyldiaminobutane as a viscous oil (3.58 grams; 98% yield). The product was characterized by NMR (DMSO) and MS (calculated, M+H= 117.2; found, 117.3).

Example 2

2A. Preparation of a compound of formula (5), where Ar=2,6-dimethylphenyl, $R^1$=Et, $R^2$=H 2,6-Dimethylaniline (82.5 mmols) was dissolved in 100 mL dichloromethane under a nitrogen atmosphere, and cooled in an ice bath. DIPEA (247.6 mmols) was added to the solution, and 2-bromobutyric acid (165.0 mmols) in 100 mL $CH_2Cl_2$ was added over one hour by dropping funnel. After the addition was complete, the solution was brought to room temperature and stirred for an additional hour. The reaction mixture was concentrated, and ether added to the residue. The ether was decanted, and the undissolved salts were rinsed with ether (×2). The combined ether solution was washed with 3 N NaOH (×2), 3 M HCl (×2), saturated $NaHCO_3$, saturated NaCl, and dried over $MgSO_4$. The crude product, 2-bromo-N-(2,6-dimethylphenyl)-butyramide, was concentrated and dried, and used without further purification in subsequent coupling steps. The product was characterized by NMR (DMSO).

Other compounds of formula (5) were prepared in a similar manner.

2B. The preparation of a compound of formula (5), where Ar=4-[—C(O)—OCH$_3$]-2,6-dimethylphenyl was carried out as described in Example 2A with the modification that 2,6-dimethylaniline was replaced with 1-amino-4-[—C(O)—OCH$_3$]-2,6-dimethylbenzene. This ester was prepared by refluxing 1 equivalent (10 g) of 1-amino-2,6-dimethylbenzoic acid with 1.2 equivalents of sulfuric acid in 200 mL MeOH overnight. Alternatively, 1 equivalent of 1-nitro-2,6-dimethylbenzoic acid was refluxed overnight with 0.2 equivalents of sulfuric acid in 200 mL MeOH. The reaction was then concentrated, dissolved in ether, washed with saturated NaCl, dried over MgSO$_4$, filtered, and concentrated under vacuum to yield 4-[C(O)—OCH$_3$]-2,6-dimethylbenzene. Characterized by NMR.

Similarly, other benzoic acid esters of compounds of formula (5) were prepared.

Example 3

Preparation of a Compound of Formula (12), where Ar=4-nitrophenyl, m=2

Under a nitrogen atmosphere, bromoethanol (29 mmols) was dissolved in 25 mL ether. Pyridine (34 mmols) was added to the solution, followed by a solution of 4-nitrobenzoyl chloride (27 mmols) in 35 mL ether. The reaction was stirred overnight, and a white precipitate was formed. Ether (50 mL) was added, and the reaction mixture was then washed with aqueous KHSO$_4$, aqueous NaHCO$_3$, and water. The ether layer was then dried over Na$_2$SO$_4$, filtered, and concentrated to give 6.3 g of 4-nitrobenzoic acid 2-bromo-ethyl ester. Material was used in coupling reactions without further purification.

Example 4

Preparation of a Compound of Formula (16), where Ar=2,6-dimethyl-4-octyloxy-phenyl, and R$^1$=R$^2$=H 1. Compound of Formula (13)

Under a nitrogen atmosphere, 3,5-dimethylphenol (40.9 mmoles) was dissolved in 40 mL water and 40 mL ether. To this was added 1.5 equivalents (61.4 mmoles) of sodium nitrate (NaNO$_3$). The reaction was cooled in an ice bath and 50 mL concentrated HCl was slowly added to the reaction. The reaction was warmed to room temperature and followed by TLC (ethyl acetate:hexanes, 1:1) until the reaction was complete (0.5 hour). The reaction was extracted into ether (×3), washed with saturated NaHCO$_3$, saturated NaCl, dried over MgSO$_4$, filtered, rinsed with ether, and concentrated. The product was purified using silica-gel chromatography, yielding 3,5-dimethyl-4-nitro-phenol as a yellow solid (2.05 grams; 30% yield). The product was characterized by NMR (DMSO).

2. Compound of Formula (14)

Under a nitrogen atmosphere, 3,5-dimethyl-4-nitro-phenol (8.38 mmoles) was dissolved in 20 mL dimethylformamide (DMF). To this was added potassium carbonate (41.92 mmols) and 1-bromooctane (8.38 mmols). The reaction was stirred for 12 hours. The reaction mixture was partitioned between [ethyl acetate:hexanes, 1:1] and water, and the organic layer was washed with water (×3), brine, dried over MgSO$_4$, and concentrated. The yield of 2,6-dimethyl-4-(octyloxy)-nitrobenzene product as a yellow oil was 2.2 grams (94%). The product was characterized by NMR (DMSO).

3. Compound of Formula (15)

Under a nitrogen atmosphere in a Parr bottle, 2,6-dimethyl-4-(octyloxy)-nitrobenzene (7.89 mmoles) was dissolved in methanol (100 mL). To this was added 0.5 grams of 10% Pd/C, and shaken under a hydrogen atmosphere (30 PSI) for 18 hours. The catalyst was filtered off over Millipore filter paper, and rinsed with methanol. The filtrate was concentrated to yield 2,6-dimethyl-4-(octyloxy)-aniline as a thick oil (1.8 grams; 91%). The product was characterized by NMR (DMSO).

4. Compound of Formula (16)

Under a nitrogen atmosphere, 2,6-dimethyl-4-(octyloxy)-aniline (7.2 mmols) was dissolved in 50 mL dichloromethane. To this was added DIPEA (9.4 mmols). The reaction mixture was cooled in an ice bath, and chloroacetyl chloride (7.95 mmoles) dissolved in 50 mL dichloromethane was added by dropping funnel. After the addition was complete, the reaction was stirred at room until reaction was complete by TLC (approximately 0.5 hours). The reaction mixture was concentrated, and partitioned between ethyl acetate and water. The organic layer was washed with saturated NaHCO$_3$ (×2), brine, dried over MgSO$_4$, and filtered (rinsing with ethyl acetate). The filtrate was concentrated to yield 2-chloro-N-(2,6-dimethyl-4-octyloxyphenyl)-acetamide as a white solid (1.21 grams; 51%). The product was characterized by NMR (DMSO).

Examples 5–12

(Compounds of Formula I, where X is a Compound of Formula II)

Example 5

5A. Preparation of a compound of Formula Ia according to Scheme E, where (Ar—W)$^1$=(Ar—W)$^2$=2,6-dimethylphenyl-NH—C(O)—CH$_2$—, R$^3$=R$^4$=Me, Z=(CH$_2$)$_4$ (i.e., compound 9, Table 2)

1. Preparation of 2-chloro-N-(2',6'-dimethylphenyl) acetamide (i.e., N-aryl-2-chloroacetamide)

Under nitrogen atmosphere, one equivalent of an appropriately substituted aniline (7.2 mmoles) was dissolved in 50 mL dichloromethane. To this was added 1.3 equivalents of DIPEA (9.4 mmoles). The reaction mixture was cooled in an ice bath. Chloroacetyl chloride (7.95 mmoles) dissolved in 50 mL dichloromethane was added dropwise to the reaction mixture. The reaction was stirred at room temperature until reaction was complete (approximately 0.5 hours). The course of the reaction was followed by TLC (50% ethyl acetate and 50% hexanes). The reaction mixture was evaporated to a syrup, and was then partitioned between EtOAc and water. The organic layer was washed with saturated NaHCO$_3$ (2 times), saturated NaCl, then dried with MgSO$_4$, filtered and rinsed with EtOAc. After removal of excess solvent, 2-chloro-N-(2',6'-dimethylphenyl)acetamide was obtained as a white solid (51% yield).

2. Preparation of a Compound of Formula Ia (i.e., Compound 9, Table 2)

Under nitrogen atmosphere, N,N-dimethyl-1,4-diaminobutane (1.95 mmoles), 1.9 equivalents of 2-chloro-N-(2',6'-dimethylphenyl)acetamide (3.71 mmoles) and 2.5 equivalents of diisopropylethylamine (DIPEA) (4.89 mmoles) were dissolved in 4 mL ethanol. This was refluxed at 85 degrees C and followed by TLC (ethyl acetate:hexanes, 1:1) until the reaction was complete (12 hours). The reaction was cooled to room temperature, inducing crystallization of the product. The product was filtered, rinsed with ether, and dried on a vacuum line to yield the compound of Formula Ia (i.e., compound 9, Table 2) as a white solid (0.88 grams (83% yield). The product was characterized by NMR (DMSO). Mass spectrometry was taken in methanol.

5B. In a similar manner, by using different linkers of Formula II and/or compounds of formula (5), the following compounds of Formula Ia were prepared (Table 2): 1, 3, 4, 5, 6, 12, 13, 14, 17, 18, 19, 42, 43, 44, 45, 46, 47, 48, 49, 50, 51, 52, 53, 54, 117, 119.

5C. Compounds of Formula I of higher-order valency were prepared as described in Example 5A using the appropriate molar quantities of multifunctional amine linkers of Formula II and N-aryl-2-chloroacetamide.

Example 6

Preparation of an Intermediate Compound of Formula (23), Scheme F, where Ar=2,6-dimethylphenyl, $R^1=R^2=H$, $R^3=Et$ Under a nitrogen atmosphere, methylamine (600 mmols) in 300 mL THF was cooled to 0° C. A solution of 2-chloro-N-(2',6'-dimethylphenyl)acetamide (100 mmols) was dissolved in 200 mL THF, and slowly dripped into the cold methylamine solution. The reaction was stirred overnight. The reaction was filtered, and the filtrate evaporated to yield an oily residue. This was dissolved in EtOAc (100 mL) and treated with 1N HCl (200 mL). The aqueous layer was washed with EtOAc, then basified to Ph 10–12 with 6 N NaOH. The product was extracted into EtOAc (2×50 mL), the organic phase was dried, and the solvent was evaporated to yield N-(2,6-dimethyl-phenyl)-2-methylamino-acetamide (compound (23)) as an oil (12.8 gm; 67% yield).

Example 7

7A. Preparation of a compound of Formula Ia according to Scheme G, where $(Ar-W)^1=(Ar-W)^2=2,6$-dimethylphenyl-NH—C(O)—CH(CH$_2$CH$_3$)—, $R^3=R^4=H$, $Z=(CH_2)_4$ (i.e., compound 16, Table 2)

Under a nitrogen atmosphere, 1,4-diaminobutane (11.34 mmols), 2-bromo-N-(2,6-dimethyl-phenyl)-butyramide (22.69 mmols), and DIPEA (28.36 mmols) were dissolved in EtOH (5 mL). The reaction was heated at reflux for 24 hours, then concentrated and chromatographed on a silica gel column to yield a compound of formula (26) (compound 16, Table 2).

7B. In a similar manner, by varying the linker chain length, compounds 15 and 20 (Table 2) were prepared.

7C. Compounds of formula (26), where $R^1=R^2=H$, and Z is a $C_2-C_{10}$ alkylene chain were prepared by substituting in the above reaction 2-bromo-N-(2,6-dimethyl-phenyl)-acetamide for 2-bromo-N-(2,6-dimethyl-phenyl)-butyramide, and using linkers of formula (1), where Z is $C_2-C_{10}$ alkylene.

7D. Compounds of Formula I of higher-order valency were prepared as described in 7A, by increasing the molar equivalents of the ligand.

Example 8

8A. Preparation of a compound of Formula Ia according to Scheme G, where $(Ar-W)^1=(Ar-W)^2=2,6$-dimethylphenyl-NH—C(O)—CH(CH$_2$CH$_3$)—, $R^3=R^4=$n-propyl, $Z=(CH_2)_4$ (i.e., compound 33, Table 2).

Under a nitrogen atmosphere, 1.25 mmols of the compound of formula (26), prepared as described in the previous example, and bromopropane (2.5 mmols) were dissolved in 1mL EtOH in a sealed tube. DIPEA (2.75 mmols) was added, and the reaction refluxed for 12 hours. The reaction was concentrated, and the crude product purified by silica-gel chromatography (MeOH/CH$_2$Cl$_2$). After concentration of the product-containing fractions, the product was dissolved in MeOH (2 mL) and 4 N HCl was added until the pH was between 1 and 2. The solution was stirred for 20 minutes, and then pipetted into ether (300 mL) to precipitate the product as its dihydrochloride salt. This was filtered and dried, yielding the product (i.e., compound 33, Table 2) in 81% yield.

8B. In a similar manner, by varying $R^3$ in compound (27), the following compounds were prepared (Table 2): 22, 23, 26, 32, 33, 34, 35, 36, 37

Example 9

Preparation of Compounds of Formula Ia According to Scheme G, where $(Ar-W)^1=(Ar-W)^2=2,6$ dimethylphenyl-NH—C(O)—CH$_2$—, $R^3=R^4=$alkyl, Substituted Alkyl, Alkoxy, Benzyl, and Z is $C_2-C_{10}$ Alkylene Starting with compounds of formula (26) prepared as in Example 7C above, and varying $R^3$ in compound (27) the following compounds were prepared (Table 2): 2, 7, 8, 10, 12, 21, 24, 25, 27, 28, 29, 30, 31

Example 10

10A. Preparation of a compound of Formula Ia, according to Scheme H, where $(Ar-W)^1=(Ar-W)^2=2,6$-dimethylphenyl-NHC(O)—CR$^1$R$^2$, where $R^1$ is H and $R^2$ forms a piperidinyl group together with $R^3$ and $R^4$ of the linker, and $Z=(CH_2)_{10}$ (i.e., compound 11, Table 2)

Step 1: Under a nitrogen atmosphere, 77.4 mmoles of DL-pipecolinic acid (i.e., piperidine-2-carboxylic acid) was dissolved in 80 mL 3 N aqueous NaOH, and cooled in an ice bath. Benzyl chloroformate (92.3 mmoles) and 25 mL 3 N NaOH were added in alternating aliquots over 1 hour, and the reaction mixture was then stirred at room temperature for 12 hours. When the reaction was complete, the N-protected carboxylic acid (abbreviated herein as Cbz-DL-pipecolinic acid) was extracted with ether (×3). The basic layer was acidified with 6 N HCl and extracted with ether (×3). The combined ether layers were rinsed with 1 N HCl, saturated NaCl, then dried over MgSO$_4$, filtered (rinsing with ether) and concentrated. The yield of the desired product as a white solid was 19.65 grams (96% yield). The product was characterized by NMR (DMSO).

Step 2: Under nitrogen atmosphere, Cbz-DL-pipecolinic acid (9.1 mmols) was dissolved in DMF (10 mL). DIPEA (12.4 mmols), HATU (10.7 mmols) and HOAT (0.82 mmols) were added, and the reaction was stirred at room temperature for 1 hour. 2,6-dimethylaniline (8.25 mmoles) was added, and the reaction was stirred for 18 hours. The reaction mixture was then partitioned between water and EtOAc. The organic layer was washed with 1 N NaOH, 2 N HCl, saturated NaCl, then dried over MgSO$_4$, filtered (washing with EtOAc), and concentrated. The desired amide product [Cbz-piperidine-2-carboxylic acid (2,6-dimethyl-phenyl)-amide] was afforded as a white solid (3.0 grams, 99% yield). The product was characterized by NMR (DMSO).

Step 3: Under nitrogen atmosphere in a Parr bottle, 8.2 mmoles of [Cbz-piperidine-2-carboxylic acid (2,6-dimethyl-phenyl)-amide] was dissolved in MeOH (100 mL). 10% Pd/C (0.5 g) was added, and the bottle was agitated under a hydrogen atmosphere (20 psi) for 30 minutes. The catalyst was filtered off using Millipore filter paper (washing with MeOH). The filtrate was concentrated to a thick syrup, yielding 1.75 grains (92% yield) of [piperidine-2-carboxylic acid (2,6-dimethyl-phenyl)-amide] as an off-white solid. The product was characterized by NMR (DMSO).

Step 4: Under a nitrogen atmosphere, 1,10-dibromodecane (0.22 mmoles), [piperidine-2-carboxylic acid (2,6-dimethyl-phenyl)-amide] (0.43 mmoles), and DIPEA (0.57 mmoles) were dissolved in 2 mL ethanol, and stirred at 80° C. for 12 hours. The reaction mixture was separated by reverse- phase preparative HPLC, eluting with a gradient of 15–90% acetonitrile in water over 90 minutes. The desired peak was pooled, frozen, lyophilized, and collected as a white powder (the TFA salt). The product was dissolved in 0.1 N HCl and lyophilized to exchange to the HCl salt. The compound of Formula Ia (compound 11, Table 2) was obtained as a white solid (0.083 grams; 61% yield). The product was characterized by NMR (DMSO).

10B. In a similar manner, substituting 1,3-dibromopropane and 1,6-dibromohexane for 1,10-dibromodecane in Example 10A, compounds 38 and 40 (Table 2) were prepared.

10C. The procedure of Example 10A was used with the following modification for preparing compounds 39 and 41 (Table 2). 1,3-dibromopropane was replaced with Br—$CH_2$—CH=CH—$CH_2$—Br (yielding compound 41, Table 2). Compound 39 was prepared by catalytic hydrogenation of compound 41.

Example 11

Preparation of a Compound of Formula Ia, According to Scheme I, where
(Ar—W)$^1$=(Ar—W)$^2$=4-butylamino-phenyl-C(O)—, $R^3$=$R^4$=H, Z=$(CH_2)_3$—O—$(CH_2)_2$—O—$(CH_2)_2$—
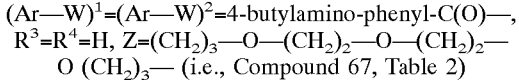
O $(CH_2)_3$— (i.e., Compound 67, Table 2)

Under a nitrogen atmosphere, 4,7,10-trioxa-1,13-tridecanediamine (2.27 mmols), HATU (6.81 mmols), HOAt (0.22 mmols), and DIPEA (7.94 mmols) were added to 20 mL DMF and stirred for 20 minutes at room temperature. 4-(butylamino) benzoic acid (5.67 mmols) was added and the reaction was stirred overnight. The product (compound 67, Table 2) was purified by reverse-phase preparative HPLC and characterized by NMR (DMSO).

Example 12

12A. Preparation of a compound of Formula Ia, according to Scheme J, where (Ar—W)$^1$=(Ar—W)$^2$=4-(C(O)—NH—$(CH_2)_2$—$N(CH_2CH_3)_2$)-phenyl-, $R^3$=$R^4$=H, Z=$(CH_2)_6$ (i.e., compound 60, Table 2)

Step 1: Under a nitrogen atmosphere, 4-aminobenzoic acid (52.7 mmols), benzyl bromide (67.3 mmols), benzyl-triethylammonium chloride (80 mmols) and $K_2CO_3$ (144.7 mmols) were dissolved in acetonitrile. The reaction mixture was heated at 90° C. for 6 hours, cooled to room temperature, and filtered. The filtrate was concentrated, dissolved in $CH_2Cl_2$: MeOH, 9:1 v/v (100 mL), and stirred with 30 g MB amberlite for one-half hour. The residue was filtered off, and the filtrate concentrated. The crude product was purified by silica-gel chromatography (ethyl acetate/hexanes) to give 5.66 g (47% yield) of the desired product, 4-amino-benzoic acid benzyl ester. The product was characterized by NMR ($CDCl_3$) and MS (found, M+H=228).

Step 2: Under a nitrogen atmosphere, 4-amino-benzoic acid benzyl ester (25 mmols) was dissolved in ether (400 mL). The mixture was cooled to 0° C. and trifluoroacetic anhydride (92 mmols) was added. The reaction mixture was stirred at 0° C. for 3 hours, concentrated to dryness, the residue was dissolved in ether, washed with 10% $NaHCO_3$ solution, then brine. The organic phase was dried over $MgSO_4$, filtered, and concentrated to dryness to give 4-(2,2,2-trifluoro-acetylamino)-benzoic acid benzyl ester (8.2 g, 100% yield ) as a white solid. The product was characterized by NMR ($CDCl_3$) and MS (found, M+H=323).

Step 3: Under a nitrogen atmosphere, 4-(2,2,2-trifluoro-acetylamino)-benzoic acid benzyl ester (9.6 mmols), 1,6-diiodohexane (5 mmols), benzyltriethyl ammonium chloride (1.1 mmols) and $K_2CO_3$ (21.7 mmols) were dissolved in $CH_3CN$ (150 mL). The reaction mixture was stirred under reflux for 48 hours, cooled, and filtered. The filtrate was concentrated to dryness, and purified by silica-gel chromatography (ethyl acetate/hexanes) to yield 1.3 g (37% yield) of the desired product (a compound of formula (48), where Ar=phenyl and Z=$(CH_2)_6$). The product was characterized by NMR ($CDCl_3$) and MS (found, MH$^+$=725). MS (found, MNa$^+$=747).

Step 4: A solution of the above-referenced compound of formula (48) (1.6 mmols) in THF (200 mL) was stirred under $H_2$ atmosphere in the presence of 10% Pd/C (450 mg) for 12 hrs. When the reaction was complete, the catalyst was filtered off, and the filtrate was concentrated to give 1.01 g of the crude deprotected product (i.e., a compound of formula (49), where Ar=phenyl and Z ($CH_2)_6$)) as a white solid.

Step 5: Under a nitrogen atmosphere, the above-referenced compound of formula (49) (1.45 mmols), was dissolved in THF (80 mL). HATU (3 mmols), HOAT (36 mmols), diethylaminopropylamine (50) (3.55 mmols), and DIPEA (3.04 mmols) were added. The reaction mixture was stirred at room temperature for 3 days, then concentrated to dryness. The crude product was purified by silica-gel chromatography (methylene chloride/methanol/ammonia) to give 450 mg (100% yield) of the desired product (i.e., a compound of formula (51), where $R^{10}$=diethylaminopropyl, Ar=phenyl, and Z=$(CH_2)_6$). The product was characterized by NMR ($CD_3OD$) and MS (found, M+H=745). MS (found, MNa$^-$=767).

Step 6: Under a nitrogen atmosphere, the above-referenced compound of formula (51) (450 mg) was dissolved in a solution of 2N $NH_3$ in MeOH (40 mL). After addition of 25% aqueous $NH_3$ ammonia solution (8 mL), the mixture was heated to 62° C. overnight. When the reaction was complete as judged by TLC, the reaction mixture was cooled to room temperature, and a white precipitate was formed. The precipitate was collected, washed with $H_2O$, and dried under vacuum to give 230 mg of the compound of Formula Ia (i.e., compound 60, Table 2 ), which was exchanged to the HCl salt.

The product was characterized by NMR ($CD_3OD$) and MS (found, M+H=553). MS (found, MNa$^+$=575).

12B. In a similar manner, by varying the alkylene chain length of the linker from $C_4$–$C_{12}$, the following compounds were prepared (Table 2): 59, 60, 61, 62, 63, 64, 65, 66.

12C. Compound 125 (Table 2) was prepared as in Example 12B with the following modification. In the final step of the procedure, deprotection was carried out with 2N $MeNH_2$/THF rather than with 25% aqueous ammonia.

Examples 13–19

(Compounds of Formula I, where X is a Compound of Formula III)

Example 13

13A. Preparation of a Compound of Formula Ib, according to Scheme K, where (Ar—W)$^1$=(Ar—W)$^2$=2,6- dimethylphenyl-NH—C(O)—CH($CH_2CH_3$)—, $Y^aY^b$=covalent bond, Z=1,4,10,13-tetraoxa-7,16-diaza-cyclooctadecane (i.e., compound 85,Table 2)

Under nitrogen atmosphere, 1,4,10,13-tetraoxa-7,16-diaza-cyclooctadecane (53.36 mmols), 2-bromo-N-(2,6-dimethyl-phenyl)-butyramide (133.41 mmols), and DIPEA (117.40 mmols) were dissolved in 20 mL ethanol. The reaction was refluxed for 6 days, then cooled and the solvent removed in vacuo. The reaction mixture was partitioned between 1N HCl (300 mL) and ethyl acetate. The acidic layer was extracted with ethyl acetate (×4), then basified with 6 N NaOH (100 mL) and extracted with ethyl acetate (×3). The combined organic extracts were washed with 10% $Na_2S_2O_3$ (×2), brine, and dried over $MgSO_4$, decolorized with charcoal, filtered,and concentrated. The crude product (26 g) was purified using silica-gel chromatography (MeOH/$CH_2Cl_2$) and exchanged to the HCl salt to give a compound of Formula Ib (i.e., compound 85, Table 2) (33% yield). Characterized by NMR (DMSO).

13B. In a similar manner, by using different Z groups in linkers of Formula III and/or different compounds of formula (5), the following compounds were prepared (Table 2): 75, 76, 77, 78, 79, 80, 81, 82, 83, 84, 86, 87, 88, 89, 94, 95, 104, 105, 106, 107, 151.

13C. Trivalent compounds of Formula Ib were prepared as described in Example 13B using increased molar quantities of compounds of formula (5).

13D. Substituting other compounds of formula (16) (prepared as described in Scheme D of FIG. 6) for compounds of formula (5) in Example 13B, and other compounds of formula (3), the following compounds were prepared (Table 2): 155,156,157,158,161,163,164.

It should be understood that the compounds of this invention include the R,R-, R,S-(meso), and S,S-isomers. Of course, it is also understood that the activity of a mixture of isomers may vary depending on the activities and proportions of each isomer in the mixture. It is well within the skill in the art to test different isomers and combinations thereof to determine which is more active for any particular intended use.

Example 14

Preparation of a Compound of Formula Ib, According to Scheme K, where (Ar—W)$^1$=(Ar—W)$^2$=2,6-dimethylphenyl-O—C(O)—$CH_2$—, $Y^a$=$Y^b$=covalent Bond, Z=1,4,10,13-tetraoxa-7,16-diaza-cyclooctadecane (Compound 102, Table 2)

The procedure of Example 13A above was modified as follows to prepare compound 102 (Table 2). 2-Bromo-N-(2,6-dimethyl-phenyl)butyramide was replaced with bromoacetic acid 2,6-dimethyl-phenyl ester.

Example 15

15A. Preparation of a compound of Formula Ib, according to Scheme K, where (Ar—W)$^1$=(Ar—W)$^2$=4-aminophenyl-C(O)—O—($CH_2$)$_2$—, $Y^aY^b$=covalent Bond, and Z=1,4,10,13-tetraoxa-7,16-diaza-cyclooctadecane (i.e., Compound 100, Table 2)

The crude product of Example 4, 4-nitro-benzoic acid 2-bromo-ethyl ester (19 mmols) and 1,4,10,13-tetraoxa-7,16-diaza-cyclooctadecane (7.6 mmols) were dissolved in 30 mL THF and stirred under nitrogen at reflux for 60 hours. The reaction mixture was concentrated, and the residue was partitioned between $CH_2Cl_2$ and water. The organic phase was washed with aqueous $KESO_4$ solution, aqueous $NaHCO_3$ solution, $H_2O$, then dried over $Na_2SO_4$, filtered, and concentrated to give 2.6 g of a crude orange oil. The product was purified by silica-gel chromatography (acetone/hexanes) to give 1.2 g (24% yield) of the desired product (compound 101, Table 2).

Under a nitrogen atmosphere, compound 101 (300 mg) and 50 mg of 10% Pd/C were dissolved in 5 mL THF. The reaction was stirred under a H2 atmosphere overnight. The suspension was then filtered through Celite under $N_2$, and the solvent evaporated to leave 258 mg of an oil, which crystallized into a colorless solid (95% yield). MS (M+H= 589). The product (compound 100, Table 2) was exchanged to the HCl salt and characterized by NMR (DMSO). 15B. In a similar manner, by substituting 2-chloro-4-nitro-benzoic acid 2-bromo-ethyl ester for 4-nitro-benzoic acid 2-bromo-ethyl ester in Example 15A, compound 103 (Table 2) was prepared.

Example 16

Preparation of a Compound of Formula Ib, According to Scheme L, where (Ar—W)$^1$=(Ar—W)$^2$=2,6-dimethylphenyl-NHC(O)—$CH_2$—, $Y^aY^b$=—C(O)—$CH_2$—N($CH_3$)—, Z=1,4,10,13-tetraoxa-7,16-diaza-cyclooctadecane (i.e., Compound 90, Table 2)

Step 1: Under nitrogen atmosphere, 1,4,10,13-tetraoxa-7,16-diaza-cyclooctadecane (2.0 mmol) was dissolved in 5 mL of dichloromethane. The solution was cooled to 0° C. and DIPEA (4.4 mmol) was added followed by addition of chloroacetyl chloride (4.4 mmol). The reaction was allowed to warm up to room temperature with stirring overnight. The solvent was evaporated under reduced pressure and the residue taken up in EtOAc. The organic solution was washed successively with 0.1N HCl, saturated $NaHCO_3$ soln. and brine, followed by drying over $Na_2SO_4$, filtration and evaporation to yield 850 mg of a light yellow oil, taken on as is to the next step. Characterized by MS in dichloromethane.

Step 2: Under a nitrogen atmosphere, the bis-chloroacetyl derivative of 1,4,10,13-tetraoxa-7,16-diaza-cyclooctadecane (1.0 mmols), N-(2,6-dimethyl-phenyl)-2-methylamino-acetamide (2.5 mmols) (prepared according to Example 5 above), and DIPEA (2.5 mmols) were dissolved in EtOH. The reaction was refluxed for 60 hours, then concentrated. The residue was dissolved in EtOAc, and washed with $NaHCO_3$ solution. The organic phase was dried, filtered, and evaporated to give 670 mg of crude product. The product (compound 90, Table 2) was purified by silica-gel chromatography (MeOH/$CH_2Cl_2$) to give 120 mg (16.5%) of the free base and characterized by NMR (DMSO) and by MS (M+H=728).

Example 17

17A. Preparation of a stereoisomeric form of a compound of Formula Ib, according to Scheme M, where (Ar—W)$^1$=(Ar—W)$^2$=2,6 dimethylphenyl-NH—C(O)CH($CH_2CH_3$)—(S) isomer, $Y^a$=$Y^b$=covalent bond, Z=1,4,10,13-tetraoxa-7,16-diaza-cyclooctadecane (i.e., compound 149, Table 2)

Step 1: Under a nitrogen atmosphere, 16.72 mmol Cbz-(L)-2-aminobutyric acid was dissolved in 45 mL DMF, and 19.7 mmol HATU, 1.52 mmol HOAt, 22.8 mmol DIPEA were added. The reaction was stirred for one hour, then 15.2 mmol of 2,6-dimethylaniline was added. The reaction mixture was stirred at room temperature for 48 hours. The product was precipitated from brine/ice/ether, and dried to afford 7.56 g of the crude product as a white solid. The product, (L)-2-Cbz-amino-N-(2,6-dimethyl-phenyl)-butyramide, was characterized by NMR (DMSO) and MS (calculated, 340; found, M+H 341).

Step 2: Under a nitrogen atmosphere in a Parr bottle, 7.561 g of (L)-2-Cbz-amino-N-(2,6-dimethyl-phenyl)-butyramide was dissolved in ethanol (30 mL) with 1 g 10% Pd/C. The reaction was monitored using mass spectroscopy. After eight hours, the catalyst was filtered off on Celite, and the filtrate was concentrated to afford 3.068 g (98% yield for last 2 steps) as a white solid. The deprotected product was characterized by NMR (DMSO) and MS (calculated, 206; found, M+H 207).

Step 3: Under a nitrogen atmosphere, a solution of 7.38 mmols I—$CH_2(CH_2OCH_2)_2CH_2$—I and 36.9 mmols $Na_2CO_3$ in 10 mL EtOH was prepared. 7.38 mmols of 2-Amino-N-(2,6-dimethyl-phenyl)-acetamide was added, and the reaction mixture was heated at 75° C. for 4 days. The reaction was cooled, filtered, and the filtrate was concentrated. The crude product was purified by silica-gel chromatography (MeOH/$CH_2Cl_2$) to yield 360 mg (9.2% yield) of compound 149 (Table 2) (i.e., the S,S-enantiomer of compound 85). The product was characterized by NMR (DMSO) and MS. MS (calculated, 640; found, M+H 642).

17B. In a similar manner, compound 131 in Table 2 (i.e., the R,R-enantiomer of compound 85) was prepared.

The following alternative procedure may be substituted for Step 3 above to obtain higher yields of either the S,S- or R,R-enantiomer of compound 85 in a shorter period of time. To the solution of the amide of (L)-2-aminobutyric acid (4.43 g, 21.5 mmol) in ethanol (21 mL), DIPEA (3.74 mL, 21.5 mmol) and 1,2-bis-(2-iodoethoxy)ethane (1.96 mL, 10.8 mmol) were added. The reaction mixture was heated at reflux for 24 h, allowed to cool and concentrated to afford a yellow oil. The crude product was purified by chromatography on silica (10:90 methanol:dichloromethane) to obtain the linear dimer, as a white solid (1.42 g, 25% yield).

To the solution of the linear dimer (1.20 g, 2.3 mmol) in DMF (2 mL), sodium carbonate (1.58 g, 15.0 mmol) and 1,2-bis-(2-iodoethoxy)ethane (0.492 mL, 2.7 mmol) were added. The reaction mixture was heated at 110° C. for 24 h, then allowed to cool. The solution containing the desired product was suspended in 1N HCl and pH was lowered to 2. The aqueous layer was washed with ethyl acetate, basified with 6N NaOH, and the product was extracted into ethyl acetate. The organic layer was dried over $MgSO_4$ and concentrated to afford the crude product as a yellow oil which was purified by chromatography on silica (10:90 methanol:dichloromethane) to afford compound 149 as a white solid (360 mg, 24% yield).

17C. The meso form of compound 85 (i.e., compound 150 in Table 2) was prepared by double recrystallization of the bisHCl salt of compound 85 from water (>90% pure). Alternatively, this compound can be prepared by silica gel chromatography of the racemic mixture of compound 85.

Example 18

Chiral Separation of the R,R and S,S pairs of compound 85 (Table 2)

One set of enantiomers of compound 85 were separated via a chiral column as follows:

Chiral columns (CHIRALPAK AD, Daicel Chemical Industries, Ltd.) were obtained from Chiral Technologies Inc.[Exton Pa.]. Semi-Preparative Column: Size=2 cm I.D.× 25 cm; Flow Rate=9.0 mL/min; Cat. No. 19045. Analytical Column: Size=0.46 cm I.D.×25 cm; Flow Rate=1.0 mL/min; Cat. No. 19025.

Both columns were run using hexane/ethanol/methanol= 90/8/2 as mobile phase (temperature=20° C.). All solvents were HPLC grade. Hexane and methanol (Burdick and Jackson Brand) were obtained from VWR. Ethanol (OmniSolv Alcohol, Reagent) was from EM Science.

The sample was dissolved in mobile phase and applied to the Semi-Preparative Column by manual injection. The HPLC eluent was monitored at 220 nm, and the desired peaks collected and dried.

The enantiomers were sufficiently resolved to give 98–99% purity for each, as determined using the Analytical Column.

Similarly, chiral separation of enantiomers of other compounds of Formula I can be separated by empirically choosing chiral columns and using solvent systems of appropriate polarity for the compounds to be separated.

As well, chiral separations can be effected by selective crystallization with an enantiomerically pure salt.

Example 19

19A. Preparation of a Compound of Formula Ib, according to Scheme I-2, where $(Ar—W)^1=(Ar—W)^2=$4-aminophenyl-C(O)—O—$(CH_2)_2$—, $Y^aY^b$=a covalent bond, and Z=—N($CH_3$)— (i.e., compound 108, Table 2).

The first step in the synthesis was a modification of the procedure described above in Example 11. In that procedure, N-methyldiethanolamine is substituted for 4,7,10-trioxa-1,13-tridecanediamine and 4-nitrobenzoyl bromide is substituted for 4-(butylamino)benzoic acid.

The second step in the synthesis was the reduction of the nitro group by catalytic hydrogenation, as previously described in Example 15, to yield compound 108 (Table 2).

19B. Similarly, a trivalent compound of Formula I was prepared by substituting triethanolamine for N-methyldiethanolamine in Example 19B.

Example 20

20A. Preparation of a compound of Formula Ic, according to Scheme N, where $(Ar—W)^1=(Ar—W)^2=$2,6-dimethylphenyl-NH—C(O)—$CH_2$—, $R^3=R^4$=methyl, $R^7=R^8$=octyl, and Z=—$(CH_2)_{10}$— (i.e., compound 109, Table 2)

Preparation of compound 5 (i.e., a compound of formula 21): Under a nitrogen atmosphere, N,N-dimethyl-1,10-diaminodecane (27.10 mmols) and 2-chloro-N-(2',6'-dimethylphenyl)acetamide (51.49 mmols) were dissolved in 18 mL EtOH. DIPEA (67.75 mmols) was added and the reaction was stirred at reflux for 23 hours. The reaction mixture was concentrated, then taken up in 50 mL EtOAc and the solids filtered. The filtrate was concentrated, taken up in EtOAc, filtered through silica, and concentrated to give 10.06 g (71% yield) of compound 5 (Table 2).

Preparation of compound 109 (i.e., a compound of formula 70): Under a nitrogen atmosphere, the compound above (compound 5) (0.13 mmols) and 1-iodooctane (5.5 mmols) were dissolved in ethanol (10 mL). The reaction was stirred at 85° C. for 18 hrs. The reaction was cooled to room temperature, and the excess iodooctane was removed. The residue was washed with hexanes (×2) at 85° C., then dissolved in MeOH and concentrated to dryness to afford the diquaternary iodide salt (i.e., compound 109, Table 2). MS (found, M+H 749); yield 40%.

20B. In a similar manner, using various compounds of formula (21) as starting material, the following compounds were prepared (Table 2): 110, 111, 112, 113, 114, 115.

20C. Higher-order valency compounds were prepared by a similar procedure.

Example 21

Preparation of a Heterovalomer Compound of Formula Ia, where $(Ar—W)^1$=2,6-dimethyl phenyl-NH—C(O)—$CH_2$— and $(Ar—W)^2$=2,6-dimethyl phenyl-O—CO—$CH_2$—, $R^3=R^4$=methyl, and Z= $(CH_2)_2(CH_2OCH_2)_3(CH_2)_2$ (i.e., Compound 71, Table 2)

Step 1: Under a nitrogen atmosphere, N-methyl-N-(3-{2[-2-(3-methylamino-propoxy)-ethoxy]-ethoxy}-propyl)- amine (130.56 mmols) was dissolved in dioxane (100 mL). Di-tert-butyl dicarbonate ($Boc_2O$) (97.92 mmol) in 50 mL dioxane was added over 1.5 hours. The reaction was stirred at room temperature for 21 hours, then concentrated to dryness. The mixture was partitioned between EtOAc (100 mL) and 10% $KHSO_4$ (50 mL), and the layers separated. The organic layer was washed with 10% $KHSO_4$ (3×50 mL). The aqueous layer was acidified with 6M HCl to PH 3, washed with EtOAc (50 mL), made basic with solid NaOH. Saturated with NaCl, and washed with $CHCl_3$. The combined organic layers were dried over $Na_2SO_4$, filtered, and concentrated to yield N-methyl-N-Boc-N-(3-{2[-2-(3-methylamino-propoxy)-ethoxy]-ethoxy}-propyl)-amine (18.66 g, 41% yield).

Step 2: Under a nitrogen atmosphere, N-methyl-N-Boc-N-(3-{2[-2-(3-methylamino-propoxy)-ethoxy]-ethoxy}-propyl)-amine (53.59 mmols) and 2-chloro-N-(2,6-dimethyl-phenyl)-acetamide (50.91 mmols) were added to ethanol (35 mL). DIPEA (80.39 mmols) was added, and the reaction stirred at 85 C. for 19 hours. The reaction was then concentrated to dryness, dissolved in EtOAc and filtered through silica (EtOAc). The filtrate was reconcentrated to give N-methyl-N-Boc-N-(3-{2-(3-{N-[(2,6-dimethyl-phenylaminocarbonylmethyl)-N-methylamino}-propoxy)-ethoxy]-ethoxy}-propyl)amine (19.36 g, 75% yield).

Step 3: Under nitrogen atmosphere, N-methyl-N-Boc-N-(3-{2-(3-{N-[(2,6-dimethyl-phenylaminocarbonylmethyl)-N-methylamino }-propoxy)-ethoxy]-ethoxy}-propyl)amine (38.04 mmoles) was dissolved in 50 mL dichloromethane. Trifluoroacetic acid (50 mL) was added, and the reaction was stirred at room temperature for 0.5 hours. The reaction was concentrated to dryness, then dissolved in EtOAc (100 mL). The solution was washed with $KHSO_4$ (3×50 Ml). The combined aqueous layers were washed with EtOAc (50 Ml), made basic with solid NaOH, saturated with NaCl, and washed with chloroform (3×50 Ml). The combined organic layers were dried over $Na_2SO_4$, filtered, and concentrated to give N-(2,6-dimethylphenyl)-2-(3-{2-[2-(3-methylaminopropoxy)-ethoxy]-ethoxy}-propylmethylamino)-acetamide (11.58 g, 74% yield). NMR was taken in DMSO.

Step 4: Under a nitrogen atmosphere: 2,6-dimethylphenol (1.0 equivalent, 40 mmoles) was dissolved in dichloromethane (40 mL) and diisopropyl ethylene diamine (1.3 equivalents, 53.2 mmoles). This solution was cooled to −78° C. Chloroacetylchloride was added all at once. The reaction was followed by TLC (25 EtOAc:75 Hexanes) until reaction was complete (~10 minutes). The reaction was extracted using water and ether. The ether layer was washed with water and then brine, dried ($MgSO_4$), filtered, rinsed with ether, and concentrated under vacuum. The concentrate was purified by silica gel column chromatography using hexanes as eluant, to afford 10.5 grams (94.6 % yield) of chloroacetic acid 2,6-dimethyl-phenyl ester product as a tan oil.

Step 5: Under a nitrogen atmosphere in a sealed tube, the chloroacetic acid 2,6-dimethyl-phenyl ester product of Step 4 (1.2 equivalents, 6.72 mmoles) was reacted with 1.0 equivalent (5.6 mmoles) of the monoadduct product of Step 3, diisopropyl ethylene diamine (1.3 equivalents, 6.72 mmoles) and ethanol (1 mL) at 85° C. for 14 hours. The reaction mixture was poured into ether with stirring, and the resulting precipitate was filtered, then dissolved in 90% water, 10% acetonitrile. The product (compound 71, Table 2) was obtained by preparative HPLC eluting with 5% acetonitrile/95% $H_2O$ to 90% acetonitrile/10% $H_2O$. MS (found, M+H 572).

Example 22

22 A. Preparation of a compound of Formula Ia, according to Scheme R, where $(Ar—W)^1$=2,6-dimethyl-4-butoxyphenyl-NH—C(O)—$CH_2$—, $(Ar—W)^2$=2,6-dimethylphenyl-NH—C(O)—$CH_2$—, $R^3$=$R^4$=methyl, and Z —$(CH_2)_4$—, (i.e., compound 144, Table 2)

Step 1: Formation of compound (b): To a mixture of 3,5-dimethylphenol (a) (25 g, 205 mmol) and $NaNO_3$ (26.1 g, 307 mmol) in ether (200 mL) and water (200 mL), at 0° C., 250 mL of conc.HCl solution was added dropwise within 1 hour under stirring. The reaction mixture was kept under stirring overnight and the temperature was allowed to warm to room temperature. The organic phase was seperated and the aqueous phase was extracted with ether (3×100 mL). The combined organic phase was washed with 3N HCl (2×100 mL), saturated $NaHCO_3$ solution (3×100 mL) and finally with brine (200 mL), dried over $Na_2SO_4$, filtered and concentrated to dryness. The obtained residue was purified by chromatography over silica gel by using ethyl acetate and hexane (2:8) as eluent. The collected fractions were further recrystalized in ether/hexane to afford compound (b), 3,5-dimethyl-4-nitrophenol (6.7 g, 19% yield) as a yellow solid. MS: m/e 167

Step 2: Formation of compound (c): A mixture of 3,5-dimethyl-4-nitrophenol (b) (2 g, 12 mmol), bromobutane (1.6 mL, 15 mmol), $K_2CO_3$ (2.1 g, 15 mmol) in DMF (6 mL) was stirred at 60° C. for 6 hours. The reaction mixture was poured into 50 mL of $H_2O$ and extracted with ether (3×50 mL). The combined ether layer was washed with $H_2O$ and subsequently with brine, dried over $Na_2SO_4$, filtered and concentrated to give compound (c), 4-butoxy-2,6-dimethyl-nitrobenzene (2.6 g, 97% yield) as a dark brown oil. $^1$H-NMR in $CDCl_3$.

Step 3: Formation of compound (d): A solution of 4-butoxy-2,6-dimethyl-nitrobenzene (c) (7.76 g, 34.8 mmol) in methanol (200 mL) was hydrogenated overnight at 35 psi, in the presence of 10% Pd/C (1.5 g) and 3 mL of conc.HCl. The reaction mixture was then filtered and the filtrate was concentrated to dryness. The obtained residue was partitioned into $CHCl_3$/i-PrOH (4:1 v/v) and saturated $NaHCO_3$ solution, and extracted with $CHCl_3$/i-PrOH (4:1 v/v). The organic phase was dried over $Na_2SO_4$, filtered and concentrated to give 4-butoxy-2,6-dimethyl-phenylamine (d), (6.5 g, 97% yield) $^1$H-NMR in $CDCl_3$. (TLC system: Rf: 0.15 with EtOAc/hexane=2/8)

Step 4: Formation of compound (e): To a solution of 4-butoxy-2,6-dimethyl-phenylamine (d) (1.4 g, 7.4 mmol) and diisopropylethylamine (1.4 mL, 8.0 mmol) in $CH_2Cl_2$ (6 mL), 2-chloro-acetylchloride (0.88 mL, 11.0 mmol) in $CH_2Cl_2$ (6 mL) was added slowly at 0° C. The ice-bath was removed and the reaction mixture was kept under stirring for 0.5 hour. The reaction mixture was concentrated and the crude concentrate was partitioned between ethyl acetate and water. The organic phase w as washed with water twice. The organic phase was dried over $Na_2SO_4$ and concentrated to dryness. The residue was was purified by flash chromatography over silica-gel using ethyl acetate/hexane (20/80 v/v) to afford 2-chloro-N-(4-butoxy-2,6-dimethyl-phenyl)-acetamide (e) (1.95 g, 98% yield), $^1$H-NMR in $CDCl_3$.

Steps 5 and 6: Formation of compound (f)

A solution of trans-1,4-dibromobutene (80 g, 374 mmol, Fluka 34060) in 500 mL of THF/EtOH (1/2) was added dropwise to a solution of 8N methylamine in EtOH (1 L), which is kept at a temperature below 35° C. by using an ice-bath. After the addition, the reaction mixture was stirred at 38° C. for approximately 24 hours and then concentrated to yield a precipitate. The solid was filtered, washed with acetone to give N,N'-dimethyl-1,4-butenediamine dihydrobromide (53.8 g, 52% yield) as a white solid, which was hydrogenated in 350 mL MeOH/$H_2O$ (6:1 v/v) for 20 hours at 35 psi and in the presence of 10 g of 10% Pd/C. The catalyst was filtered and washed with MeOH and $H_2O$. The filtrate was concentrated and precipitated by adding acetonitrile. The solid was filtered and washed with acetonitrile to give N,N'-dimethyl-1,4-butanediamine dihydrobromide (f) as a white solid (45.5 g, 93% yield).

Step 7: Formation of compound (h)

2-Chloro-N-(2,6-dimethylphenyl)acetamide (g) (2.8 g, 14.2 mmol) was added to a mixture of N,N'-dimethylbutane dihydrobromide (f) (7.68 g, 27.6 mmol) and DIPEA (8 mL, 46 mmol) in EtOH (200 mL). The mixture was stirred at 90° C. overnight, then concentrated to yield a white precipitate, which was filtered off. The filtrate was concentrated and purified by chromatography over silica-gel by using $CH_2Cl_2/CH_3OH/25\%$ aq.$NH_3$ (97/2.5/0.5→95/4.5/0.5→90/9/1 by volume) as eluent to obtain the desired monoadduct (h) as a colorless foam (2.62 g, 67% yield). MS: m/e 278 (M+H)), $^1$H-NMR in $CD_3OD$.

Step 8: Formation of compound 144 (Table 2)

A mixture of 2-chloro-N-(4-butoxy-2,6-dimethylphenyl)-acetamide (e) (2.5 g, 9.2 mmol), the monoadduct (h) (2.5 g, 9.2 mmol) and DIPEA (2.1 mL, 12 mmol) in EtOH (45 mL) was refluxed overnight. The reaction mixture was concentrated and the obtained residue was purified by chromotography over silica gel by using $EtOAc/hexane/Et_3N$ (50:49:1), then $EtOAc/Et_3N$ (99:1) and subsequently $CH_2Cl_2/CH_3OH/25\%$ aq.$NH_3$ (94/5.4/0.6) as eluant to obtain compound 144 (0.28 g, 55% yield). This compound was converted to its dihydrochloride salt by treatment with 4N HCl solution in dioxane. MS: m/e 511 (M+H), and $^1$H-NMR in $CD_3OD$.

22B. In a similar manner, by substituting other other Ar—$W^2$ groups for 2,6-dimethylphenyl-NH—C(O)—$CH_2$— and/or other bromoalkanes for bromobutane in Example 22A, the following compounds were prepared (Table 2): 167, 168, 169.

22C. Preparation of a compound of Formula Ia, according to Scheme R, where $(Ar—W)^1$=2,6-dimethyl-4-(O—$CH_2$—C(O)—$OCH_3$-phenyl-, $(Ar—W)^2$=2,6-dimethylphenyl-NH—C(O)—$CH_2$—, $R^3$=$R^4$=methyl, Z=—$(CH_2)_4$—, (i.e., compound 145, Table 2)

Compound 145 was prepared in a similar manner as described above for compound 144, with the modification that in Step 2 of the procedure, methyl bromoacetate (i.e., $BrCH_2C(O)OCH_3$) is substituted for bromobutane.

22D. In a similar manner, replacing methyl bromoacetate with other esters of bromoacetate, the following compounds were prepared (from Table 2): 152, 159, 162, 165, 166.

22E. In like manner, other compounds of Formula I were prepared by varying the linker group (f) (Step 7), and/or the ligand groups $(Ar—W)^1$ and $(Ar—W)^2$ and the substituents $R^1$ and R thereof.

22F. Compounds that are useful intermediates in the synthesis of compounds described in Examples 22C and 22D were prepared by substituting bromoacetic acid for methylbromoacetate in Step 2 of Example 22B. These intermediates include compounds 153 and 170 (Table 2).

In like manner, other useful intermediates in the synthesis of compounds of Formula I described in Example 22 were prepared by varying the linker group (f) (Step 7), and/or the ligand groups $(Ar—W)^1$ and $(Ar—W)^2$ and the substituents R' and R thereof, and/or by varying the carbon chain length of the α-haloacids.

Example 23

Preparation of a Heterovalomer Compound of Formula Ia, According to Scheme Q, where (Ar—$W^1$)=[4-(C(O)—O—$(CH_2)_2$—$N(CH_3)_2$)-phenyl]-, (Ar—$W^2$)=2,6-dimethylphenyl-NHC(O)—$CH_2$—, $R^3$=H, $R^4$=methyl, and Z=—$(CH_2)_5$— (i.e., Compound 133, Table 2)

Step 1: A mixture of 4-trifluoroacetylamino-benzoic acid benzyl ester (47) (2.5 g, 7.74 mmol), 1,5-diiodopentane (12.5 g, 38.6 mmol), potassium carbonate (4.3 g, 31.1 mmol) and benzenetriethylammonium bromide (420 mg, 1.54 mmol) in acetonitrile (150 ml) was stirred under reflux overnight. After cooling to room temperature, the reaction mixture was filtered and the filtrate was concentrated. The resulting residue was purified by chromatography over silica gel using ethyl acetate/hexane (1/9 by volume) as eluent to obtain the desired compound (76) (3.3 g, 82% yield), $^1$H-NMR in $CDCl_3$, MS: m/e 520 (M+H).

Step 2: A mixture of N-(2,6-dimethylphenyl)-2-methylamino-acetamide (2.4 g, 12.5 mmol) (23), compound (76) (3.2 g, 6.16 mmol) and potassium carbonate (4.3 g, 31.1 mmol) in acetone was stirred at 60 C. overnight. The reaction mixture was filtered and the filtrate was concentrated. The resulting residue was purified by chromatography over silica gel to obtain the desired compound (77) (1.8 g, 50% yield), $^1$H-NMR in $CDCl_3$, MS: m/e 584 (M+H).

Step 3: A solution of compound (77) (1.8 g, 3.08 mmol) in tetrahydrofuran (80 ml) was stirred under $H_2$ atmosphere and in the presence of 10% Pd/C (1 g) for 16 hours. The reaction mixture was filtered and the filtrate was concentrated to give compound (78) as a white foam (1.35 g, 89% yield) MS: m/e 494 (M+H).

Step 4: A mixture of compound (78) (0.77 g, 1.56 mmol), HATU (1.8 g, 4.73 mmol), HOAT (0.065 g, 0.47 mmol), N,N-dimethylethanolamine (0.47 ml, 4.68 mmol) and DIPEA (0.82 ml, 4.7 mmol) in anhydrous tetrahydrofuran (34 ml) was stirred at room temperature overnight. The reaction mixture was concentrated and subsequently purified by chromatography over silica gel using $CH_2Cl_2/CH_3OH/25\% NH_4OH$ (98.8/1/0.2 à94/5.4/0.6 by volume) as eluant to afford the desired compound (79) (0.5 g, 57% yield), MS: m/e 565 (M+H).

Step 5: Compound (79) (0.5 g, 0.89 mmol) was dissolved in a solution of 2N methylamine in tetrahydrofuran. The resulting solution was stirred at room temperature overnight and then concentrated. The residue was purified by chromatography over silica gel using $CH_2Cl_2/CH_3OH/25\%NH_4OH$ (98.8/1/0.2→94/5.4/0.6 by volume) as eluant to afford the desired heterovalomer compound (80) (i.e., compound 133 in Table 2), (0.15 g, 36% yield). MS: m/e 469 (M+H). This compound was converted to the dihydrochloride salt by treatment with 4N HCl solution in dioxane.

Example 24

24 A. Preparation of a compound of Formula Ib, according to Scheme T, where (Ar—$W^1$)=2,6-dimethylphenyl-NH—C(O)—$N(CH_3)_2$—(S-isomer), (Ar—$W^2$)=2,6-dimethylphenyl NHC(O)—$CH_2$—, $Y^a$=—$(CH_2)_3$—, $Y^b$=covalent bond, Z=—$N(CH_3)$— (i.e., compound 116, Table 2)

Step 1: S(L)-ornithine protected on the α-amino group with Boc and on the δ-amino group with Cbz (2.96 g, 8.08 mmol) was dissolved in 30 mL dry DMF. HATU (3.63 g, 9.55 mmol), HOAT (0.1 g, 0.73 mmol) and DIPEA (1.41 g, 10.9 mmol) were added and the mixture was stirred at room temperature for 40 min. 2,6-dimethylaniline (0.886 g, 7.31 mmol) was added and the reaction mixture was stirred overnight at room temperature under $N_2$ atmosphere. The mixture was evaporated and resuspended in EtOAc, then washed with brine, and extracted with EtOAc. The organic phases were combined, dried($MgSO_4$), evaporated then resuspended and chromatographed on a silica gel column with 2% $MeOH/CH_2Cl_2$ as eluant. The product, a compound of formula (91) was obtained as a yellow solid (4.33 g, >99% yield), and was characterized by NMR ($CDCl_3$).

Step 2: The product of the previous step was dissolved in MeOH and 10%Pd/C (0.25 g) was added and stirred. The reaction vessel was evacuated, then $H_2$ was added and the solution was stirred at room temperature for 2 hours until the reaction was judged complete by TLC. The catalyst was removed by filtration and the filtrate was concentrated to afford a compound of formula (92) as a yellow oily foam (2.87 g).

Step 3: The product of the previous step (2.87 g, 8.55 mmol) was reacted at 80° C. overnight with 2-chloro-N-(2', 6'-dimethylphenyl)acetamide (1.52 g, 7.69 mmol) (prepared as in Example 5 above) in the presence of DIPEA ((1.22 g, 9.47 mmol) in EtOH (25 mL). The reaction was concentrated and the residue dissolved in $CH_2Cl_2$. The organic phase was washed with three portions of 0.3N HCl. The aqueous layers were combined and the pH adjusted to 11 by dropwise addition of 5N NaOH. The resulting suspension was extracted with three portions of $CH_2Cl_2$, and these organic phases were combined, dried ($MgSO_4$) evaporated, then resuspended and chromatographed on silica gel (12.5× 14 cm column), eluted with 2% MeOH (400 mL), 3% MeOH/$CH_2CH_2$ (300 mL), and 5% MeOH (300 mL) to afford the product, a compound of formula (93), as a pale yellow foam (1.59 g).

Step 4: The product (93) (0.6 g) was dissolved in $CH_2Cl_2$ and TFA was added with stirring for 1 hour until deprotection was complete, as judged by TLC. The reaction mixture was evaporated, and the residue redissolved in $CH_2Cl_2$. The organic phase was washed with three portions of 0.3N HCl. The aqueous layers were combined and the pH adjusted to 11 by dropwise addition of 5N NaOH. The resulting suspension was extracted with three portions of $CH_2Cl_2$. These organic layers were combined, dried ($MgSO_4$) and concentrated to afford the deprotected product, a compound of formula (94) as a viscous foam (350 mg).

Step 5: The product (94) (0.149 g, 0.376 mmol) was dissolved in MeOH (25 mL). Formaldehyde (37% aqueous) (0.46 mL) was added, followed by $NaBH_3CN$ (117 mg) and alkylation was carried out for 1 hour. The pH of the reaction was then adjusted with glacial acetic acid to about pH 6 and the reaction mix stirred for 30 min. The pH was then raised to pH 9 with $NH_4OH$ and the reaction mix was concentrated by evaporation to a slurry. The slurry was redissolved in $CH_2Cl_2$, washed with saturated $NaHCO_3$ and extracted 3× with $CH_2Cl_2$. The organic phases were combined, dried ($MgSO_4$), concentrated by evaporation and the residue was purified by chromatography on silica gel eluted with 400 mL of 2%, 4%, and 5% MeOH/$CH_2Cl_2$ to afford the desired compound (95) (i.e., compound 116, Table 2) (0.135 g, 0.308 mmol; 82% yield). The compound was converted to the HCl salt (0.12 g). The product was characterized by MS (observed, M+1=439) and NMR (DMSO).

24 B. In a similar manner, compound 121 was prepared by substituting the diprotected S(L) lysine derivative for the corresponding S(L) ornithine derivative. Compounds 123 and 124 were prepared by substituting, respectively, diprotected R(D) lysine and diprotected R(D) ornithine for the corresponding diprotected S(L) ornithine in Step 1 of Example 24 A.

24C. Compound 127 was prepared with the following modifications from the procedure described in Example 24A. S(L)-2,5-diaminobutanoic acid that was N-protected with Boc ($PG_1$) and FMoc ($PG_2$) was used in place of the diprotected S(L) ornithine derivative in 24A. Accordingly, Step 2 (deprotection) was carried out in DMF with piperidine. The reaction was carried out until complete, as judged by TLC, and the crude product was obtained as a solid on evaporation. This product was purified by chromatography on silica gel, using successive elutions with 300 mL 4% MeOH/$CH_2Cl_2$, followed by 5.4% MeOH+0.6% $NH_4OH$. The latter afforded the deprotected product, which was evaporated and characterized by MS.

24D. Compound 137 can be prepared by the procedure described above in 24A by substituting a diprotected S(L) lysine derivative for the corresponding S(L) ornithine derivative. However, it is preferred to carry out Step 5 by a direct alkylation route, as described below.

In Step 5, a compound of formula (95), where n=4 (0.237 g, 0.577 mmol) was reacted overnight at 80° C. with EtBr (100µL). The reaction mixture was evaporated, and the residue redissolved in $CH_2Cl_2$. The organic phase was washed with three portions of 0.3N HCl. The aqueous layers were combined and the pH adjusted to 11 by dropwise addition of 5N NaOH. The resulting suspension was extracted with three portions of $CH_2Cl_2$. These organic layers were combined, dried($MgSO_4$) and concentrated. The crude product was chromatographed on silica gel with 2% MeOH/$CH_2Cl_2$ as eluant. The product was eluted and rechromatographed using 1% MeOH/$CH_2Cl_2$ as eluant to afford the desired product (compound 137, Table 2) (0.150 g, 53 % yield. Characterized by MS (observed, M+1=495) and NMR (DMSO). The product was converted to the HCl salt, yielding 0. 12 g as a white powder.

24E. By a procedure similar to that described in 24D, but with the following modifications, compound s 122, 138, 139 and 154 were prepared.

Compound 122: diprotected S(L)-ornithine was used in place of the corresponding diprotected S(L)-lysine derivative.

Compound 138: diprotected R(D)-lysine was used in place of the corresponding diprotected S(L)-lysine derivative.

Compound 139: diprotected R(D) ornithine was used in place of the corresponding diprotected S(L) lysine derivative.

Compound 154: diprotected R(D) ornithine was used in place of the corresponding diprotected S(L) lysine derivative; the compound of formula (e) in Scheme R, where the R substituent is 4'-[O—$CH_2C(O)$—$OCH_3$]— was used in place of 2-chloro-2',6'-acetoxylidide in step 3 of Example 24A.

It should be understood, of course, that the R- and S-isomer of compounds of this invention may differ in activity and/or other properties. It is well within the skill in the art to test different isomers and combinations thereof to determine which is more active for any particular intended use.

Examples 25–28

Assay Procedures

The multibinding compounds of Formula I were found to exhibit significant activity in the assays described below, and demonstrated improved properties when compared to conventional local anesthetics (i.e., lidocaine, bupivacaine).

Example 25

BTX Displacement Assay

The local anesthetic binding site in the sodium ion channel is allosterically linked to the binding site for batrachotoxin (BTX). The displacement of radiolabeled BTX from Site 2 on synaptosomal membranes correlates with local anesthetic activity.

1. Preparation of Synaptosomes

Synaptosomes were prepared using frozen rat brains obtained from Pel-Freez. Ten brains were thawed and the cerebral cortex harvested (cerebellum removed). Approximately 4 to 5 g of cortex were placed in 50 mL of 0.32 M sucrose at 0° C. and homogenized in a Teflon/glass homogenizer (clearance approx. 0.15–0.23 mm, 12 up and down strokes at less than 800 rpm) while the mortar of the homogenizer was kept in an ice/water bath. The crude homogenates were pooled and distributed as 20 mL aliquots into polycarbonate centrifuge bottles. These were centrifuged at 5,100 rpm (($\omega^2 t$ setting $1.57 \times 10^8$ rad$^2$/sec) in a 50.2 Ti rotor for approximately 9 min at 4° C. in a Beckman L8-80M ultracentrifuge. The pellet (P1) was discarded. The supernatant (nominally in 0.32 M sucrose) was removed, layered onto 8 mL of 1.2 M sucrose at 0° C. and spun at 50,000 rpm ($\omega^2 t$ setting $1.6 \times 10^{10}$ rad$^2$/sec) for approximately 10 min in a 50.2 Ti rotor at 4° C. Supernatant (4 mL) was removed from the gradient interface and mixed with 10 mL of 0.32 M sucrose at 0° C. The pellet (P2) and other material was discarded. The diluted interface was layered onto 8 mL of 0.8M sucrose and spun at 50,000 rpm ($\omega^2 t$ setting $1.6 \times 10^{10}$ rad$^2$/sec) for approximately 10 min in a 50.2 Ti rotor at 4° C. The supernatant was discarded, and the pellets (P3) were pooled and resuspended by homogenization at 0° C. with a Wheaton glass homogenizer B type (clearance approx. 0.15–0.23 mm, 12 up and down strokes) in 15 mL synaptosomal storage buffer (130 mM choline Cl, 5.5 mM glucose, 5.4 mM KCl, 0.8 mM MgSO$_4$), 4.50 mM HEPES, pH adjusted to 7.4 with Tris Base (approx. 22 mM)). The homogenized solution was spun at 50,000 rpm ($\omega^2 t$ setting $1.6 \times 10^{10}$ rad$^2$/sec) for approximately 10 min in a 50.2 Ti rotor at 4° C. The supernatant was discarded, and the pellet (P4) was resuspended in 8 mL synaptosomal storage buffer by homogenization (as in the previous step) at 0° C. The synaptosomes were "snap frozen" in 500 μl aliquots on ethanol/dry ice and stored at −80° C. Total protein concentration was measured after solubilizing membranes in 1.2% (wt/vol) SDS by Lowry's method.

2. BTX Displacement Assay

Incubations were carried out in a total volume of 250 μl containing synaptosomes at a final concentration of 0.8 μg total protein/μl, 50 nM $^3$H-BTX-13 (50 Ci/mmol), 1 μM tetrodotoxin, 120 μg/mL Leiurus quinquestriatus venom, in synaptosome storage buffer (see above). Test compound was added at various concentrations, typically from 1 to 100 μg/mL. Systems were incubated for 30 to 45 min at 37° C., after which time incubation was terminated by dilution of the reaction mixture with 250 pl of wash buffer (163 mM choline Cl, 5 mM HEPES, 1.8 mM CaCl$_2$ and 0.8 mM MgSO$_4$, pH to 7.4 with Tris base) at 0° C., and solutions were filtered through a Millipore GFC 96 well filter plate. Filtration was accomplished by vacuum filtration through a Millipore 96 well vacuum manifold. Each filter plate was washed three times with wash buffer at 0° C. (250 μl/wash). Filter and filtrate were counted in 25 μl of OptiPhase Supermix (Wallac) on a Wallac scintillation counter (model 1450 Microbeta). Nonspecific binding was determined by parallel experiments in the presence of 300 μM veratridine.

Example 26
Whole-Cell Voltage Clamp

The whole cell variant of the patch-clamp method (Hamill et al., *Pflügers Arch.* 391:85–100, 1981) was used to measure Na$^+$ currents in GH$_3$ cells. The external solution contained (in mmol) 150 choline Cl, 0.2 CdCl$_2$, 2 CaCl$_2$, and 10 hydroxethylpiperazine ethane sulfonic acid (HEPES) adjusted to pH 7.4 with tetramethyl hydroxide. Micropipettes were fabricated and had a tip resistance of ~1 MΩ when filled with an Na+ solution containing (in mmol) 100 NaF, 30 NaCl, 10 EGTA (ethylene glycol-bis(P-aminoethyl ether)-N,N,N',N'-tetraacetic acid), and 10 hydroxyethyl-piperazineethane sulfonic acid, adjusted to pH 7.2 with CsOH.

The junction potential of electrodes was nulled before seal formation. After the rupture of the patch membrane, the cell was allowed to equilibrate with the pipette solution for at least 15 min at the holding potential of −100 mV. Under these reversed Na$^+$ gradient conditions, outward Na$^+$ currents were activated at approximately −30 mV.

Test compounds, at appropriate concentrations, were applied to cells with a flow rate of about 0.12 mL/min via a series of narrow-bored capillary tubes positioned within 200 μm of the cell. Typically, the more soluble salt form, rather than the free base, was used. Washout of drugs was performed via a tube containing the external solution without drug present. Voltage-clamp protocols were created with pClamp software (Axon Instruments, Inc., Foster City, Calif.). Leak and capacitance were subtracted by a leak and capacity compensator (Hille and Campbell, *J. Gen. Physiol.* 67:265–93, 1976). Additional compensation was achieved by the patch clamp device (EPC7, List-Electronic, Darmstadt/Eberstadt, Germany). All experiments were performed at room temperature. At the end of the experiments, the drift in the junction potential was generally <2 mV.

Example 27
Rat Sciatic Nerve Sucrose-Gap Assay

Sprague-Dawley rats (42–56 days old) obtained from Charles River Laboratories were used in these experiments. Animals were euthanized and the sciatic nerves were excised and maintained in Ringer solution.

The Ringer solution contained: 124 mM NaCl, 3 mM KCl, 1.3 mM NaH$_2$PO$_4$, 2 mM MgCl$_2$ H$_2$O, 2 mM MgCl$_2$ 6H$_2$O, 26 mM NaHCO$_3$, and 10 mM Dextrose. The pH was adjusted to 7–7.5 using bubbled 95% O$_2$–5% CO$_2$ This Ringer solution was used for storing nerves and for filling the two stimulating pools (500 ul) and the recording "intracellular" pool.

The compounds to be tested for local anesthetic activity were prepared as 10 mM solutions in 15% PEG 400. The solutions were stored at 4° C. to minimize loss of potency. The working solutions were prepared by diluting stock solution in Ringer solution just prior to their use in experiments.

Segments of nerves measuring 5mm were desheathed and mounted in a polycarbonate sucrose-gap chamber. In the chamber, the nerves were laid across a series of pools and within a cylindrical gap with the proximal end in the "test" pool. Petroleum jelly (Vaseline, Cheeseborough Pons) was used to create watertight seals around regions of the nerves passing between aqueous pools.

The proximal end of the nerve was stimulated by a pair of bipolar Ag/AgCl electrodes inserted into the stimulating pools. The "test" pool (500 μl volume) contained the Ag/AgCl electrode that recorded the extracellular electrical potential. Flowing at 1.0 mL/min, a nonionic sucrose solution (320 mM) prevented the action potential from propagating beyond the test pool. The intracellular potential, conducted passively through the sucrose gap to the distal end of the preparation, was recorded using Ag/AgCl ("intracellular") electrodes in a Ringers containing pool. Using a stimulator (A360 Stimulus Isolator, WPI), nerves were stimulated for 0.1 ms at two times the intensity required to induce the maximal compound action potential (CAP). The electrical signal from the nerve, the compound action potential (CAP) from large myelinated fibres, was amplified 10 times using an amplifier (IsoDam 8, WPI). The signal was displayed on an oscilloscope and also recorded on a computer using BioPak software. A nerve preparation was considered acceptable if the CAP measured not less than 10 mV, and the experiment was carried out after CAP stabilized (i.e. did not vary more than 1–2 mV over a 10–20min period).

Nerves were stimulated at less than 1 Hz during the full experiment time to assess "tonic" block, and "phasic" block was measured by 50 Hz trains applied 400 ms every 4 secs. All data were recorded at room temperature.

Example 28

Measurement of sciatic nerve block in the rat

Sprague-Dawley male rats in groups of 3–6 were injected percutaneously with a 27 G needle close to the sciatic nerve (about one third of the distance between the greater trochanter and the ischial tuberosity and caudal to the greater trochanter) with 0.2 mL of 10–90 mM solution of test compounds, pH 3–4.5 (i.e., compounds of Formula I, lidocaine and bupivacaine (Marcaine®)). Animals were observed at least three times on the day of the procedure, and each day thereafter.

At 3, 15 and 30 minutes and every 30 minutes thereafter for up to 10 hours after injection, the animals were assessed for motor and sensory nerve block. Where the anesthesia lasted longer than 10 hours, daily assessments were made for up to 5 days. Motor deficit was assessed by placing the animal on a flat surface and noting whether the paw is spread out under the animal (normal position) or whether it is kept closed and not used for locomotion (deficit). For assessment of sensory block, the animal was held above the bench surface and the skin between the two lateral-most toes was pinched using a pair of "rat-tooth forceps". A withdrawal response is normal, whereas no response indicates sensory block.

In animals that showed full recovery of motor and sensory nerve function within 48 hours, a second compound is tested after a period of one week has elapsed. The tests are performed in the same way as described above, but on the contralateral limb. Results are analyzed for statistical significance using a one way analysis of variance.

Example 29

Use of a compound of Formula I for surgical anesthesia and/or post-operative analgesia Compounds of Formula I are used in patients requiring both surgical anesthesia and post-operative analgesia (e.g., surgical repair of an inguinal hernia) or post-procedure pain relief only (e.g., post-operative pain relief of long duration; post-arthroscopy).

A patient requiring surgical repair of an inguinal hernia is prepared for surgery. It is desired to provide local anesthesia prior to incision, and for 18 to 36 hours post-operatively. Accordingly, prior to incision, a sterile injectable solution containing about 0.1–2.5% of a compound of Formula I (with or without 5 ug/mL epinephrine, at the discretion of the surgeon) is infiltrated incrementally at the site of incision until the patient no longer senses cutaneous pain when pinched with a hemostat. Additional drug is administered during the procedure if required. The total volume of solution required is in the range of about 10–30 mL.

For post-operative analgesia in a patient requiring a major abdominal operation (e.g., a C-section), who will receive a general anesthetic during the operation, the wound area is infiltrated either pre-incisionally or at the end of the procedure with a compound of Formula I.

For relief of joint pain following an arthroscopic procedure, the patient's joint is infiltrated with a compound of Formula I.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

What is claimed is:

1. A compound of the formula:

or a pharmaceutically acceptable salt thereof; wherein:

each L independently comprises a group of formula A:

wherein:

Ar represents an aryl, heterocyclyl or heteroaryl group;

W is —NH—C(O)—$CR^1R^2$— and $R^1$ and $R^2$ are independently hydrogen, allyl, substituted allkyl or a group —$NR^aR^b$, where $R^a$ and $R^b$ are both alkyl;

X is an N-containing heterocyclic ring selected from the group consisting of:

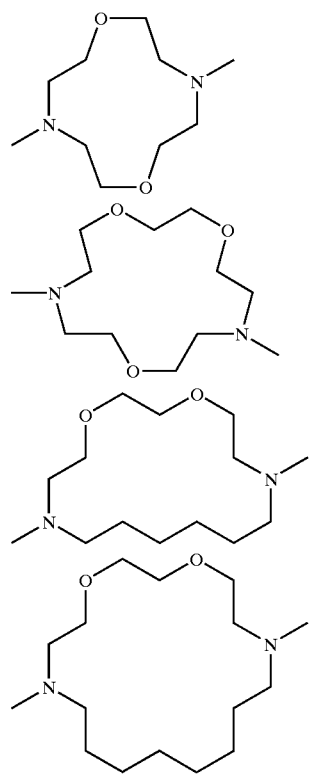

-continued

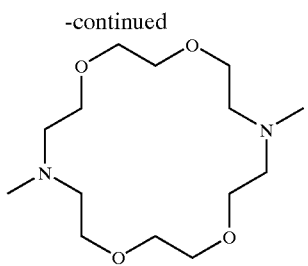

2. The compound of claim 1, wherein $R^1$ and $R^2$ are hydrogen.

3. The compound of claim 1, wherein $R^1$ is hydrogen and $R^2$ is alkyl.

4. The compound of claim 1, wherein one or both Ar groups is independently selected from the group consisting of:
2,6dimethylphenyl;
4-[O—CH$_2$)$_7$CH$_3$]-2,6-dimethylphenyl;
4-butylaminophenyl;
4-methoxyphenyl;
phenyl;
4-chlorophenyl;
2-methyl-4-methoxyphenyl;
2-methyl-4-chlorophenyl;
4-aminophenyl;
4-nitrophenyl;
2-chloro-4-nitrophenyl;
2,4,6-trimethylphenyl;
2-ethyl-6-methylphenyl;
4-[O—CH$_2$—C(O)—O—CH$_2$CH$_3$]-2,6-dimethylphenyl;
4-[O—(CH$_2$)$_3$CH$_3$]-2,6-dimethylphenyl;
4-[O—CH$_3$—C(O)—O—CH$_3$]-2,6-dimethylphenyl;
4-[O—CH$_2$—C(O)—O—CH$_2$CH$_3$]-2,6-dimethylphenyl;
4-[C(O)—O—CH$_3$]-2,6-dimethylphenyl;
4-[C(O)—O—CH$_3$]-2-methylphenyl;
2-methylphenyl;
2-methyl-6-methoxyphenyl;
2-methyl-6-carboxyphenyl;
2,6-dimethyl-4-(methoxycarbonylethyl)phenyl;
2-methyl-3-(ethoxycarbonylmethoxy)phenyl;
2-methyl-6-(methoxycarbonylvinyl)phenyl;
2-methyl-6-(methoxycarbonylethyl)phenyl;
2,6-dimethyl-4ethoxycarbonylethyl)phenyl;
2,6-dimethyl-4-(n-propoxycarbonylethyl)phenyl;
2,6dimethyl-4-(isopropoxycarbonylethyl)phenyl;
2,6dimethyl-4-(n-butoxycarbonylethyl)phenyl;
2,6-dimethyl-4-(sec-butoxycarbonylethyl)phenyl; and
2,6-dimethyl-4-(t-butoxycarbonylethyl)phenyl.

5. The compound of claim 1, wherein one or both Ar—W— groups is independently selected from the group consisting of:
2,6-dimethylphenyl-NH—C(O)—CH$_2$—;
2,6-dimethylphenyl-NH—C(O)—CH(CH$_2$CH$_2$CH$_3$)—;
(S)-2,6-dimethylphenyl-NH—C(O)—CH(CH$_2$CH$_3$)—;
(R)-2,6-dimethylphenyl-NH—C(O)—CH(CH$_2$CH$_3$)—;
o-tolyl-NH—C(O)—CH(CH$_2$CH$_3$)—;
o-tolyl-NH—C(O)—CH(CH$_3$)—;
o-tolyl-NH—C(O)—CH$_2$—;
4-[—C(O)—O—CH$_2$CH$_3$]-2,6-dimethylphenyl-NH—C(O)—CH$_2$—;
4-[—C(O)—O—CH$_3$]-2,6-dimethylphenyl-NH—C(O)—CH(CH$_2$CH$_3$)—;
4-[—C(O)—O—CH$_3$]-2-methylphenyl-NH—C(O)—CH(CH$_2$CH$_3$)—;
4methoxyphenyl-NH—C(O)—CH$_2$—;
2methylphenyl-NH—C(O)—CH$_2$—;
phenyl-NH—C(O)—CH$_2$—;
4-chlorophenyl-NH—C(O)—CH$_2$—;
2-methyl-4-methoxyphenyl-NH—C(O)—CH$_2$—;
2-methyl-4-chlorophenyl-NH—C(O)—CH$_2$—;
(S)-2,6-dimethylphenyl-NH—C(O)—CH(N(CH$_3$)$_2$)—;
(R)-2,6-dimethylphenyl-NH—C(O)—CH(N(CH$_3$)$_2$)—;
(S)-2,6-dimethylphenyl-NH—C(O)—CH(N(CH$_2$CH$_3$)$_2$)—;
(R)-2,6-dimethylphenyl-NH—C(O)—CH(N(CH$_2$CH$_3$)$_2$)—;
4-{O—[(CH$_2$)$_n$—C(O)—O]$_m$R}-2,6-dimethylphenyl-NH—C(O)—CHR'—, where n is an integer equal to 1 to 6, m is 0 or 1, R is C$_1$–C$_6$ alkyl, and R' is H or alkyl;
2-ethyl-6-methylphenyl-NH—C(O)—CH(CH$_2$CH$_3$)—; and
2-ethyl-6-methylphenyl-NH—C(O)—CH(CH$_2$—.

6. The compound or claim 1, wherein X is an N— containing heterocyclic ring of the formula:

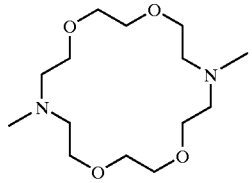

7. The compound of claim 6, wherein Ar at each occurrence is substituted with one to five groups selected from alkyl, alkoxy and substituted alkoxy.

8. The compound of claim 7, wherein each Ar is independently selected from the group consisting of 2,6-dimethylphenyl, o-tolyl and 4-{O—[(CH$_2$)$_n$—C(O)—O]$_m$R}-2,6-dimethylphenyl, where n is an integer equal to 1 to 6, m is 0 or 1, and R is C$_1$–C$_6$ alkyl; and each W is independently selected from the group consisting of —NH—C(O)—CH$_2$—, —NH—C(O)—C*H(CH$_3$)— and —NH—C(O)—C*H(CH$_2$CH$_3$)—, where the symbol * denotes a chiral center.

9. The compound of claim 8, wherein Ar is 2,6-dimethylphenyl and W is —NHC(O)C*H(CH$_2$CH$_3$)—.

10. The compound of claim 8, wherein one of the Ar—W groups is 2,6dimethylphenyl-NH—C(O)—CH$_2$— and the other Ar—W group is o-tolyl-NHC(O)C*H(CH$_3$)—.

11. The compound of claim 8, wherein one of the Ar groups is 2,6-dimethylphenyl, the other Ar group is o-tolyl; and W is —NHC(O)C*H(CH$_2$CH$_3$)—.

12. A pharmaceutical composition comprising a pharmaceutically acceptable excipient and a therapeutically effective amount of a compound of any of claims 1, 2–5, 6–11.

13. A method for producing local anesthesia or analgesia in a mammal, the method comprising administering to a mammal a pharmaceutical composition comprising a pharmaceutically acceptable excipient and a therapeutically effective amount of a compound of any of claim 1, 2–5, 6–11.

14. A method for modulating the activity of a voltage-gated Na$^+$ ion channel in a mammal, the method comprising administering to a mammal a voltage-gated Na$^+$ ion channel modulating amount of a compound of claim 1.

* * * * *